(12) United States Patent
Frazier et al.

(10) Patent No.: US 9,221,908 B2
(45) Date of Patent: *Dec. 29, 2015

(54) THERAPEUTIC CD47 ANTIBODIES

(71) Applicant: Vasculox Inc., St. Louis, MO (US)

(72) Inventors: William A. Frazier, St. Louis, MO (US); Pamela T. Manning, Chesterfield, MO (US); Gerhard Frey, San Diego, CA (US); Hwai Wen Chang, San Marcos, CA (US)

(73) Assignee: Vasculox, Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/104,007

(22) Filed: Dec. 12, 2013

(65) Prior Publication Data

US 2014/0161799 A1 Jun. 12, 2014

Related U.S. Application Data

(60) Provisional application No. 61/736,301, filed on Dec. 12, 2012.

(51) Int. Cl.
 *C07K 16/30* (2006.01)
 *C07K 16/28* (2006.01)

(52) U.S. Cl.
 CPC ......... *C07K 16/2803* (2013.01); *C07K 2317/24* (2013.01); *C07K 2317/33* (2013.01); *C07K 2317/73* (2013.01)

(58) Field of Classification Search
 CPC .............. C07K 16/2803; C07K 16/2896
 See application file for complete search history.

(56) References Cited

U.S. PATENT DOCUMENTS

| | | | |
|---|---|---|---|
| 7,514,229 B2 | 4/2009 | Jamieson et al. | |
| 7,531,643 B2 | 5/2009 | Fukushima et al. | |
| 7,696,325 B2 | 4/2010 | Fukushima et al. | |
| 8,101,719 B2 | 1/2012 | Kikuchi et al. | |
| 8,236,313 B2 | 8/2012 | Isenberg et al. | |
| 8,562,997 B2 | 10/2013 | Jaiswal et al. | |
| 8,728,476 B2 | 5/2014 | Van Den Berg | |
| 8,758,750 B2 | 6/2014 | Weissman et al. | |
| 8,759,495 B2 | 6/2014 | Boghaert et al. | |
| 8,951,527 B2 | 2/2015 | Isenberg et al. | |
| 9,045,541 B2 | 6/2015 | Eckelman et al. | |
| 2006/0088522 A1 | 4/2006 | Boghaert et al. | |
| 2010/0173382 A1 | 7/2010 | Boghaert et al. | |
| 2013/0142786 A1 | 6/2013 | Liu et al. | |
| 2014/0065169 A1 | 3/2014 | Jaiswal et al. | |
| 2014/0140989 A1 | 5/2014 | Eckelman et al. | |
| 2014/0161825 A1 | 6/2014 | Jaiswal et al. | |
| 2014/0199308 A1 | 7/2014 | Van Den Berg | |
| 2014/0369924 A1 | 12/2014 | Weissman et al. | |

FOREIGN PATENT DOCUMENTS

| | | |
|---|---|---|
| EP | 256654 A2 | 2/1988 |
| WO | 9940940 A1 | 8/1999 |
| WO | 2004096133 A2 | 11/2004 |
| WO | 2008043072 A2 | 4/2008 |
| WO | 2009131453 A1 | 10/2009 |
| WO | 2011143624 A2 | 11/2011 |
| WO | 2014149477 A1 | 9/2014 |

OTHER PUBLICATIONS

Abcam anti-CD47 antibody [EPR4150(2)] ab108415, available at www.abcam.com/CD47-antibody-EPR41502-ab108415.html (last visited Jul. 2, 2015).*
Yamao T et al., et al., Negative regulation of platelet clearance and of the macrophage phagocytic response by the transmembrane glycoprotein SHPS-1, Journal of Biological Chemistry, vol. 277, No. 42, Issue of Oct. 18, 2002, pp. 39833-39839.
Obeid M et_al., Ecto-calreticulin in immunogenic chemotherapy, Immunological Reviews 2007, vol. 220: 22-34.
Willingham S B et al., The CD47-signal regulatory protein alpha (SIRPa) interaction is a therapeutic target for human solid tumors, PNAS, Apr. 24, 2012, vol. 109,No. 17, p. 6662-6667.
Brown et al., "Integrin-associated Protein: A 50-kD Plasma Membrane Antigen Physically and Functionally Associated with Integrins", The Journal of Cell Biology, vol. 111, Dec. 1, 1990, pp. 2785-2794.
Campbell et al., "An Ovarian Tumor Marker with Homology to Vaccinia Virus Contains an IgV-like Region and Multiple Transmembrane Domains", Cancer Research, vol. 52, Oct. 1. 1992, pp. 5416-5420.
Per-Arne Oldenborg et al., "Role of CD47 as a Marker of Self on Red Blood Cells", Science vol. 288, Jun. 16, 2000, pp. 2051-2054.
Rebres et al., "Novel CD47-Dependent Intercellular Adhesion Modulates Cell Migration", Journal of Cellular Physiology, 205:182-193 (2005).
Gardai et al., "Cell-Surface Calreticulin Initiates Clearance of Viable or Apoptotic Cells through trans-Activation of LRP on the Phagocyte", Cell, vol. 123, 321-334, Oct. 21, 2005.
Poels et al., "Monoclonal Antibody Against Human Ovarian Tumor-Associated Antigens", JNCI, vol. 76, 1986, 781-791.
Epenetos et al., "Monoclonal antibodies for imaging and therapy", Br. J. Cancer (1989), 59, 152-155.

(Continued)

*Primary Examiner* — Misook Yu
*Assistant Examiner* — Jessica H Roark
(74) *Attorney, Agent, or Firm* — Dennis A. Bennett

(57) ABSTRACT

Provided are monoclonal antibodies and antigen-binding fragments thereof that bind to, and inhibit the activity of, CD47, as well as monoclonal antibodies and antigen binding fragments thereof that compete with the former for binding to CD47. Also provided are combinations of any of the foregoing. Such antibody compounds are variously effective in 1) treating tissue ischemia and ischemia-reperfusion injury (IRI) in the setting of organ preservation and transplantation, pulmonary hypertension, sickle cell disease, myocardial infarction, stroke, and other instances of surgery and/or trauma in which IRI is a component of pathogenesis; 2) in treating autoimmune and inflammatory diseases; and 3) as anti-cancer agents that are toxic to susceptible cancer cells, promoting their phagocytic uptake and clearance, or directly killing such cells.

5 Claims, No Drawings

(56) References Cited

OTHER PUBLICATIONS

Kenemans, P., CA 125 and OA 3 as target antigens for immunodiagnosis and immunotherapy in ovarian cancer, European Journal of Obstetrics & Gynecology and Reproductive Biol&y, 36 (1990) 221-238.

van Ravenswaay Claasen et al., "Analysis of Production, Purification, and Cytolytic Potential of Bi-Specific Antibodies Reactive With Ovarian-Carcinoma-Associated Antigens and the T-Cell Antigen CD3", Int. J. Cancer: 55,128-136 (1993).

Lindberg et al., "Molecular Cloning of Integrin-associated Protein: An Immunoglobulin Family Member with Multiple Membrane-spanning Domains Implicated in C vfl3-dependent Ligand Binding", The Journal of Cell Biology, vol. 123, No. 2, Oct. 1993 485-496.

Lindberg et al., "Rh-related Antigen CD47 Is the Signal-transducer Integrin-associated Protein", The Journal of Biological Chemistry, vol. 269, No. 3, Issue of Jan. 21, pp. 1567-1570, 1994.

Mawby et al., "Isolation and characterization of CD47 glycoprotein: a multispanning membrane protein which is the same as integrin-associated protein (IAP) and the ovarian tumour marker OA3", Biochem. J. (1994) 304, 525-530.

Gresham et al., "A Novel Member of the Integrin Receptor Family Mediates Arg-Gly-Asp-stimulated Neutrophil Phagocytosis", The Journal of Cell Biology, vol. 108, May 1989 1935-1943.

Han et al., "CD47, a Ligand for the Macrophage Fusion Receptor, Participates in Macrophage Multinucleation", The Journal of Biological Chemistry, vol. 275, No. 48, Issue of Dec. 1, pp. 37984-37992, 2000.

Avent et al., "Monoclonal antibodies that recognize different membrane proteins that are deficient in Rh null, human erythrocytes", Biochem. J. (1988) 251, 499-505.

Knapp et al., "CD Antigens 1989", Blood, vol. 74, No. 4 (Sep.), 1989: pp. 1448-1450.

Ticchioni et al., "Integrin-Associated Protein (CD47) Is a Comitogenic Molecule on CD3-Activated Human T Cells", The Journal of Immunology, 1997, 158: 677-684.

Seiffert et al., "Human Signal-Regulatory Protein Is Expressed on Normal, But Not on Subsets of Leukemic Myeloid Cells and Mediates Cellular Adhesion Involving Its Counterreceptor CD47" Blood, vol. 94, No. 11 (Dec. 1), 1999: pp. 3633-3643.

Vernon-Wilson et al., "CD47 is a ligand for rat macrophage membrane signal regulatory protein SIRP (OX41) and human SIRP alpha 1", Eur. J. Immunol. 2000. 30: 2130-2137.

Latour et al., "Bidirectional Negative Regulation of Human T and Dendritic Cells by CD47 and Its Cognate Receptor Signal-Regulator Protein-alpha: Down-Regulation of IL-12 Responsiveness and Inhibition of Dendritic Cell Activation", The Journal of Immunology, 2001, 167: 2547-2554.

Subramanian et al., "Species-and cell type—specific interactions between CD47 and human SIRP-alpha", Blood, Mar. 15, 2006, vol. 107, No. 6.

Liu et al., "Signal Regulatory Protein (SIRP-alpha), a Cellular Ligand for CD47, Regulates Neutrophil Transmigration", The Journal of Biological Chemistry, vol. 277, No. 12, Issue of Mar. 22, pp. 10028-10036, 2002.

Nishiyama et al., "Overexpression of Integrin-associated Protein (CD47) in Rat Kidney Treated with a Renal Carcinogen, Ferric Nitrilotriacetate", Jpn. J. Cancer Res. 88, 120-128, Feb. 1997.

Mateo et al., "CD47 ligation induces caspase-independent cell death in chronic lymphocytic leukemia", Nature Medicine, vol. 5, No. 11, Nov. 1999, pp. 1277-1284.

Liu, A. "Differential Expression of Cell Surface Molecules in Prostate Cancer Cells", Cancer Research 60, 3429-3434, Jul. 1, 2000.

Petersen et al., "CD99 Signals Caspase-Independent T Cell Death", The Journal of Immunology, 2001, 166: 4931-4942.

Zhan et al., "Global gene expression profiling of multiple myeloma, monoclonal gammopathy of undetermined significance, and normal bone marrow plasma cells", Blood, Mar. 1, 2002 z vol. 99, No. 5.

Motegi et al., "Role of CD47-SHPS-1 system in regulation of cell migration", The EMBO Journal vol. 22, No. 11, pp. 2634-2644, 2003.

Manna et al., "CD47 Mediates Killing of Breast Tumor Cells via Gi-Dependent Inhibition of Protein Kinase A", Cancer Research 64, 1026-1036, Feb. 1, 2004.

Tamoto et al., "Gene-Expression Profile Changes Correlated with Tumor Progression and Lymph Node Metastasis in Esophageal Cancer", Clinical Cancer Research, vol. 10, 3629-3638, Jun. 1, 2004.

Kikuchi et al., "Apoptosis inducing bivalent single-chain antibody fragments against CD47 showed antitumor potency for multiple myeloma", Leukemia Research 29 (2005) 445-450.

Florian et al., "Evaluation of normal and neoplastic human mast cells for expression of CD172a (SIRP-alpha), CD47, and SHP-1", Journal of Leukocyte Biology vol. 77, Jun. 2005.

Uno et al., "Antitumor activity of a monoclonal antibody against CD47 in xenograft models of human leukemia", Oncology Reports 17: 1189-1194, 2007.

Danielsen et al., "Dysregulation of CD47 and the ligands thrombospondin 1 and 2 in multiple myeloma", British Journal of Haematology, 138, 756-760. (2007).

Pettersen et al., "CD47 Signals T Cell Death", The Journal of Immunology, 1999, 162: 7031-7040.

Lamy et al., "CD47 and the 19 kDa Interacting Protein-3 (BNIP3) in T Cell Apoptosis", The Journal of Biological Chemistry, vol. 278, No. 26, Issue of Jun. 27, pp. 23915-23921, 2003.

Manna et al., "The Mechanism of CD47-Dependent Killing of T Cells: Heterotrimeric Gi-Dependent Inhibition of Protein Kinase A", The Journal of Immunology, 2003, 170: 3544-3553.

Kikuchi et al., "A bivalent single-chain Fv fragment against CD47 induces apoptosis for leukemic cells", Biochemical and Biophysical Research Communications 315 (2004) 912-918.

Ahmed et al., "Targeting Cd47 as an Apoptotic Trigger of Human Lung Carcinoma Tumors", Amer Inst Chem Eng. 2005 mtg abstract #457d.

Sagawa et al., "A new disulfide-linked dimer of a single-chain antibody fragment against human CD47 induces apoptosis in lymphoid malignant cells via the hypoxia inducible factor-1 alpha pathway", Cancer Sci, Jun. 2011, vol. 102, No. 6, 1208-1215.

Samani et al., "The Role of the IGF System in Cancer Growth and Metastasis: Overview and Recent Insights", Endocrine Reviews 28(1):20-47, (2007).

Kaiser et al., "Expression of insulin-like growth factor receptors I and II in normal human lung and in lung cancer", J Cancer Res Clin Oncol (1993) 119:665-668.

Edris B et al. Antibody therapy targeting the CD47 protein is effective in a model of aggressive metastatic leiomyosarcoma PNAS 2012 Edris 6656-6661.

Chao MP et al. Anti-CD47 antibody synergizes with Rituximab to promote phagocytosis and eradicate non-Hodgkin lymphoma, Cell 2010 plus supplemental info.

Blazar B R et al. CD47 (integrin-associated protein) engagement of dendritic cell and macrophage counterreceptors is required to prevent the clearance of donor lymphohem cells, Journal Exp. Med., vol. 194, No. 4, Aug. 20, 2001 541-549.

Majeti R et al., CD47 is an adverse prognostic factor and therapeutic antibody target on human acute myeloid leukemia stem cells, Cell 2009,138, p. 286-299.

Jaiswal S et al., CD47 is upregulated on circulating hematopoietic stem cells and leukemia cells to avoid phagocytosis Cell, Jul. 24, 2009, 138, 271-285.

Jiang P et al., Integrin-associated Protein Is a Ligand for the P84 Neural Adhesion Molecule, The Journal of Biological Chemistry vol. 274, No. 2, Issue of Jan. 8, 1999, pp. 559-562.

Oldenborg PA et al., CD47-signal regulatory protein alpha (SIRPa) regulates Fcgamma and complement receptor-mediated phagocytosis, Journal Exp Med, vol. 193, No. 7, Apr. 2, 2001 p. 855-861.

Lindberg F P et al., Decreased resistance to bacterial infection and granulocyte defects in IAP-deficient mice, Science New Series, vol. 274, No. 5288 (Nov. 1, 1996), pp. 795-798.

Chao, et al., "The CD47-SIRP A Pathway in cancer Immune Evasion and Potential Therapeutic Implications", Current Opinion in Immunology, vol. 24, No. 2, Feb. 4, 2012, pp. 225-232.

International Search Report, PCT Application No. PCT/US2013/074766, dated Oct. 10, 2014, 6 pgs.

(56) References Cited

OTHER PUBLICATIONS

Legrand, etal., "Functional CD47/Signal Regulatory Protein Alpha (SIRP(alpha)) Interaction is Required for Optimal Human T- and Natural Killer- (NK) Cell Homeostasis in Vivo", Proceedings of the National Academy of Sciences, vol. 108, No. 32, 2001, pp. 13224-13229.

Majeti, "Monoclonal Antibody Therapy Directed Against Human Acute Myeloid Leukemia Stem Cells", Oncogene, vol. 30, No. 9, Nov. 15, 2010, pp. 1015-1016.

NCBI, Genbank Accession No. ACN59874.1, Nov. 20, 2009.

NCBI, PDB Accession No. 1A4J_L, Oct. 10, 2012.

* cited by examiner

SEQUENCE LISTING

<160> NUMBER OF SEQ ID NOS: 110

<210> SEQ ID NO 1
<211> LENGTH: 16
<212> TYPE: PRT
<213> ORGANISM: Artificial Sequence
<220> FEATURE:
<223> OTHER INFORMATION: light chain complementarity determining region

<400> SEQUENCE: 1

Arg Ser Ser Gln Ser Leu Val His Ser Asn Gly Asn Thr Tyr Leu His
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: light chain complementarity determining region

<400> SEQUENCE: 2

Lys Val Ser Tyr Arg Phe Ser

```
<210> SEQ ID NO 3
<211> LENGTH: 9
<212> TYPE: PRT
<213> ORGANISM: Artificial Sequence
<220> FEATURE:
<223> OTHER INFORMATION: light chain complementarity determining region

<400> SEQUENCE: 3

Ser Gln Asn Thr His Val Pro Arg Thr
1               5

<210> SEQ ID NO 4
<211> LENGTH: 10
<212> TYPE: PRT
<213> ORGANISM: Artificial Sequence
<220> FEATURE:
<223> OTHER INFORMATION: heavy chain complementarity determining region

<400> SEQUENCE: 4

Gly Tyr Thr Phe Thr Asn Tyr Tyr Val Phe
1               5                   10

<210> SEQ ID NO 5
<211> LENGTH: 17
<212> TYPE: PRT
<213> ORGANISM: Artificial Sequence
<220> FEATURE:
<223> OTHER INFORMATION: heavy chain complementarity determining region

<400> SEQUENCE: 5

Asp Ile Asn Pro Val Asn Gly Asp Thr Asn Phe Asn Glu Lys Phe Lys
1               5                   10                  15

Asn

<210> SEQ ID NO 6
<211> LENGTH: 7
<212> TYPE: PRT
<213> ORGANISM: Artificial Sequence
<220> FEATURE:
<223> OTHER INFORMATION: heavy chain complementarity determining region

<400> SEQUENCE: 6

Gly Gly Tyr Thr Met Asp Tyr
1               5

<210> SEQ ID NO 7
<211> LENGTH: 106
<212> TYPE: PRT
<213> ORGANISM: Artificial Sequence
<220> FEATURE:
<223> OTHER INFORMATION: light chain variable region

<400> SEQUENCE: 7

Asp Val Val Met Thr Gln Thr Pro Leu Ser Leu Ser Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
```

```
                65                  70                  75                  80
Ser Arg Val Glu Ala Glu Asp Leu Gly Val Tyr Phe Cys Ser Gln Asn
                    85                  90                  95

Thr His Val Pro Arg Thr Phe Gly Gln Gly
                100                 105

<210> SEQ ID NO 8
<211> LENGTH: 106
<212> TYPE: PRT
<213> ORGANISM: Artificial Sequence
<220> FEATURE:
<223> OTHER INFORMATION: light chain variable region

<400> SEQUENCE: 8

Asp Ile Val Met Thr Gln Thr Pro Leu Ser Leu Pro Val Thr Pro Gly
1               5                   10                  15

Glu Pro Ala Ser Ile Ser Cys Arg Ser Gln Ser Leu Val His Ser
                    20                  25                  30

Asn Gly Asn Thr Tyr Leu His Trp Tyr Gln Gln Lys Pro Gly Lys Ala
            35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                    85                  90                  95

Thr His Val Pro Arg Thr Phe Gly Gln Gly
                100                 105

<210> SEQ ID NO 9
<211> LENGTH: 106
<212> TYPE: PRT
<213> ORGANISM: Artificial Sequence
<220> FEATURE:
<223> OTHER INFORMATION: light chain variable region

<400> SEQUENCE: 9

Asp Val Val Met Thr Gln Ser Pro Leu Ser Leu Pro Val Thr Leu Gly
1               5                   10                  15

Gln Pro Ala Ser Ile Ser Cys Arg Ser Gln Ser Leu Val His Ser
                    20                  25                  30

Asn Gly Asn Thr Tyr Leu His Trp Tyr Gln Gln Lys Pro Gly Gln Ala
            35                  40                  45

Pro Arg Leu Leu Ile Tyr Lys Val Ser Tyr Arg Phe Ser Gly Val Pro
    50                  55                  60

Ser Arg Phe Ser Gly Ser Gly Ser Gly Thr Glu Phe Thr Leu Thr Ile
65                  70                  75                  80

Ser Ser Leu Gln Pro Asp Asp Phe Ala Thr Tyr Tyr Cys Ser Gln Asn
                    85                  90                  95

Thr His Val Pro Arg Thr Phe Gly Gln Gly
                100                 105

<210> SEQ ID NO 10
<211> LENGTH: 106
<212> TYPE: PRT
<213> ORGANISM: Artificial Sequence
<220> FEATURE:
<223> OTHER INFORMATION: light chain variable region

<400> SEQUENCE: 10
```

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Arg Thr Phe Gly Gln Gly
            100                 105
```

<210> SEQ ID NO 11
<211> LENGTH: 106
<212> TYPE: PRT
<213> ORGANISM: Artificial Sequence
<220> FEATURE:
<223> OTHER INFORMATION: light chain variable region

<400> SEQUENCE: 11

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Tyr Arg Phe Ser Gly Ile Pro
    50                  55                  60

Ala Arg Phe Ser Gly Ser Gly Ser Gly Thr Glu Phe Thr Leu Thr Ile
65                  70                  75                  80

Ser Ser Leu Gln Ser Glu Asp Phe Ala Val Tyr Tyr Cys Ser Gln Asn
                85                  90                  95

Thr His Val Pro Arg Thr Phe Gly Gln Gly
            100                 105
```

<210> SEQ ID NO 12
<211> LENGTH: 106
<212> TYPE: PRT
<213> ORGANISM: Artificial Sequence
<220> FEATURE:
<223> OTHER INFORMATION: light chain variable region

<400> SEQUENCE: 12

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
```

-continued

```
                85                  90                  95
Thr His Val Pro Arg Thr Phe Gly Gln Gly
            100                 105

<210> SEQ ID NO 13
<211> LENGTH: 106
<212> TYPE: PRT
<213> ORGANISM: Artificial Sequence
<220> FEATURE:
<223> OTHER INFORMATION: light chain variable region

<400> SEQUENCE: 13

Asp Ile Gln Met Thr Gln Ser Pro Ser Ser Leu Ser Ala Ser Val Gly
1               5                  10                  15

Asp Arg Val Thr Ile Thr Cys Arg Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Tyr Arg Phe Ser Gly Ile Pro
    50                  55                  60

Ala Arg Phe Ser Gly Ser Gly Ser Gly Thr Glu Phe Thr Leu Thr Ile
65                  70                  75                  80

Ser Ser Leu Gln Ser Glu Asp Phe Ala Val Tyr Tyr Cys Ser Gln Asn
                85                  90                  95

Thr His Val Pro Arg Thr Phe Gly Gln Gly
            100                 105

<210> SEQ ID NO 14
<211> LENGTH: 106
<212> TYPE: PRT
<213> ORGANISM: Artificial Sequence
<220> FEATURE:
<223> OTHER INFORMATION: light chain variable region

<400> SEQUENCE: 14

Asp Ile Val Met Thr Gln Thr Pro Leu Ser Leu Pro Val Thr Pro Gly
1               5                  10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Arg Thr Phe Gly Gln Gly
            100                 105

<210> SEQ ID NO 15
<211> LENGTH: 106
<212> TYPE: PRT
<213> ORGANISM: Artificial Sequence
<220> FEATURE:
<223> OTHER INFORMATION: light chain variable region

<400> SEQUENCE: 15

Asp Ile Val Met Thr Gln Thr Pro Leu Ser Leu Pro Val Thr Pro Gly
1               5                  10                  15
```

```
Glu Pro Ala Ser Ile Ser Cys Arg Ser Ser Gln Ser Leu Val His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Lys Val Ser Tyr Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Arg Thr Phe Gly Gln Gly
            100                 105
```

```
<210> SEQ ID NO 16
<211> LENGTH: 106
<212> TYPE: PRT
<213> ORGANISM: Artificial Sequence
<220> FEATURE:
<223> OTHER INFORMATION: light chain variable region

<400> SEQUENCE: 16

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Lys Val Ser Tyr Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Arg Thr Phe Gly Gln Gly
            100                 105
```

```
<210> SEQ ID NO 17
<211> LENGTH: 106
<212> TYPE: PRT
<213> ORGANISM: Artificial Sequence
<220> FEATURE:
<223> OTHER INFORMATION: light chain variable region

<400> SEQUENCE: 17

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Tyr Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Arg Thr Phe Gly Gln Gly
```

100             105

<210> SEQ ID NO 18
<211> LENGTH: 106
<212> TYPE: PRT
<213> ORGANISM: Artificial Sequence
<220> FEATURE:
<223> OTHER INFORMATION: light chain variable region

<400> SEQUENCE: 18

Glu Ile Val Leu Thr Gln Ser Pro Ala Thr Leu Ser Val Ser Pro Gly
1               5                   10                  15

Glu Arg Ala Thr Leu Ser Cys Arg Ser Ser Gln Ser Leu Val His Ser
            20                  25                  30

Asn Gly Asn Thr Tyr Leu His Trp Tyr Gln Gln Lys Pro Gly Gln Ala
        35                  40                  45

Pro Arg Leu Leu Ile Tyr Lys Val Ser Tyr Arg Phe Ser Gly Val Pro
    50                  55                  60

Ser Arg Phe Ser Gly Ser Gly Ser Gly Thr Asp Phe Thr Phe Thr Ile
65                  70                  75                  80

Ser Ser Leu Glu Ala Glu Asp Ala Ala Thr Tyr Tyr Cys Ser Gln Asn
                85                  90                  95

Thr His Val Pro Arg Thr Phe Gly Gln Gly
            100             105

<210> SEQ ID NO 19
<211> LENGTH: 106
<212> TYPE: PRT
<213> ORGANISM: Artificial Sequence
<220> FEATURE:
<223> OTHER INFORMATION: light chain variable region

<400> SEQUENCE: 19

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Arg Thr Phe Gly Gln Gly
            100             105

<210> SEQ ID NO 20
<211> LENGTH: 106
<212> TYPE: PRT
<213> ORGANISM: Artificial Sequence
<220> FEATURE:
<223> OTHER INFORMATION: light chain variable region

<400> SEQUENCE: 20

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

```
Asn Gly Asn Thr Tyr Leu His Trp Tyr Gln Gln Lys Pro Gly Lys Ala
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Asn
                 85                  90                  95

Thr His Val Pro Arg Thr Phe Gly Gln Gly
            100                 105

<210> SEQ ID NO 21
<211> LENGTH: 106
<212> TYPE: PRT
<213> ORGANISM: Artificial Sequence
<220> FEATURE:
<223> OTHER INFORMATION: light chain variable region

<400> SEQUENCE: 21

Asp Val Val Met Thr Gln Ser Pro Leu Ser Leu Pro Val Thr Leu Gly
 1               5                  10                  15

Gln Pro Ala Ser Ile Ser Cys Arg Ser Gln Ser Leu Val His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Asn
                 85                  90                  95

Thr His Val Pro Arg Thr Phe Gly Gln Gly
            100                 105

<210> SEQ ID NO 22
<211> LENGTH: 106
<212> TYPE: PRT
<213> ORGANISM: Artificial Sequence
<220> FEATURE:
<223> OTHER INFORMATION: light chain variable region

<400> SEQUENCE: 22

Ala Ile Gln Leu Thr Gln Ser Pro Ser Ser Leu Ser Ala Ser Val Gly
 1               5                  10                  15

Asp Arg Val Thr Ile Thr Cys Arg Ser Ser Gln Ser Leu Val His Ser
            20                  25                  30

Asn Gly Asn Thr Tyr Leu His Trp Tyr Gln Gln Lys Pro Gly Gln Ala
        35                  40                  45

Pro Arg Leu Leu Ile Tyr Lys Val Ser Tyr Arg Phe Ser Gly Val Pro
    50                  55                  60

Ser Arg Phe Ser Gly Ser Gly Ser Gly Thr Glu Phe Thr Leu Thr Ile
 65                  70                  75                  80

Ser Ser Leu Gln Pro Asp Asp Phe Ala Thr Tyr Tyr Cys Ser Gln Asn
                 85                  90                  95

Thr His Val Pro Arg Thr Phe Gly Gln Gly
            100                 105
```

<210> SEQ ID NO 23
<211> LENGTH: 106
<212> TYPE: PRT
<213> ORGANISM: Artificial Sequence
<220> FEATURE:
<223> OTHER INFORMATION: light chain variable region

<400> SEQUENCE: 23

Ala Ile Gln Leu Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Asn Thr Tyr Leu His Trp Tyr Gln Gln Lys Pro Gly Gln Ala
        35                  40                  45

Pro Arg Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Arg Thr Phe Gly Gln Gly
            100                 105

<210> SEQ ID NO 24
<211> LENGTH: 106
<212> TYPE: PRT
<213> ORGANISM: Artificial Sequence
<220> FEATURE:
<223> OTHER INFORMATION: light chain variable region

<400> SEQUENCE: 24

Ala Ile Gln Leu Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Asn Thr Tyr Leu His Trp Tyr Gln Gln Lys Pro Gly Gln Ala
        35                  40                  45

Pro Arg Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Arg Thr Phe Gly Gln Gly
            100                 105

<210> SEQ ID NO 25
<211> LENGTH: 106
<212> TYPE: PRT
<213> ORGANISM: Artificial Sequence
<220> FEATURE:
<223> OTHER INFORMATION: light chain variable region

<400> SEQUENCE: 25

Glu Ile Val Leu Thr Gln Ser Pro Ala Thr Leu Ser Val Ser Pro Gly
1               5                   10                  15

Glu Arg Ala Thr Leu Ser Cys Arg Ser Ser Gln Ser Leu Val His Ser
            20                  25                  30

Asn Gly Asn Thr Tyr Leu His Trp Tyr Gln Gln Lys Pro Gly Gln Ala
        35                  40                  45

Pro Arg Leu Leu Ile Tyr Lys Val Ser Tyr Arg Phe Ser Gly Val Pro
        50                  55                  60

Ser Arg Phe Ser Gly Ser Gly Ser Gly Thr Asp Phe Thr Phe Thr Ile
65                  70                  75                  80

Ser Ser Leu Glu Ala Glu Asp Ala Ala Thr Tyr Tyr Cys Ser Gln Asn
                85                  90                  95

Thr His Val Pro Arg Thr Phe Gly Gln Gly
            100                 105

<210> SEQ ID NO 26
<211> LENGTH: 106
<212> TYPE: PRT
<213> ORGANISM: Artificial Sequence
<220> FEATURE:
<223> OTHER INFORMATION: light chain variable region

<400> SEQUENCE: 26

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Arg Thr Phe Gly Gln Gly
            100                 105

<210> SEQ ID NO 27
<211> LENGTH: 106
<212> TYPE: PRT
<213> ORGANISM: Artificial Sequence
<220> FEATURE:
<223> OTHER INFORMATION: light chain variable region

<400> SEQUENCE: 27

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Arg Thr Phe Gly Gln Gly
            100                 105

<210> SEQ ID NO 28
<211> LENGTH: 106
<212> TYPE: PRT

<213> ORGANISM: Artificial Sequence
<220> FEATURE:
<223> OTHER INFORMATION: light chain variable region

<400> SEQUENCE: 28

```
Ala Ile Gln Leu Thr Gln Ser Pro Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Asn Thr Tyr Leu His Trp Tyr Gln Gln Lys Pro Gly Gln Ala
        35                  40                  45

Pro Arg Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Arg Thr Phe Gly Gln Gly
            100                 105
```

<210> SEQ ID NO 29
<211> LENGTH: 106
<212> TYPE: PRT
<213> ORGANISM: Artificial Sequence
<220> FEATURE:
<223> OTHER INFORMATION: light chain variable region

<400> SEQUENCE: 29

```
Glu Ile Val Leu Thr Gln Ser Pro Ala Thr Leu Ser Val Ser Pro Gly
1               5                   10                  15

Glu Arg Ala Thr Leu Ser Cys Arg Ser Ser Gln Ser Leu Val His Ser
            20                  25                  30

Asn Gly Asn Thr Tyr Leu His Trp Tyr Gln Gln Lys Pro Gly Gln Ala
        35                  40                  45

Pro Arg Leu Leu Ile Tyr Lys Val Ser Tyr Arg Phe Ser Gly Val Pro
    50                  55                  60

Ser Arg Phe Ser Gly Ser Gly Ser Gly Thr Asp Phe Thr Phe Thr Ile
65                  70                  75                  80

Ser Ser Leu Glu Ala Glu Asp Ala Ala Thr Tyr Tyr Cys Ser Gln Asn
                85                  90                  95

Thr His Val Pro Arg Thr Phe Gly Gln Gly
            100                 105
```

<210> SEQ ID NO 30
<211> LENGTH: 106
<212> TYPE: PRT
<213> ORGANISM: Artificial Sequence
<220> FEATURE:
<223> OTHER INFORMATION: light chain variable region

<400> SEQUENCE: 30

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Lys Val Ser Tyr Arg Phe Ser Gly Val Pro
    50                  55                  60
```

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Arg Thr Phe Gly Gln Gly
            100                 105

<210> SEQ ID NO 31
<211> LENGTH: 106
<212> TYPE: PRT
<213> ORGANISM: Artificial Sequence
<220> FEATURE:
<223> OTHER INFORMATION: light chain variable region

<400> SEQUENCE: 31

Ala Ile Gln Leu Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
                20                  25                  30

Asn Gly Asn Thr Tyr Leu His Trp Tyr Gln Gln Lys Pro Gly Gln Ala
            35                  40                  45

Pro Arg Leu Leu Ile Tyr Lys Val Ser Tyr Arg Phe Ser Gly Val Pro
    50                  55                  60

Ser Arg Phe Ser Gly Ser Gly Ser Gly Thr Glu Phe Thr Leu Thr Ile
65                  70                  75                  80

Ser Ser Leu Gln Pro Asp Asp Phe Ala Thr Tyr Tyr Cys Ser Gln Asn
                85                  90                  95

Thr His Val Pro Arg Thr Phe Gly Gln Gly
            100                 105

<210> SEQ ID NO 32
<211> LENGTH: 319
<212> TYPE: DNA
<213> ORGANISM: Artificial Sequence
<220> FEATURE:
<223> OTHER INFORMATION: light chain variable region

<400> SEQUENCE: 32
gatgttgtta tgacccaaac tccactctcc ctgtctgtca gtcttggaga tcaagcctcc    60
atctcttgca gatctagtca gagccttgta cacagtaatg aaacacctta tttacattgg   120
tacctgcaga agccaggcca gtctccaaag ctcctgatct acaaagtttc ctaccgattt   180
tctggggtcc cagacaggtt cagtggcagt ggatcaggga cagatttcac actcaagatc   240
agcagagtgg aggctgagga tctgggagtt tatttctgct ctcaaaatac acatgttcct   300
cggacgttcg gccaaggag                                                319

<210> SEQ ID NO 33
<211> LENGTH: 318
<212> TYPE: DNA
<213> ORGANISM: Artificial Sequence
<220> FEATURE:
<223> OTHER INFORMATION: light chain variable region

<400> SEQUENCE: 33
gatattgtga tgacccagac tccactctcc ctgcccgtca cccctggaga gccggcctcc    60
atctcctgca gatctagtca gagccttgta cacagtaatg aaacacctta tttacattgg   120
tatcagcaga aaccagggaa agctcctaag ctcctgatct ataaagtttc ctaccgattt   180

```
tctggggtcc cagacaggtt cagtggcagt gggtcaggca ctgatttcac actgaaaatc    240
agcagggtgg aggctgagga tgttggagtt tattactgtt ctcaaaatac acatgttcct    300
cggacgttcg gccaaggg                                                  318
```

<210> SEQ ID NO 34
<211> LENGTH: 318
<212> TYPE: DNA
<213> ORGANISM: Artificial Sequence
<220> FEATURE:
<223> OTHER INFORMATION: light chain variable region

<400> SEQUENCE: 34

```
gatgttgtga tgactcagtc tccactctcc ctgcccgtca cccttggaca gccggcctcc    60
atctcctgca gatctagtca gagccttgta cacagtaatg aaacaccta tttacattgg    120 taccagcaga aacctggcca ggctcccagg ctcctcatct ataaagtttc ctaccgattt    180
tctggggtcc catcaaggtt cagcggcagt ggatctggga cagaattcac tctcaccatc    240
agcagcctgc agcctgatga ttttgcaact tattactgtt ctcaaaatac acatgttcct    300
cggacgttcg gccaaggg                                                  318
```

<210> SEQ ID NO 35
<211> LENGTH: 318
<212> TYPE: DNA
<213> ORGANISM: Artificial Sequence
<220> FEATURE:
<223> OTHER INFORMATION: light chain variable region

<400> SEQUENCE: 35

```
gatgttgtga tgactcagtc tccactctcc ctgcccgtca cccttggaca gccggcctcc    60
atctcctgca gatctagtca gagccttgta cacagtaatg aaacaccta tttacattgg    120 tatcagcaga aaccagggaa agctcctaag ctcctgatct ataaagtttc ctaccgattt    180
tctggggtcc cagacaggtt cagtggcagt gggtcaggca ctgatttcac actgaaaatc    240
agcagggtgg aggctgagga tgttggagtt tattactgtt ctcaaaatac acatgttcct    300
cggacgttcg gccaaggg                                                  318
```

<210> SEQ ID NO 36
<211> LENGTH: 318
<212> TYPE: DNA
<213> ORGANISM: Artificial Sequence
<220> FEATURE:
<223> OTHER INFORMATION: light chain variable region

<400> SEQUENCE: 36

```
gacatccaga tgacccagtc tccatcctcc ctgtctgcat ctgtaggaga cagagtcacc    60
atcacttgca gatctagtca gagccttgta cacagtaatg gaaacaccta tttacattgg    120
tacctgcaga agccagggca gtctccacag ctcctgatct ataaagtttc ctaccgattt    180
tctgggatcc cagccaggtt cagtggcagt gggtctggga cagagttcac tctcaccatc    240
agcagcctgc agtctgaaga ttttgcagtt tattactgtt ctcaaaatac acatgttcct    300
cggacgttcg gccaaggg                                                  318
```

<210> SEQ ID NO 37
<211> LENGTH: 318
<212> TYPE: DNA
<213> ORGANISM: Artificial Sequence
<220> FEATURE:
<223> OTHER INFORMATION: light chain variable region

```
<400> SEQUENCE: 37
gatattgtga tgacccagac tccactctcc ctgcccgtca cccctggaga gccggcctcc      60
atctcctgca gatctagtca gagccttgta cacagtaatg gaaacaccta tttacattgg     120
tacctgcaga agccagggca gtctccacag ctcctgatct ataaagtttc ctaccgattt     180
tctggggtcc cagacaggtt cagtggcagt gggtcaggca ctgatttcac actgaaaatc     240
agcagggtgg aggctgagga tgttggagtt tattactgtt ctcaaaatac acatgttcct     300
cggacgttcg gccaaggg                                                   318

<210> SEQ ID NO 38
<211> LENGTH: 318
<212> TYPE: DNA
<213> ORGANISM: Artificial Sequence
<220> FEATURE:
<223> OTHER INFORMATION: light chain variable region

<400> SEQUENCE: 38
gacatccaga tgacccagtc tccatcctcc ctgtctgcat ctgtaggaga cagagtcacc      60
atcacttgca gatctagtca gagccttgta cacagtaatg gaaacaccta tttacattgg     120
tacctgcaga agccagggca gtctccacag ctcctgatct ataaagtttc ctaccgattt     180
tctgggatcc cagccaggtt cagtggcagt gggtctggga cagagttcac tctcaccatc     240
agcagcctgc agtctgaaga ttttgcagtt tattactgtt ctcaaaatac acatgttcct     300
cggacgttcg gccaaggg                                                   318

<210> SEQ ID NO 39
<211> LENGTH: 318
<212> TYPE: DNA
<213> ORGANISM: Artificial Sequence
<220> FEATURE:
<223> OTHER INFORMATION: light chain variable region

<400> SEQUENCE: 39
gatattgtga tgacccagac tccactctcc ctgcccgtca cccctggaga gccggcctcc      60
atctcctgca gatctagtca gagccttgta cacagtaatg gaaacaccta tttacattgg     120
tacctgcaga agccagggca gtctccacag ctcctgatct ataaagtttc ctaccgattt     180
tctggggtcc cagacaggtt cagtggcagt gggtcaggca ctgatttcac actgaaaatc     240
agcagggtgg aggctgagga tgttggagtt tattactgtt ctcaaaatac acatgttcct     300
cggacgttcg gccaaggg                                                   318

<210> SEQ ID NO 40
<211> LENGTH: 318
<212> TYPE: DNA
<213> ORGANISM: Artificial Sequence
<220> FEATURE:
<223> OTHER INFORMATION: light chain variable region

<400> SEQUENCE: 40
gatattgtga tgacccagac tccactctcc ctgcccgtca cccctggaga gccggcctcc      60
atctcctgca gatctagtca gagccttgta cacagtaatg gaaacaccta tttacattgg     120
tatcagcaga aaccaggaa agctcctaag ctcctgatct ataaagtttc ctaccgattt      180
tctggggtcc cagacaggtt cagtggcagt gggtcaggca ctgatttcac actgaaaatc     240
agcagggtgg aggctgagga tgttggagtt tattactgtt ctcaaaatac acatgttcct     300
```
cggacgttcg gccaaggg                                                    318

<210> SEQ ID NO 41
<211> LENGTH: 318
<212> TYPE: DNA
<213> ORGANISM: Artificial Sequence
<220> FEATURE:
<223> OTHER INFORMATION: light chain variable region

<400> SEQUENCE: 41
gatgttgtga tgactcagtc tccactctcc ctgcccgtca cccttggaca gccggcctcc      60
atctcctgca gatctagtca gagccttgta cacagtaatg aaacaccta tttacattgg     120
tatcagcaga accagggaa agctcctaag ctcctgatct ataaagtttc ctaccgattt     180
tctggggtcc cagacaggtt cagtggcagt gggtcaggca ctgatttcac actgaaaatc     240
agcagggtgg aggctgagga tgttggagtt tattactgtt ctcaaaatac acatgttcct     300
cggacgttcg gccaaggg                                                    318

<210> SEQ ID NO 42
<211> LENGTH: 318
<212> TYPE: DNA
<213> ORGANISM: Artificial Sequence
<220> FEATURE:
<223> OTHER INFORMATION: light chain variable region

<400> SEQUENCE: 42
gatattgtga tgacccagac tccactctcc ctgcccgtca cccctggaga gccggcctcc      60
atctcctgca gatctagtca gagccttgta cacagtaatg aaacaccta tttacattgg     120
tacctgcaga agccagggca gtctccacag ctcctgatct ataaagtttc ctaccgattt     180
tctggggtcc cagacaggtt cagtggcagt gggtcaggca ctgatttcac actgaaaatc     240
agcagggtgg aggctgagga tgttggagtt tattactgtt ctcaaaatac acatgttcct     300
cggacgttcg gccaaggg                                                    318

<210> SEQ ID NO 43
<211> LENGTH: 318
<212> TYPE: DNA
<213> ORGANISM: Artificial Sequence
<220> FEATURE:
<223> OTHER INFORMATION: light chain variable region

<400> SEQUENCE: 43
gaaattgtgt tgacacagtc tccagccacc ctgtctgtgt ctccagggga aagagccacc      60
ctctcctgca gatctagtca gagccttgta cacagtaatg aaacaccta tttacattgg     120
taccagcaga acctggcca ggctcccagg ctcctcatct ataaagtttc ctaccgattt     180
tctggggtcc cctcgaggtt cagtggcagt ggatctggga cagatttcac ctttaccatc     240
agtagcctgg aagctgaaga tgctgcaaca tattactgtt ctcaaaatac acatgttcct     300
cggacgttcg gccaaggg                                                    318

<210> SEQ ID NO 44
<211> LENGTH: 318
<212> TYPE: DNA
<213> ORGANISM: Artificial Sequence
<220> FEATURE:
<223> OTHER INFORMATION: light chain variable region

<400> SEQUENCE: 44
gatattgtga tgacccagac tccactctcc ctgcccgtca cccctggaga gccggcctcc      60

```
atctcctgca gatctagtca gagccttgta cacagtaatg aaacaccta tttacattgg      120 tatcagcaga aaccagggaa agctcctaag ctcctgatct ataaagtttc ctaccgattt      180
tctggggtcc cagacaggtt cagtggcagt gggtcaggca ctgatttcac actgaaaatc      240
agcagggtgg aggctgagga tgttggagtt tattactgtt ctcaaaatac acatgttcct      300
cggacgttcg gccaaggg                                                    318

<210> SEQ ID NO 45
<211> LENGTH: 318
<212> TYPE: DNA
<213> ORGANISM: Artificial Sequence
<220> FEATURE:
<223> OTHER INFORMATION: light chain variable region

<400> SEQUENCE: 45
gatattgtga tgacccagac tccactctcc ctgcccgtca cccctggaga gccggcctcc      60
atctcctgca gatctagtca gagccttgta cacagtaatg aaacaccta tttacattgg      120 tatcagcaga aaccagggaa agctcctaag ctcctgatct ataaagtttc ctaccgattt      180
tctggggtcc cagacaggtt cagtggcagt gggtcaggca ctgatttcac actgaaaatc      240
agcagggtgg aggctgagga tgttggagtt tattactgtt ctcaaaatac acatgttcct      300
cggacgttcg gccaaggg                                                    318

<210> SEQ ID NO 46
<211> LENGTH: 318
<212> TYPE: DNA
<213> ORGANISM: Artificial Sequence
<220> FEATURE:
<223> OTHER INFORMATION: light chain variable region

<400> SEQUENCE: 46
gatgttgtga tgactcagtc tccactctcc ctgcccgtca cccttggaca gccggcctcc      60
atctcctgca gatctagtca gagccttgta cacagtaatg aaacaccta tttacattgg      120 tatcagcaga aaccagggaa agctcctaag ctcctgatct ataaagtttc ctaccgattt      180
tctggggtcc cagacaggtt cagtggcagt gggtcaggca ctgatttcac actgaaaatc      240
agcagggtgg aggctgagga tgttggagtt tattactgtt ctcaaaatac acatgttcct      300
cggacgttcg gccaaggg                                                    318

<210> SEQ ID NO 47
<211> LENGTH: 318
<212> TYPE: DNA
<213> ORGANISM: Artificial Sequence
<220> FEATURE:
<223> OTHER INFORMATION: light chain variable region

<400> SEQUENCE: 47
gccatccagt tgacccagtc tccatcctcc ctgtctgcat ctgtaggaga cagagtcacc      60
atcacttgca gatctagtca gagccttgta cacagtaatg aaacaccta tttacattgg      120 taccagcaga aacctggcca ggctcccagg ctcctcatct ataaagtttc ctaccgattt      180
tctggggtcc catcaaggtt cagcggcagt ggatctggga cagaattcac tctcaccatc      240
agcagcctgc agcctgatga ttttgcaact tattactgtt ctcaaaatac acatgttcct      300
cggacgttcg gccaaggg                                                    318

<210> SEQ ID NO 48
```

```
<211> LENGTH: 318
<212> TYPE: DNA
<213> ORGANISM: Artificial Sequence
<220> FEATURE:
<223> OTHER INFORMATION: light chain variable region

<400> SEQUENCE: 48
gccatccagt tgacccagtc tccatcctcc ctgtctgcat ctgtaggaga cagagtcacc     60
atcacttgca gatctagtca gagccttgta cacagtaatg gaaacaccta tttacattgg    120
taccagcaga aacctggcca ggctcccagg ctcctcatct ataaagtttc ctaccgattt    180
tctggggtcc cagacaggtt cagtggcagt gggtcaggca ctgatttcac actgaaaatc    240
agcagggtgg aggctgagga tgttggagtt tattactgtt ctcaaaatac acatgttcct    300
cggacgttcg gccaaggg                                                  318

<210> SEQ ID NO 49
<211> LENGTH: 318
<212> TYPE: DNA
<213> ORGANISM: Artificial Sequence
<220> FEATURE:
<223> OTHER INFORMATION: light chain variable region

<400> SEQUENCE: 49
gccatccagt tgacccagtc tccatcctcc ctgtctgcat ctgtaggaga cagagtcacc     60
atcacttgca gatctagtca gagccttgta cacagtaatg gaaacaccta tttacattgg    120
taccagcaga aacctggcca ggctcccagg ctcctcatct ataaagtttc ctaccgattt    180
tctggggtcc cagacaggtt cagtggcagt gggtcaggca ctgatttcac actgaaaatc    240
agcagggtgg aggctgagga tgttggagtt tattactgtt ctcaaaatac acatgttcct    300
cggacgttcg gccaaggg                                                  318

<210> SEQ ID NO 50
<211> LENGTH: 318
<212> TYPE: DNA
<213> ORGANISM: Artificial Sequence
<220> FEATURE:
<223> OTHER INFORMATION: light chain variable region

<400> SEQUENCE: 50
gaaattgtgt tgacacagtc tccagccacc ctgtctgtgt ctccagggga aagagccacc     60
ctctcctgca gatctagtca gagccttgta cacagtaatg gaaacaccta tttacattgg    120
taccagcaga aacctggcca ggctcccagg ctcctcatct ataaagtttc ctaccgattt    180
tctggggtcc cctcgaggtt cagtggcagt ggatctggga cagatttcac ctttaccatc    240
agtagcctgg aagctgaaga tgctgcaaca tattactgtt ctcaaaatac acatgttcct    300
cggacgttcg gccaaggg                                                  318

<210> SEQ ID NO 51
<211> LENGTH: 318
<212> TYPE: DNA
<213> ORGANISM: Artificial Sequence
<220> FEATURE:
<223> OTHER INFORMATION: light chain variable region

<400> SEQUENCE: 51
gatgttgtga tgactcagtc tccactctcc ctgcccgtca cccttggaca gccggcctcc     60
atctcctgca gatctagtca gagccttgta cacagtaatg gaaacaccta tttacattgg    120
tatcagcaga aaccagggaa agctcctaag ctcctgatct ataaagtttc ctaccgattt    180
```
tctggggtcc cagacaggtt cagtggcagt gggtcaggca ctgatttcac actgaaaatc    240
agcagggtgg aggctgagga tgttggagtt tattactgtt ctcaaaatac acatgttcct    300
cggacgttcg gccaaggg                                                  318

<210> SEQ ID NO 52
<211> LENGTH: 318
<212> TYPE: DNA
<213> ORGANISM: Artificial Sequence
<220> FEATURE:
<223> OTHER INFORMATION: light chain variable region

<400> SEQUENCE: 52
gatattgtga tgacccagac tccactctcc ctgcccgtca cccctggaga gccggcctcc     60
atctcctgca gatctagtca gagccttgta cacagtaatg aaacaccta tttacattgg    120 tacctgcaga agccagggca gtctccacag ctcctgatct ataaagtttc ctaccgattt    180
tctggggtcc cagacaggtt cagtggcagt gggtcaggca ctgatttcac actgaaaatc    240
agcagggtgg aggctgagga tgttggagtt tattactgtt ctcaaaatac acatgttcct    300
cggacgttcg gccaaggg                                                  318

<210> SEQ ID NO 53
<211> LENGTH: 318
<212> TYPE: DNA
<213> ORGANISM: Artificial Sequence
<220> FEATURE:
<223> OTHER INFORMATION: light chain variable region

<400> SEQUENCE: 53
gccatccagt tgacccagtc tccatcctcc ctgtctgcat ctgtaggaga cagagtcacc     60
atcacttgca gatctagtca gagccttgta cacagtaatg gaaacaccta tttacattgg    120
taccagcaga aacctggcca ggctcccagg ctcctcatct ataaagtttc ctaccgattt    180
tctggggtcc cagacaggtt cagtggcagt gggtcaggca ctgatttcac actgaaaatc    240
agcagggtgg aggctgagga tgttggagtt tattactgtt ctcaaaatac acatgttcct    300
cggacgttcg gccaaggg                                                  318

<210> SEQ ID NO 54
<211> LENGTH: 318
<212> TYPE: DNA
<213> ORGANISM: Artificial Sequence
<220> FEATURE:
<223> OTHER INFORMATION: light chain variable region

<400> SEQUENCE: 54
gaaattgtgt tgacacagtc tccagccacc ctgtctgtgt ctccagggga aagagccacc     60
ctctcctgca gatctagtca gagccttgta cacagtaatg gaaacaccta tttacattgg    120
taccagcaga aacctggcca ggctcccagg ctcctcatct ataaagtttc ctaccgattt    180
tctggggtcc cctcgaggtt cagtggcagt ggatctggga cagatttcac ctttaccatc    240
agtagcctgg aagctgaaga tgctgcaaca tattactgtt ctcaaaatac acatgttcct    300
cggacgttcg gccaaggg                                                  318

<210> SEQ ID NO 55
<211> LENGTH: 318
<212> TYPE: DNA
<213> ORGANISM: Artificial Sequence
<220> FEATURE:

<223> OTHER INFORMATION: light chain variable region

<400> SEQUENCE: 55

```
gatattgtga tgacccagac tccactctcc ctgcccgtca cccctggaga gccggcctcc      60
atctcctgca gatctagtca gagccttgta cacagtaatg aaacacctta tttacattgg     120
tatcagcaga accagggaa agctcctaag ctcctgatct ataaagtttc ctaccgattt     180
tctggggtcc cagacaggtt cagtggcagt gggtcaggca ctgatttcac actgaaaatc     240
agcagggtgg aggctgagga tgttggagtt tattactgtt ctcaaaatac acatgttcct     300
cggacgttcg gccaaggg                                                    318
```

<210> SEQ ID NO 56
<211> LENGTH: 318
<212> TYPE: DNA
<213> ORGANISM: Artificial Sequence
<220> FEATURE:
<223> OTHER INFORMATION: light chain variable region

<400> SEQUENCE: 56

```
gccatccagt tgacccagtc tccatcctcc ctgtctgcat ctgtaggaga cagagtcacc      60
atcacttgca gatctagtca gagccttgta cacagtaatg aaacacctta tttacattgg     120
taccagcaga aacctggcca ggctcccagg ctcctcatct ataaagtttc ctaccgattt     180
tctggggtcc catcaaggtt cagcggcagt ggatctggga cagaattcac tctcaccatc     240
agcagcctgc agcctgatga ttttgcaact tattactgtt ctcaaaatac acatgttcct     300
cggacgttcg gccaaggg                                                    318
```

<210> SEQ ID NO 57
<211> LENGTH: 109
<212> TYPE: PRT
<213> ORGANISM: Artificial Sequence
<220> FEATURE:
<223> OTHER INFORMATION: heavy chain variable region

<400> SEQUENCE: 57

```
Glu Val Gln Leu Gln Gln Phe Gly Ala Glu Leu Val Lys Pro Gly Ala
1               5                   10                  15

Ser Met Lys Leu Ser Cys Lys Ala Ser Gly Tyr Thr Phe Thr Asn Tyr
            20                  25                  30

Tyr Val Phe Trp Val Lys Gln Arg Pro Gly Gln Gly Leu Glu Trp Ile
        35                  40                  45

Gly Asp Ile Asn Pro Val Asn Gly Asp Thr Asn Phe Asn Glu Lys Phe
    50                  55                  60

Lys Asn Lys Ala Thr Leu Thr Val Asp Lys Ser Ser Thr Thr Thr Tyr
65                  70                  75                  80

Leu Gln Leu Ser Ser Leu Thr Ser Glu Asp Ser Ala Val Tyr Tyr Cys
                85                  90                  95

Thr Arg Gly Gly Tyr Thr Met Asp Tyr Trp Gly Gln Gly
            100                 105
```

<210> SEQ ID NO 58
<211> LENGTH: 109
<212> TYPE: PRT
<213> ORGANISM: Artificial Sequence
<220> FEATURE:
<223> OTHER INFORMATION: heavy chain variable region

<400> SEQUENCE: 58

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asn Tyr
            20                  25                  30

Tyr Val Phe Trp Val Arg Gln Ala Arg Gly Gln Arg Leu Glu Trp Ile
        35                  40                  45

Gly Asp Ile Asn Pro Val Asn Gly Asp Thr Asn Phe Asn Glu Lys Phe
    50                  55                  60

Lys Asn Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Tyr Thr Met Asp Tyr Trp Gly Gln Gly
            100                 105
```

<210> SEQ ID NO 59
<211> LENGTH: 109
<212> TYPE: PRT
<213> ORGANISM: Artificial Sequence
<220> FEATURE:
<223> OTHER INFORMATION: heavy chain variable region

<400> SEQUENCE: 59

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asn Tyr
            20                  25                  30

Tyr Val Phe Trp Val Arg Gln Ala Arg Gly Gln Arg Leu Glu Trp Ile
        35                  40                  45

Gly Asp Ile Asn Pro Val Asn Gly Asp Thr Asn Phe Asn Glu Lys Phe
    50                  55                  60

Lys Asn Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Tyr Thr Met Asp Tyr Trp Gly Gln Gly
            100                 105
```

<210> SEQ ID NO 60
<211> LENGTH: 109
<212> TYPE: PRT
<213> ORGANISM: Artificial Sequence
<220> FEATURE:
<223> OTHER INFORMATION: heavy chain variable region

<400> SEQUENCE: 60

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Asn Tyr
            20                  25                  30

Tyr Val Phe Trp Val Arg Gln Ala Arg Gly Gln Arg Leu Glu Trp Ile
        35                  40                  45

Gly Asp Ile Asn Pro Val Asn Gly Asp Thr Asn Phe Asn Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Gly Gly Tyr Thr Met Asp Tyr Trp Gly Gln Gly
            100                 105

<210> SEQ ID NO 61
<211> LENGTH: 109
<212> TYPE: PRT
<213> ORGANISM: Artificial Sequence
<220> FEATURE:
<223> OTHER INFORMATION: heavy chain variable region

<400> SEQUENCE: 61

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asn Tyr
            20                  25                  30

Tyr Val Phe Trp Val Arg Gln Ala Pro Gly Lys Gly Leu Glu Trp Val
        35                  40                  45

Ser Asp Ile Asn Pro Val Asn Gly Asp Thr Asn Phe Asn Glu Lys Phe
    50                  55                  60

Lys Asn Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Tyr Thr Met Asp Tyr Trp Gly Gln Gly
            100                 105

<210> SEQ ID NO 62
<211> LENGTH: 109
<212> TYPE: PRT
<213> ORGANISM: Artificial Sequence
<220> FEATURE:
<223> OTHER INFORMATION: heavy chain variable region

<400> SEQUENCE: 62

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asn Tyr
            20                  25                  30

Tyr Val Phe Trp Val Arg Gln Ala Pro Gly Lys Gly Leu Glu Trp Val
        35                  40                  45

Ser Asp Ile Asn Pro Val Asn Gly Asp Thr Asn Phe Asn Glu Lys Phe
    50                  55                  60

Lys Asn Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Tyr Thr Met Asp Tyr Trp Gly Gln Gly
            100                 105

<210> SEQ ID NO 63
<211> LENGTH: 109
<212> TYPE: PRT
<213> ORGANISM: Artificial Sequence
<220> FEATURE:
<223> OTHER INFORMATION: heavy chain variable region

<400> SEQUENCE: 63

Gln Val Gln Leu Gln Glu Ser Gly Pro Gly Leu Val Lys Pro Ser Gln
1               5                   10                  15

```
Thr Leu Ser Leu Thr Cys Thr Val Ser Gly Tyr Thr Phe Thr Asn Tyr
            20                  25                  30

Tyr Val Phe Trp Val Arg Gln Ala Arg Gly Gln Arg Leu Glu Trp Ile
        35                  40                  45

Gly Asp Ile Asn Pro Val Asn Gly Asp Thr Asn Phe Asn Glu Lys Phe
    50                  55                  60

Lys Asn Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Gly Tyr Thr Met Asp Tyr Trp Gly Gln Gly
                100                 105
```

<210> SEQ ID NO 64
<211> LENGTH: 109
<212> TYPE: PRT
<213> ORGANISM: Artificial Sequence
<220> FEATURE:
<223> OTHER INFORMATION: heavy chain variable region

<400> SEQUENCE: 64

```
Gln Val Gln Leu Gln Glu Ser Gly Pro Gly Leu Val Lys Pro Gly Ala
1               5                   10                  15

Thr Val Lys Ile Ser Cys Lys Val Ser Gly Tyr Thr Phe Thr Asn Tyr
            20                  25                  30

Tyr Val Phe Trp Val Arg Gln Ala Arg Gly Gln Arg Leu Glu Trp Ile
        35                  40                  45

Gly Asp Ile Asn Pro Val Asn Gly Asp Thr Asn Phe Asn Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Thr Met Asp Tyr Trp Gly Gln Gly
                100                 105
```

<210> SEQ ID NO 65
<211> LENGTH: 109
<212> TYPE: PRT
<213> ORGANISM: Artificial Sequence
<220> FEATURE:
<223> OTHER INFORMATION: heavy chain variable region

<400> SEQUENCE: 65

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Tyr Thr Phe Thr Asn Tyr
            20                  25                  30

Tyr Val Phe Trp Ile Arg Gln Ser Pro Ser Arg Gly Leu Glu Trp Leu
        35                  40                  45

Gly Asp Ile Asn Pro Val Asn Gly Asp Thr Asn Phe Asn Glu Lys Phe
    50                  55                  60

Lys Asn Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Thr Met Asp Tyr Trp Gly Gln Gly
                100                 105
```

```
<210> SEQ ID NO 66
<211> LENGTH: 109
<212> TYPE: PRT
<213> ORGANISM: Artificial Sequence
<220> FEATURE:
<223> OTHER INFORMATION: heavy chain variable region

<400> SEQUENCE: 66

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asn Tyr
            20                  25                  30

Tyr Val Phe Trp Val Arg Gln Ala Arg Gly Gln Arg Leu Glu Trp Ile
        35                  40                  45

Gly Asp Ile Asn Pro Val Asn Gly Asp Thr Asn Phe Asn Glu Lys Phe
    50                  55                  60

Lys Asn Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Gly Tyr Thr Met Asp Tyr Trp Gly Gln Gly
            100                 105

<210> SEQ ID NO 67
<211> LENGTH: 109
<212> TYPE: PRT
<213> ORGANISM: Artificial Sequence
<220> FEATURE:
<223> OTHER INFORMATION: heavy chain variable region

<400> SEQUENCE: 67

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asn Tyr
            20                  25                  30

Tyr Val Phe Trp Val Arg Gln Ala Arg Gly Gln Arg Leu Glu Trp Ile
        35                  40                  45

Gly Asp Ile Asn Pro Val Asn Gly Asp Thr Asn Phe Asn Glu Lys Phe
    50                  55                  60

Lys Asn Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Gly Tyr Thr Met Asp Tyr Trp Gly Gln Gly
            100                 105

<210> SEQ ID NO 68
<211> LENGTH: 109
<212> TYPE: PRT
<213> ORGANISM: Artificial Sequence
<220> FEATURE:
<223> OTHER INFORMATION: heavy chain variable region

<400> SEQUENCE: 68

Gln Val Gln Leu Gln Glu Ser Gly Pro Gly Leu Val Lys Pro Gly Ala
1               5                   10                  15

Thr Val Lys Ile Ser Cys Lys Val Ser Gly Tyr Thr Phe Thr Asn Tyr
            20                  25                  30
```

```
Tyr Val Phe Trp Val Arg Gln Ala Arg Gly Gln Arg Leu Glu Trp Ile
         35                  40                  45

Gly Asp Ile Asn Pro Val Asn Gly Asp Thr Asn Phe Asn Glu Lys Phe
 50                  55                  60

Lys Asn Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
             85                  90                  95

Ala Arg Gly Gly Tyr Thr Met Asp Tyr Trp Gly Gln Gly
             100                 105
```

<210> SEQ ID NO 69
<211> LENGTH: 109
<212> TYPE: PRT
<213> ORGANISM: Artificial Sequence
<220> FEATURE:
<223> OTHER INFORMATION: heavy chain variable region

<400> SEQUENCE: 69

```
Gln Val Gln Leu Gln Glu Ser Gly Pro Gly Leu Val Lys Pro Gly Ala
 1               5                  10                  15

Thr Val Lys Ile Ser Cys Lys Val Ser Gly Tyr Thr Phe Thr Asn Tyr
             20                  25                  30

Tyr Val Phe Trp Val Arg Gln Ala Arg Gly Gln Arg Leu Glu Trp Ile
         35                  40                  45

Gly Asp Ile Asn Pro Val Asn Gly Asp Thr Asn Phe Asn Glu Lys Phe
 50                  55                  60

Lys Asn Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
             85                  90                  95

Ala Arg Gly Gly Tyr Thr Met Asp Tyr Trp Gly Gln Gly
             100                 105
```

<210> SEQ ID NO 70
<211> LENGTH: 109
<212> TYPE: PRT
<213> ORGANISM: Artificial Sequence
<220> FEATURE:
<223> OTHER INFORMATION: heavy chain variable region

<400> SEQUENCE: 70

```
Glu Val Gln Leu Val Gln Ser Gly Ala Glu Val Lys Lys Pro Gly Glu
 1               5                  10                  15

Ser Leu Arg Ile Ser Cys Lys Gly Ser Gly Tyr Thr Phe Thr Asn Tyr
             20                  25                  30

Tyr Val Phe Trp Ile Arg Gln Ser Pro Ser Arg Gly Leu Glu Trp Leu
         35                  40                  45

Gly Asp Ile Asn Pro Val Asn Gly Asp Thr Asn Phe Asn Glu Lys Phe
 50                  55                  60

Lys Asn Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
             85                  90                  95

Ala Arg Gly Gly Tyr Thr Met Asp Tyr Trp Gly Gln Gly
             100                 105
```

<210> SEQ ID NO 71

```
<211> LENGTH: 109
<212> TYPE: PRT
<213> ORGANISM: Artificial Sequence
<220> FEATURE:
<223> OTHER INFORMATION: heavy chain variable region

<400> SEQUENCE: 71

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asn Tyr
            20                  25                  30

Tyr Val Phe Trp Val Arg Gln Ala Arg Gly Gln Arg Leu Glu Trp Ile
        35                  40                  45

Gly Asp Ile Asn Pro Val Asn Gly Asp Thr Asn Phe Asn Glu Lys Phe
    50                  55                  60

Lys Asn Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Tyr Thr Met Asp Tyr Trp Gly Gln Gly
            100                 105

<210> SEQ ID NO 72
<211> LENGTH: 109
<212> TYPE: PRT
<213> ORGANISM: Artificial Sequence
<220> FEATURE:
<223> OTHER INFORMATION: heavy chain variable region

<400> SEQUENCE: 72

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asn Tyr
            20                  25                  30

Tyr Val Phe Trp Val Arg Gln Ala Arg Gly Gln Arg Leu Glu Trp Ile
        35                  40                  45

Gly Asp Ile Asn Pro Val Asn Gly Asp Thr Asn Phe Asn Glu Lys Phe
    50                  55                  60

Lys Asn Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Gly Tyr Thr Met Asp Tyr Trp Gly Gln Gly
            100                 105

<210> SEQ ID NO 73
<211> LENGTH: 109
<212> TYPE: PRT
<213> ORGANISM: Artificial Sequence
<220> FEATURE:
<223> OTHER INFORMATION: heavy chain variable region

<400> SEQUENCE: 73

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asn Tyr
            20                  25                  30

Tyr Val Phe Trp Val Arg Gln Ala Arg Gly Gln Arg Leu Glu Trp Ile
        35                  40                  45
```

```
Gly Asp Ile Asn Pro Val Asn Gly Asp Thr Asn Phe Asn Glu Lys Phe
    50                  55                  60

Lys Asn Arg Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gly Gly Tyr Thr Met Asp Tyr Trp Gly Gln Gly
                100                 105
```

<210> SEQ ID NO 74
<211> LENGTH: 109
<212> TYPE: PRT
<213> ORGANISM: Artificial Sequence
<220> FEATURE:
<223> OTHER INFORMATION: heavy chain variable region

<400> SEQUENCE: 74

```
Glu Val Gln Leu Val Gln Ser Gly Ala Glu Val Lys Lys Pro Gly Ala
  1               5                  10                  15

Thr Val Lys Ile Ser Cys Lys Val Ser Gly Tyr Thr Phe Thr Asn Tyr
                 20                  25                  30

Tyr Val Phe Trp Ile Arg Gln Pro Pro Gly Lys Gly Leu Glu Trp Ile
                 35                  40                  45

Gly Asp Ile Asn Pro Val Asn Gly Asp Thr Asn Phe Asn Glu Lys Phe
    50                  55                  60

Lys Asn Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Tyr Thr Met Asp Tyr Trp Gly Gln Gly
                100                 105
```

<210> SEQ ID NO 75
<211> LENGTH: 109
<212> TYPE: PRT
<213> ORGANISM: Artificial Sequence
<220> FEATURE:
<223> OTHER INFORMATION: heavy chain variable region

<400> SEQUENCE: 75

```
Glu Val Gln Leu Val Gln Ser Gly Ala Glu Val Lys Lys Pro Gly Glu
  1               5                  10                  15

Ser Leu Arg Ile Ser Cys Lys Gly Ser Gly Tyr Thr Phe Thr Asn Tyr
                 20                  25                  30

Tyr Val Phe Trp Ile Arg Gln Ser Pro Ser Arg Gly Leu Glu Trp Leu
                 35                  40                  45

Gly Asp Ile Asn Pro Val Asn Gly Asp Thr Asn Phe Asn Glu Lys Phe
    50                  55                  60

Lys Asn Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Tyr Thr Met Asp Tyr Trp Gly Gln Gly
                100                 105
```

<210> SEQ ID NO 76
<211> LENGTH: 109
<212> TYPE: PRT
<213> ORGANISM: Artificial Sequence

```
<220> FEATURE:
<223> OTHER INFORMATION: heavy chain variable region

<400> SEQUENCE: 76

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Asn Tyr
            20                  25                  30

Tyr Val Phe Trp Ile Arg Gln Ser Pro Ser Arg Gly Leu Glu Trp Leu
        35                  40                  45

Gly Asp Ile Asn Pro Val Asn Gly Asp Thr Asn Phe Asn Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Thr Met Asp Tyr Trp Gly Gln Gly
            100                 105

<210> SEQ ID NO 77
<211> LENGTH: 109
<212> TYPE: PRT
<213> ORGANISM: Artificial Sequence
<220> FEATURE:
<223> OTHER INFORMATION: heavy chain variable region

<400> SEQUENCE: 77

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Tyr Thr Phe Thr Asn Tyr
            20                  25                  30

Tyr Val Phe Trp Val Arg Gln Ala Pro Gly Gln Gly Leu Glu Trp Met
        35                  40                  45

Gly Asp Ile Asn Pro Val Asn Gly Asp Thr Asn Phe Asn Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Thr Met Asp Tyr Trp Gly Gln Gly
            100                 105

<210> SEQ ID NO 78
<211> LENGTH: 109
<212> TYPE: PRT
<213> ORGANISM: Artificial Sequence
<220> FEATURE:
<223> OTHER INFORMATION: heavy chain variable region

<400> SEQUENCE: 78

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asn Tyr
            20                  25                  30

Tyr Val Phe Trp Val Arg Gln Ala Arg Gly Gln Arg Leu Glu Trp Ile
        35                  40                  45

Gly Asp Ile Asn Pro Val Asn Gly Asp Thr Asn Phe Asn Glu Lys Phe
    50                  55                  60
```

```
Lys Asn Arg Leu Thr Ile Ser Lys Asp Thr Ser Lys Asn Gln Val Val
 65                  70                  75                  80

Leu Thr Met Thr Asn Met Asp Pro Val Asp Thr Ala Thr Tyr Tyr Cys
                 85                  90                  95

Ala Arg Gly Gly Tyr Thr Met Asp Tyr Trp Gly Gln Gly
            100                 105
```

```
<210> SEQ ID NO 79
<211> LENGTH: 109
<212> TYPE: PRT
<213> ORGANISM: Artificial Sequence
<220> FEATURE:
<223> OTHER INFORMATION: heavy chain variable region

<400> SEQUENCE: 79

Gln Val Gln Leu Gln Glu Ser Gly Pro Gly Leu Val Lys Pro Ser Gln
 1               5                  10                  15

Thr Leu Ser Leu Thr Cys Thr Val Ser Gly Tyr Thr Phe Thr Asn Tyr
                 20                  25                  30

Tyr Val Phe Trp Val Arg Gln Ala Arg Gly Gln Arg Leu Glu Trp Ile
                 35                  40                  45

Gly Asp Ile Asn Pro Val Asn Gly Asp Thr Asn Phe Asn Glu Lys Phe
 50                  55                  60

Lys Asn Arg Leu Thr Ile Ser Lys Asp Thr Ser Lys Asn Gln Val Val
 65                  70                  75                  80

Leu Thr Met Thr Asn Met Asp Pro Val Asp Thr Ala Thr Tyr Tyr Cys
                 85                  90                  95

Ala Arg Gly Gly Tyr Thr Met Asp Tyr Trp Gly Gln Gly
            100                 105
```

```
<210> SEQ ID NO 80
<211> LENGTH: 109
<212> TYPE: PRT
<213> ORGANISM: Artificial Sequence
<220> FEATURE:
<223> OTHER INFORMATION: heavy chain variable region

<400> SEQUENCE: 80

Gln Val Gln Leu Gln Glu Ser Gly Pro Gly Leu Val Lys Pro Ser Gln
 1               5                  10                  15

Thr Leu Ser Leu Thr Cys Thr Val Ser Gly Tyr Thr Phe Thr Asn Tyr
                 20                  25                  30

Tyr Val Phe Trp Val Arg Gln Ala Arg Gly Gln Arg Leu Glu Trp Ile
                 35                  40                  45

Gly Asp Ile Asn Pro Val Asn Gly Asp Thr Asn Phe Asn Glu Lys Phe
 50                  55                  60

Lys Asn Arg Leu Thr Ile Ser Lys Asp Thr Ser Lys Asn Gln Val Val
 65                  70                  75                  80

Leu Thr Met Thr Asn Met Asp Pro Val Asp Thr Ala Thr Tyr Tyr Cys
                 85                  90                  95

Ala Arg Gly Gly Tyr Thr Met Asp Tyr Trp Gly Gln Gly
            100                 105
```

```
<210> SEQ ID NO 81
<211> LENGTH: 109
<212> TYPE: PRT
<213> ORGANISM: Artificial Sequence
<220> FEATURE:
<223> OTHER INFORMATION: heavy chain variable region
```

<400> SEQUENCE: 81

Gln Val Gln Leu Gln Glu Ser Gly Pro Gly Leu Val Lys Pro Gly Ala
1               5                   10                  15

Thr Val Lys Ile Ser Cys Lys Val Ser Gly Tyr Thr Phe Thr Asn Tyr
            20                  25                  30

Tyr Val Phe Trp Val Arg Gln Ala Arg Gly Gln Arg Leu Glu Trp Ile
        35                  40                  45

Gly Asp Ile Asn Pro Val Asn Gly Asp Thr Asn Phe Asn Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Thr Met Asp Tyr Trp Gly Gln Gly
            100                 105

<210> SEQ ID NO 82
<211> LENGTH: 327
<212> TYPE: DNA
<213> ORGANISM: Artificial Sequence
<220> FEATURE:
<223> OTHER INFORMATION: heavy chain variable region

<400> SEQUENCE: 82

```
gaggtccagc tgcagcagtt tggggctgaa ctggtgaagc ctggggcttc aatgaagttg     60
tcctgcaagg cttctggcta caccttcacc aactactatg tattctgggt gaaacagagg    120
cctggacaag gccttgagtg gattggagac attaatcctg tcaatggtga tactaacttc    180
aatgagaaat tcaagaacaa ggccacactg actgtagaca gtcctccac cacaacatac     240
ttgcaactca gcagcctgac atctgaggac tctgcggtct attactgtac aagaggggt     300
tatactatgg actactgggg tcaagga                                        327
```

<210> SEQ ID NO 83
<211> LENGTH: 327
<212> TYPE: DNA
<213> ORGANISM: Artificial Sequence
<220> FEATURE:
<223> OTHER INFORMATION: heavy chain variable region

<400> SEQUENCE: 83

```
caggtgcagc tgcaggagtc gggcccagga ctggtgaagc cttcacagac cctgtccctc     60
acctgcactg tctctggcta caccttcacc aactactatg tattctgggt gcgacaggct    120
cgtggacaac gccttgagtg gataggtgac attaatcctg tcaatggtga tactaacttc    180
aatgagaaat tcaagaacag agtcaccatc tcagccgaca gtccatcag caccgcctac     240
ctgcagtgga gcagcctgaa ggcctcggac accgccatgt attactgtgc gagagggggt    300
tatactatgg actactgggg ccaggga                                        327
```

<210> SEQ ID NO 84
<211> LENGTH: 327
<212> TYPE: DNA
<213> ORGANISM: Artificial Sequence
<220> FEATURE:
<223> OTHER INFORMATION: heavy chain variable region

<400> SEQUENCE: 84

```
caggtgcagc tgcaggagtc gggcccagga ctggtgaagc cttcacagac cctgtccctc     60
```

| | |
|---|---|
| acctgcactg tctctggcta caccttcacc aactactatg tattctgggt gcgacaggct | 120 |
| cgtggacaac gccttgagtg gataggtgac attaatcctg tcaatggtga tactaacttc | 180 |
| aatgagaaat tcaagaacag agtcaccatc tcagccgaca gtccatcag caccgcctac | 240 |
| ctgcagtgga gcagcctgaa ggcctcggac accgccatgt attactgtgc gagagggggt | 300 |
| tatactatgg actactgggg ccaggga | 327 |

<210> SEQ ID NO 85
<211> LENGTH: 327
<212> TYPE: DNA
<213> ORGANISM: Artificial Sequence
<220> FEATURE:
<223> OTHER INFORMATION: heavy chain variable region

<400> SEQUENCE: 85

| | |
|---|---|
| gaagtgcagc tggtgcagtc tggagcagag gtgaaaaagc ccggggagtc tctgaggatc | 60 |
| tcctgtaagg gttctggcta caccttcacc aactactatg tattctgggt gcgacaggct | 120 |
| cgtggacaac gccttgagtg gataggtgac attaatcctg tcaatggtga tactaacttc | 180 |
| aatgagaaat tcaagaacag agtcacgatt accgcggaca atccacgag cacagcctac | 240 |
| atggagctga gcagcctgag atctgaggac acggccgtgt attactgtgc gagagggggt | 300 |
| tatactatgg actactgggg ccaggga | 327 |

<210> SEQ ID NO 86
<211> LENGTH: 327
<212> TYPE: DNA
<213> ORGANISM: Artificial Sequence
<220> FEATURE:
<223> OTHER INFORMATION: heavy chain variable region

<400> SEQUENCE: 86

| | |
|---|---|
| caggtgcagc tgcaggagtc gggcccagga ctggtgaagc cttcacagac cctgtccctc | 60 |
| acctgcactg tctctggcta caccttcacc aactactatg tattctgggt ccgccaggct | 120 |
| ccagggaagg ggctggagtg ggtcagtgac attaatcctg tcaatggtga tactaacttc | 180 |
| aatgagaaat tcaagaacag agtcaccata tcagtagaca cgtccaagaa ccagttctcc | 240 |
| ctgaagctga gctctgtgac cgccgcggac acggctgtgt attactgtgc gagagggggt | 300 |
| tatactatgg actactgggg ccaggga | 327 |

<210> SEQ ID NO 87
<211> LENGTH: 327
<212> TYPE: DNA
<213> ORGANISM: Artificial Sequence
<220> FEATURE:
<223> OTHER INFORMATION: heavy chain variable region

<400> SEQUENCE: 87

| | |
|---|---|
| caggtgcagc tgcaggagtc gggcccagga ctggtgaagc cttcacagac cctgtccctc | 60 |
| acctgcactg tctctggcta caccttcacc aactactatg tattctgggt ccgccaggct | 120 |
| ccagggaagg ggctggagtg ggtcagtgac attaatcctg tcaatggtga tactaacttc | 180 |
| aatgagaaat tcaagaacag agtcaccata tcagtagaca cgtccaagaa ccagttctcc | 240 |
| ctgaagctga gctctgtgac cgccgcggac acggctgtgt attactgtgc gagagggggt | 300 |
| tatactatgg actactgggg ccaggga | 327 |

<210> SEQ ID NO 88
<211> LENGTH: 327

```
<212> TYPE: DNA
<213> ORGANISM: Artificial Sequence
<220> FEATURE:
<223> OTHER INFORMATION: heavy chain variable region

<400> SEQUENCE: 88
caggtgcagc tgcaggagtc gggcccagga ctggtgaagc cttcacagac cctgtccctc    60
acctgcactg tctctggcta caccttcacc aactactatg tattctgggt gcgacaggct   120
cgtggacaac gccttgagtg dataggtgac attaatcctg tcaatggtga tactaacttc   180
aatgagaaat tcaagaacag actcaccatc tccaaggaca cctccaaaaa ccaggtggtc   240
cttacaatga ccaacatgga ccctgtggac acagccacgt attactgtgc aagagggggt   300
tatactatgg actactgggg ccaggga                                        327

<210> SEQ ID NO 89
<211> LENGTH: 327
<212> TYPE: DNA
<213> ORGANISM: Artificial Sequence
<220> FEATURE:
<223> OTHER INFORMATION: heavy chain variable region

<400> SEQUENCE: 89
caggtgcagc tgcaggagtc gggcccagga ctggtgaagc ctggggctac agtgaaaatc    60
tcctgcaagg tttctggcta caccttcacc aactactatg tattctgggt gcgacaggct   120
cgtggacaac gccttgagtg dataggtgac attaatcctg tcaatggtga tactaacttc   180
aatgagaaat tcaagaacag agtcacgatt accgcggaca atccacgag cacagcctac   240 atggagctga gcagcctgag atctgaggac acggccgtgt attactgtgc gagagggggt   300
tatactatgg actactgggg ccaggga                                        327

<210> SEQ ID NO 90
<211> LENGTH: 327
<212> TYPE: DNA
<213> ORGANISM: Artificial Sequence
<220> FEATURE:
<223> OTHER INFORMATION: heavy chain variable region

<400> SEQUENCE: 90
cagatcacct tgaaggagtc tggtcctacg ctggtgaaac ccacacagac cctcacgctg    60
acctgcacct tctctggcta caccttcacc aactactatg tattctggat caggcagtcc   120
ccatcgagag gccttgagtg gctgggtgac attaatcctg tcaatggtga tactaacttc   180
aatgagaaat tcaagaacag attcaccatc tccagagaca cgccaagaa ctcactgtat   240 ctgcaaatga acagcctgag agccgaggac acggctgtgt attactgtgc gagagggggt   300
tatactatgg actactgggg ccaggga                                        327

<210> SEQ ID NO 91
<211> LENGTH: 327
<212> TYPE: DNA
<213> ORGANISM: Artificial Sequence
<220> FEATURE:
<223> OTHER INFORMATION: heavy chain variable region

<400> SEQUENCE: 91
caggtgcagc tgcaggagtc gggcccagga ctggtgaagc cttcacagac cctgtccctc    60
acctgcactg tctctggcta caccttcacc aactactatg tattctgggt gcgacaggct   120
cgtggacaac gccttgagtg dataggtgac attaatcctg tcaatggtga tactaacttc   180
```

```
aatgagaaat tcaagaacag actcaccatc tccaaggaca cctccaaaaa ccaggtggtc    240
cttacaatga ccaacatgga ccctgtggac acagccacgt attactgtgc aagagggggt    300
tatactatgg actactgggg ccaggga                                        327
```

```
<210> SEQ ID NO 92
<211> LENGTH: 327
<212> TYPE: DNA
<213> ORGANISM: Artificial Sequence
<220> FEATURE:
<223> OTHER INFORMATION: heavy chain variable region

<400> SEQUENCE: 92
caggtgcagc tgcaggagtc gggcccagga ctggtgaagc cttcacagac cctgtccctc     60
acctgcactg tctctggcta caccttcacc aactactatg tattctgggt gcgacaggct    120
cgtggacaac gccttgagtg gataggtgac attaatcctg tcaatggtga tactaacttc    180
aatgagaaat tcaagaacag actcaccatc tccaaggaca cctccaaaaa ccaggtggtc    240
cttacaatga ccaacatgga ccctgtggac acagccacgt attactgtgc aagagggggt    300
tatactatgg actactgggg ccaggga                                        327
```

```
<210> SEQ ID NO 93
<211> LENGTH: 327
<212> TYPE: DNA
<213> ORGANISM: Artificial Sequence
<220> FEATURE:
<223> OTHER INFORMATION: heavy chain variable region

<400> SEQUENCE: 93
caggtgcagc tgcaggagtc gggcccagga ctggtgaagc ctggggctac agtgaaaatc     60
tcctgcaagt tttctggcta caccttcacc aactactatg tattctgggt gcgacaggct    120
cgtggacaac gccttgagtg gataggtgac attaatcctg tcaatggtga tactaacttc    180
aatgagaaat tcaagaacag agtcacgatt accgcggaca atccacgag cacagcctac    240 atggagctga gcagcctgag atctgaggac acggccgtgt attactgtgc gagaggggt     300 tatactatgg actactgggg ccaggga                                        327
```

```
<210> SEQ ID NO 94
<211> LENGTH: 327
<212> TYPE: DNA
<213> ORGANISM: Artificial Sequence
<220> FEATURE:
<223> OTHER INFORMATION: heavy chain variable region

<400> SEQUENCE: 94
caggtgcagc tgcaggagtc gggcccagga ctggtgaagc ctggggctac agtgaaaatc     60
tcctgcaagg tttctggcta caccttcacc aactactatg tattctgggt gcgacaggct    120
cgtggacaac gccttgagtg gataggtgac attaatcctg tcaatggtga tactaacttc    180
aatgagaaat tcaagaacag agtcacgatt accgcggaca atccacgag cacagcctac    240 atggagctga gcagcctgag atctgaggac acggccgtgt attactgtgc gagaggggt     300 tatactatgg actactgggg ccaggga                                        327
```

```
<210> SEQ ID NO 95
<211> LENGTH: 327
<212> TYPE: DNA
<213> ORGANISM: Artificial Sequence
<220> FEATURE:
<223> OTHER INFORMATION: heavy chain variable region
```

<400> SEQUENCE: 95

```
gaagtgcagc tggtgcagtc tggagcagag gtgaaaaagc ccggggagtc tctgaggatc    60
tcctgtaagg gttctggcta caccttcacc aactactatg tattctggat caggcagtcc   120
ccatcgagag gccttgagtg gctgggtgac attaatcctg tcaatggtga tactaacttc   180
aatgagaaat tcaagaacag agtcacgatt accgcggaca atccacgag cacagcctac    240
atggagctga gcagcctgag atctgaggac acggccgtgt attactgtgc gagagggggt   300
tatactatgg actactgggg ccaggga                                       327
```

<210> SEQ ID NO 96
<211> LENGTH: 327
<212> TYPE: DNA
<213> ORGANISM: Artificial Sequence
<220> FEATURE:
<223> OTHER INFORMATION: heavy chain variable region

<400> SEQUENCE: 96

```
caggtgcagc tgcaggagtc gggcccagga ctggtgaagc cttcacagac cctgtccctc    60
acctgcactg tctctggcta caccttcacc aactactatg tattctgggt gcgacaggct   120
cgtggacaac gccttgagtg gataggtgac attaatcctg tcaatggtga tactaacttc   180
aatgagaaat tcaagaacag agtcaccatc tcagccgaca gtccatcag caccgcctac    240
ctgcagtgga gcagcctgaa ggcctcggac accgccatgt attactgtgc gagagggggt   300
tatactatgg actactgggg ccaggga                                       327
```

<210> SEQ ID NO 97
<211> LENGTH: 327
<212> TYPE: DNA
<213> ORGANISM: Artificial Sequence
<220> FEATURE:
<223> OTHER INFORMATION: heavy chain variable region

<400> SEQUENCE: 97

```
caggtgcagc tgcaggagtc gggcccagga ctggtgaagc cttcacagac cctgtccctc    60
acctgcactg tctctggcta caccttcacc aactactatg tattctgggt gcgacaggct   120
cgtggacaac gccttgagtg gataggtgac attaatcctg tcaatggtga tactaacttc   180
aatgagaaat tcaagaacag actcaccatc tccaaggaca cctccaaaaa ccaggtggtc   240
cttacaatga ccaacatgga ccctgtggac acagccacgt attactgtgc aagagggggt   300
tatactatgg actactgggg ccaggga                                       327
```

<210> SEQ ID NO 98
<211> LENGTH: 327
<212> TYPE: DNA
<213> ORGANISM: Artificial Sequence
<220> FEATURE:
<223> OTHER INFORMATION: heavy chain variable region

<400> SEQUENCE: 98

```
caggtgcagc tgcaggagtc gggcccagga ctggtgaagc cttcacagac cctgtccctc    60
acctgcactg tctctggcta caccttcacc aactactatg tattctgggt gcgacaggct   120
cgtggacaac gccttgagtg gataggtgac attaatcctg tcaatggtga tactaacttc   180
aatgagaaat tcaagaacag agtcaccatc tcagccgaca gtccatcag caccgcctac    240
ctgcagtgga gcagcctgaa ggcctcggac accgccatgt attactgtgc gagagggggt   300
```
tatactatgg actactgggg ccaggga                                       327

<210> SEQ ID NO 99
<211> LENGTH: 327
<212> TYPE: DNA
<213> ORGANISM: Artificial Sequence
<220> FEATURE:
<223> OTHER INFORMATION: heavy chain variable region

<400> SEQUENCE: 99
gaggtccagc tggtacagtc tggggctgag gtgaagaagc ctggggctac agtgaaaatc      60
tcctgcaagg tttctggcta cccttcacc aactactatg tattctggat ccgccagccc     120
ccagggaagg ggctggagtg gattggtgac attaatcctg tcaatggtga tactaacttc     180
aatgagaaat tcaagaacag agtcacgatt accgcggaca atccacgag cacagcctac     240 atggagctga gcagcctgag atctgaggac acggccgtgt attactgtgc gagaggggt     300 tatactatgg actactgggg ccaggga                                       327

<210> SEQ ID NO 100
<211> LENGTH: 327
<212> TYPE: DNA
<213> ORGANISM: Artificial Sequence
<220> FEATURE:
<223> OTHER INFORMATION: heavy chain variable region

<400> SEQUENCE: 100
gaagtgcagc tggtgcagtc tggagcagag gtgaaaaagc ccggggagtc tctgaggatc      60
tcctgtaagg gttctggcta cccttcacc aactactatg tattctggat caggcagtcc     120
ccatcgagag gccttgagtg gctgggtgac attaatcctg tcaatggtga tactaacttc     180
aatgagaaat tcaagaacag agtcacgatt accgcggaca atccacgag cacagcctac     240 atggagctga gcagcctgag atctgaggac acggccgtgt attactgtgc gagaggggt     300 tatactatgg actactgggg ccaggga                                       327

<210> SEQ ID NO 101
<211> LENGTH: 327
<212> TYPE: DNA
<213> ORGANISM: Artificial Sequence
<220> FEATURE:
<223> OTHER INFORMATION: heavy chain variable region

<400> SEQUENCE: 101
gaagtgcagc tggtgcagtc tggagcagag gtgaaaaagc ccggggagtc tctgaggatc      60
tcctgtaagg gttctggcta cccttcacc aactactatg tattctggat caggcagtcc     120
ccatcgagag gccttgagtg gctgggtgac attaatcctg tcaatggtga tactaacttc     180
aatgagaaat tcaagaacag agtcacgatt accgcggaca atccacgag cacagcctac     240 atggagctga gcagcctgag atctgaggac acggccgtgt attactgtgc gagaggggt     300 tatactatgg actactgggg ccaggga                                       327

<210> SEQ ID NO 102
<211> LENGTH: 327
<212> TYPE: DNA
<213> ORGANISM: Artificial Sequence
<220> FEATURE:
<223> OTHER INFORMATION: heavy chain variable region

<400> SEQUENCE: 102
cagatcacct tgaaggagtc tggtcctacg ctggtgaaac ccacacagac cctcacgctg      60

```
acctgcacct tctctggcta caccttcacc aactactatg tattctgggt gcgacaggcc    120
cctggacaag ggcttgagtg gatgggtgac attaatcctg tcaatggtga tactaacttc    180
aatgagaaat tcaagaacag agtcacgatt accgcggaca atccacgag cacagcctac    240 atggagctga gcagcctgag atctgaggac acggccgtgt attactgtgc gagagggggt    300
tatactatgg actactgggg ccaggga                                        327
```

```
<210> SEQ ID NO 103
<211> LENGTH: 327
<212> TYPE: DNA
<213> ORGANISM: Artificial Sequence
<220> FEATURE:
<223> OTHER INFORMATION: heavy chain variable region

<400> SEQUENCE: 103
caggtgcagc tgcaggagtc gggcccagga ctggtgaagc cttcacagac cctgtccctc    60
acctgcactg tctctggcta caccttcacc aactactatg tattctgggt gcgacaggct    120
cgtggacaac gccttgagtg gataggtgac attaatcctg tcaatggtga tactaacttc    180
aatgagaaat tcaagaacag actcaccatc tccaaggaca cctccaaaaa ccaggtggtc    240
cttacaatga ccaacatgga ccctgtggac acagccacgt attactgtgc aagaggggggt    300 tatactatgg actactgggg ccaggga                                        327
```

```
<210> SEQ ID NO 104
<211> LENGTH: 327
<212> TYPE: DNA
<213> ORGANISM: Artificial Sequence
<220> FEATURE:
<223> OTHER INFORMATION: heavy chain variable region

<400> SEQUENCE: 104
caggtgcagc tgcaggagtc gggcccagga ctggtgaagc cttcacagac cctgtccctc    60
acctgcactg tctctggcta caccttcacc aactactatg tattctgggt gcgacaggct    120
cgtggacaac gccttgagtg gataggtgac attaatcctg tcaatggtga tactaacttc    180
aatgagaaat tcaagaacag actcaccatc tccaaggaca cctccaaaaa ccaggtggtc    240
cttacaatga ccaacatgga ccctgtggac acagccacgt attactgtgc aagagggggt    300
tatactatgg actactgggg ccaggga                                        327
```

```
<210> SEQ ID NO 105
<211> LENGTH: 327
<212> TYPE: DNA
<213> ORGANISM: Artificial Sequence
<220> FEATURE:
<223> OTHER INFORMATION: heavy chain variable region

<400> SEQUENCE: 105
caggtgcagc tgcaggagtc gggcccagga ctggtgaagc cttcacagac cctgtccctc    60
acctgcactg tctctggcta caccttcacc aactactatg tattctgggt gcgacaggct    120
cgtggacaac gccttgagtg gataggtgac attaatcctg tcaatggtga tactaacttc    180
aatgagaaat tcaagaacag actcaccatc tccaaggaca cctccaaaaa ccaggtggtc    240
cttacaatga ccaacatgga ccctgtggac acagccacgt attactgtgc aagagggggt    300
tatactatgg actactgggg ccaggga                                        327
```

```
<210> SEQ ID NO 106
```

<211> LENGTH: 327
<212> TYPE: DNA
<213> ORGANISM: Artificial Sequence
<220> FEATURE:
<223> OTHER INFORMATION: heavy chain variable region

<400> SEQUENCE: 106

```
caggtgcagc tgcaggagtc gggcccagga ctggtgaagc ctggggctac agtgaaaatc     60
tcctgcaagg tttctggcta caccttcacc aactactatg tattctgggt gcgacaggct    120
cgtggacaac gccttgagtg gataggtgac attaatcctg tcaatggtga ctactaactc    180
aatgagaaat tcaagaacag agtcacgatt accgcggaca atccacgag cacagcctac    240 atggagctga gcagcctgag atctgaggac acggccgtgt attactgtgc gagaggggt    300 tatactatgg actactgggg ccaggga                                        327
```

<210> SEQ ID NO 107
<211> LENGTH: 219
<212> TYPE: PRT
<213> ORGANISM: Artificial Sequence
<220> FEATURE:
<223> OTHER INFORMATION: complete light chain

<400> SEQUENCE: 107

```
Asp Val Val Met Thr Gln Thr Pro Leu Ser Leu Ser Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Asn
                85                  90                  95

Thr His Val Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 108
<211> LENGTH: 660
<212> TYPE: DNA
<213> ORGANISM: Artificial Sequence
<220> FEATURE:
<223> OTHER INFORMATION: complete light chain

<400> SEQUENCE: 108

```
gatgttgtta tgacccaaac tccactctcc ctgtctgtca gtcttggaga tcaagcctcc      60
atctcttgca gatctagtca gagccttgta cacagtaatg gaaacaccta tttacattgg     120
tacctgcaga agccaggcca gtctccaaag ctcctgatct acaaagtttc ctaccgattt     180
tctggggtcc cagacaggtt cagtggcagt ggatcaggga cagatttcac actcaagatc     240
agcagagtgg aggctgagga tctgggagtt tatttctgct ctcaaaatac acatgttcct     300
cggacgttcg gccaagggac caaggtggaa atcaaacgta cggtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgttga     660
```

<210> SEQ ID NO 109
<211> LENGTH: 446
<212> TYPE: PRT
<213> ORGANISM: Artificial Sequence
<220> FEATURE:
<223> OTHER INFORMATION: complete heavy chain

<400> SEQUENCE: 109

```
Glu Val Gln Leu Gln Gln Phe Gly Ala Glu Leu Val Lys Pro Gly Ala
1               5                   10                  15

Ser Met Lys Leu Ser Cys Lys Ala Ser Gly Tyr Thr Phe Thr Asn Tyr
            20                  25                  30

Tyr Val Phe Trp Val Lys Gln Arg Pro Gly Gln Gly Leu Glu Trp Ile
        35                  40                  45

Gly Asp Ile Asn Pro Val Asn Gly Asp Thr Asn Phe Asn Glu Lys Phe
    50                  55                  60

Lys Asn Lys Ala Thr Leu Thr Val Asp Lys Ser Ser Thr Thr Thr Tyr
65                  70                  75                  80

Leu Gln Leu Ser Ser Leu Thr Ser Glu Asp Ser Ala Val Tyr Tyr Cys
                85                  90                  95

Thr Arg Gly Gly Tyr Thr Met Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240
```

```
Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 110
<211> LENGTH: 1341
<212> TYPE: DNA
<213> ORGANISM: Artificial Sequence
<220> FEATURE:
<223> OTHER INFORMATION: complete heavy chain

<400> SEQUENCE: 110
gaggtccagc tgcagcagtt tggggctgaa ctggtgaagc ctggggcttc aatgaagttg      60
tcctgcaagg cttctggcta caccttcacc aactactatg tattctgggt gaaacagagg     120
cctggacaag gccttgagtg gattggagac attaatcctg tcaatggtga tactaacttc     180
aatgagaaat tcaagaacaa ggccacactg actgtagaca gtcctccac cacaacatac      240
ttgcaactca gcagcctgac atctgaggac tctgcggtct attactgtac aagaggggt      300
tatactatgg actactgggg ccagggaacg ctggtcaccg tcagctcagc ctccaccaag     360
ggcccatcgg tcttccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaactcc tggggggacc gtcagtcttc     720
ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
```

```
gtggtcagcg tcctcaccgt cctgcaccag gactggctga atggcaagga gtacaagtgc        960
aaggtcagca acaaagccct cccagccccc atcgagaaaa ccatctccaa agccaaaggg       1020
cagccccgag aaccacaggt gtacaccctg cccccatccc gggatgagct gaccaagaac       1080
caggtcagcc tgacctgcct ggtcaaaggc ttctatccca gcgacatcgc cgtggagtgg       1140
gagagcaatg ggcagccgga gaacaactac aagaccacgc ctcccgtgct ggactccgac       1200
ggctccttct tcctctacag caagctcacc gtggacaaga gcaggtggca gcagggaac       1260 gtcttctcat gctccgtgat gcatgaggct ctgcacaacc actacacgca gaagagcctc       1320
tccctgtctc cgggtaaatg a                                                 1341
```

THERAPEUTIC CD47 ANTIBODIES

The present invention relates to antibodies that bind CD47 and their use in treating conditions and disorders, such as ischemia-reperfusion injury (IRI) and cancers, mediated by this receptor.

CD47 is a cell surface receptor comprised of an extracellular IgV set domain, a 5 membrane spanning transmembrane domain, and a cytoplasmic tail that is alternatively spliced. Two ligands bind CD47: thrombospondin-1 (TSP1), and signal inhibitory receptor protein alpha (SIRPalpha). TSP1 binding to CD47 activates the heterotrimeric G protein Gi, which leads to suppression of intracellular cyclic AMP (cAMP) levels. In addition, the TSP1-CD47 pathway opposes the beneficial effects of the nitric oxide pathway in all vascular cells. The nitric oxide (NO) pathway consists of any of three enzymes (nitric oxide synthases, NOS I, NOS II and NOS III) that generate bioactive gas NO using arginine as a substrate. NO can act within the cell in which it is produced, or in neighboring cells, to activate the enzyme soluble guanylyl cyclase that produces the messenger molecule cyclic GMP (cGMP). The proper functioning of the NO-cGMP pathway is essential for protecting the cardiovascular system against stresses including, but not limited to, those resulting from wounding, inflammation, hypertension, metabolic syndrome, ischemia, and ischemia-reperfusion injury (IRI). In the context of these cellular stresses, the inhibition of the NO-cGMP pathway by the TSP1-CD47 system exacerbates the effects of stress. This is a particular problem in the cardiovascular system where both cGMP and cAMP play important protective roles. There are many cases in which ischemia and reperfusion injury cause or contribute to disease, trauma, and poor outcomes of surgical procedures.

SIRPalpha is expressed on hematopoietic cells, including macrophages and dendritic cells. When it engages CD47 on a potential phagocytic target cell, phagocytosis is slowed or prevented. The CD47-SIRPalpha interaction effectively sends a "don't eat me" signal to the phagocyte. Thus, blocking the SIRPalpha-CD47 interaction with a monoclonal antibody in this therapeutic context can provide an effective anti-cancer therapy by promoting the uptake and clearance of cancer cells by the host's immune system. This mechanism is effective in both leukemias and many types of solid tumors.

U.S. Pat. No. 8,236,313 contemplates antibodies that could be useful in the field of ischemia and blood flow to reverse and/or prevent tissue ischemia and related and associated tissue and cell damage, including antibodies that block CD47. No antibodies are actually disclosed.

U.S. Pat. No. 8,101,719 discloses humanized antibodies that bind to CD47 for use in treating hematological disorders. Objects of the invention include humanized anti-CD47 antibodies and small antibody fragments exhibiting reduced antigenicity while retaining their CD47 binding activity and apoptosis-inducing activity. Such antibodies and small fragments are contemplated for use in treating hematological disorders such as various types of leukemias, malignant lymphoma, aplastic anemia, myeodysplastic syndromes, and polycythemia vera. No other properties of these antibodies are disclosed.

PCT International Publication WO 2011/143624 discloses chimeric and humanized anti-CD47 monoclonal antibodies for use as reagents for the diagnosis and immunotherapy of diseases associated with CD47 in humans, particularly in cancer therapy, for example to increase phagocytosis of cancer cells expressing CD47. Preferred antibodies are non-activating, i.e., block ligand binding, but do not signal. Disclosed humanized B6H12 and 5F9 antibodies bound soluble human CD47; B6H12 also bound human CD47 on the surface of human CD47-transfected YB2/0 cells. Humanized B6H12 and 5F9 antibodies enabled phagocytosis of CFSE-labeled HL-60 cells by mouse bone marrow- or peripheral blood-derived macrophages in vitro, respectively. Humanized B6H12 utilized human VH-3-7 and VK3-11 frameworks.

There exists a need for antibodies to human CD47 that selectively block the binding of TSP1 to CD47 to promote the beneficial effects of nitric oxide-cGMP signaling and cAMP signaling in the cardiovascular system in settings in which IRI plays a role in pathogenesis. These situations/diseases include organ transplantation, acute kidney injury, cardiopulmonary bypass surgery, pulmonary hypertension, sickle cell disease, myocardial infarction, stroke, surgical resections and reconstructive surgery, reattachment of digits/body parts, skin grafting, and trauma. There is also a need for antibodies that block the binding of SIRPalpha to CD47, thus providing novel anti-cancer therapies. Such antibodies that also have the ability to selectively kill transformed or cancer cells are also expected to provide additional therapeutic benefit.

Antibody compounds of the present invention meet these needs. They bind to epitopes in the extracellular IgV domain of CD47, inhibiting TSP1 and SIRPalpha binding to CD47 and receptor activation, while inducing little or no agonist activity. Certain other antibodies of the present invention also provide a tumor-toxic effect that is specific to activated or transformed cells in addition to promoting tumor cell phagocytic clearance. In view of these properties, antibody compounds of the present invention should be therapeutically useful in treating many forms of IRI and both blood cancers and solid tumors.

In addition, the present antibody compounds possess a number of other desirable properties, including broad reactivity with CD47 of a wide variety of mammalian species, including that of human, mouse, rat, and pig, making these antibodies useful in both human and veterinary medicine. This feature is further advantageous in that it facilitates preclinical studies including, but not limited to, safety and efficacy studies, in a variety of mammalian species, and therefore the development of such antibodies as human and veterinary therapeutics.

Accordingly, the present invention provides:

Embodiment 1. A monoclonal antibody, or antigen-binding fragment thereof, that specifically binds human, rat, mouse, and pig CD47.

Embodiment 2. The monoclonal antibody or antigen-binding fragment thereof of Embodiment 1, which is chimeric or humanized.

Embodiment 3. The monoclonal antibody, or antigen-binding fragment thereof, of embodiment 1 or embodiment 2, which comprises three light chain complementarity determining regions (LCDRs 1-3) and three heavy chain complementarity determining regions (HCDRs 1-3), wherein:

LCDR 1 comprises the amino acid sequence RSSQSLVHSNGNTYLH (SEQ ID NO:1) LCDR 2 comprises the amino acid sequence KVSYRFS (SEQ ID NO:2); and LCDR 3 comprises the amino acid sequence SQNTHVPRT (SEQ ID NO:3);

HCDR1 comprises the amino acid sequence GYTFTNYYVF (SEQ ID NO:4);

HCDR 2 comprises the amino acid sequence DINPVNGDTNFNEKFKN (SEQ ID NO:5); and

HCDR 3 comprises the amino acid sequence GGYTMDY (SEQ ID NO:6).

Embodiment 4. The monoclonal antibody, or antigen-binding fragment thereof, of any one of embodiment 1-embodiment 3, which comprises a light chain variable region (LCVR) and a heavy chain variable region (HCVR), wherein said LCVR and said HCVR comprise, respectively, amino acid sequences selected from the group consisting of:
SEQ ID NO:7 and SEQ ID NO:57;
SEQ ID NO:8 and SEQ ID NO:58;
SEQ ID NO:9 and SEQ ID NO:59;
SEQ ID NO:10 and SEQ ID NO:60;
SEQ ID NO:11 and SEQ ID NO:61;
SEQ ID NO:12 and SEQ ID NO:62;
SEQ ID NO:13 and SEQ ID NO:63;
SEQ ID NO:14 and SEQ ID NO:64;
SEQ ID NO:15 and SEQ ID NO:65;
SEQ ID NO:16 and SEQ ID NO:66;
SEQ ID NO:17 and SEQ ID NO:67;
SEQ ID NO:18 and SEQ ID NO:68;
SEQ ID NO:19 and SEQ ID NO:69;
SEQ ID NO:20 and SEQ ID NO:70;
SEQ ID NO:21 and SEQ ID NO:71;
SEQ ID NO:22 and SEQ ID NO:72;
SEQ ID NO:23 and SEQ ID NO:73;
SEQ ID NO:24 and SEQ ID NO:74;
SEQ ID NO:25 and SEQ ID NO:75;
SEQ ID NO:26 and SEQ ID NO:76;
SEQ ID NO:27 and SEQ ID NO:77;
SEQ ID NO:28 and SEQ ID NO:78;
SEQ ID NO:29 and SEQ ID NO:79;
SEQ ID NO:30 and SEQ ID NO:80; and
SEQ ID NO:31 and SEQ ID NO:81.

Embodiment 5. A monoclonal antibody, or antigen-binding fragment thereof, which comprises a light chain variable region (LCVR) and a heavy chain variable region (HCVR), wherein said LCVR and said HCVR comprise, respectively, amino acid sequences selected from the group consisting of
SEQ ID NO:7 and SEQ ID NO:57;
SEQ ID NO:8 and SEQ ID NO:58;
SEQ ID NO:11 and SEQ ID NO:61;
SEQ ID NO:14 and SEQ ID NO:64;
SEQ ID NO:16 and SEQ ID NO:66;
SEQ ID NO:18 and SEQ ID NO:68;
SEQ ID NO:19 and SEQ ID NO:69;
SEQ ID NO:25 and SEQ ID NO:75;
SEQ ID NO:27 and SEQ ID NO:77;
SEQ ID NO:28 and SEQ ID NO:78;
SEQ ID NO:29 and SEQ ID NO:79;
SEQ ID NO:30 and SEQ ID NO:80; and
SEQ ID NO:31 and SEQ ID NO:81.

Embodiment 6. A monoclonal antibody, or antigen-binding fragment thereof, which comprises a light chain variable region (LCVR) and a heavy chain variable region (HCVR), wherein said LCVR and said HCVR comprise, respectively, amino acid sequences selected from the group consisting of
SEQ ID NO:9 and SEQ ID NO:59;
SEQ ID NO:10 and SEQ ID NO:60;
SEQ ID NO:12 and SEQ ID NO:62;
SEQ ID NO:13 and SEQ ID NO:63;
SEQ ID NO:15 and SEQ ID NO:65;
SEQ ID NO:17 and SEQ ID NO:67;
SEQ ID NO:20 and SEQ ID NO:70;
SEQ ID NO:21 and SEQ ID NO:71;
SEQ ID NO:22 and SEQ ID NO:72;
SEQ ID NO:23 and SEQ ID NO:73;
SEQ ID NO:24 and SEQ ID NO:74; and
SEQ ID NO:26 and SEQ ID NO:76.

Embodiment 7. A monoclonal antibody, or antigen-binding fragment thereof, that competes with said monoclonal antibody or antigen-binding fragment thereof of any one of embodiment 1-embodiment 6 for binding to CD47.

Embodiment 8. A pharmaceutical composition, comprising said monoclonal antibody, or antigen-binding fragment thereof, of any one of embodiment 1-embodiment 7, and a pharmaceutically or physiologically acceptable carrier, diluent, or excipient.

Embodiment 9. A monoclonal antibody, or antigen-binding fragment thereof, of any one of claims embodiment 1-embodiment 7 for use in human therapy or therapy of companion/pet animals, working animals, sport animals, zoo animals, or therapy of other valuable animals kept in captivity.

Embodiment 10. The monoclonal antibody, or antigen-binding fragment thereof, of any one of embodiment 1-embodiment 7 for use in treating ischemia-reperfusion injury, or an autoimmune or inflammatory disease, in a human or companion/pet animal, working animal, sport animal, zoo animal, or other valuable animal kept in captivity.

Embodiment 11. The monoclonal antibody, or antigen-binding fragment thereof, of embodiment 10, which comprises a light chain variable region (LCVR) and a heavy chain variable region (HCVR), wherein said LCVR and said HCVR comprise, respectively, amino acid sequences selected from the group consisting of:
SEQ ID NO:7 and SEQ ID NO:57;
SEQ ID NO:8 and SEQ ID NO:58;
SEQ ID NO:11 and SEQ ID NO:61;
SEQ ID NO:14 and SEQ ID NO:64;
SEQ ID NO:16 and SEQ ID NO:66;
SEQ ID NO:18 and SEQ ID NO:68;
SEQ ID NO:19 and SEQ ID NO:69;
SEQ ID NO:25 and SEQ ID NO:75;
SEQ ID NO:27 and SEQ ID NO:77;
SEQ ID NO:28 and SEQ ID NO:78;
SEQ ID NO:29 and SEQ ID NO:79;
SEQ ID NO:30 and SEQ ID NO:80; and
SEQ ID NO:31 and SEQ ID NO:81.

Embodiment 12. The monoclonal antibody, or antigen-binding fragment thereof, of embodiment 10 or embodiment 11, wherein said ischemia-reperfusion injury occurs in organ transplantation, acute kidney injury, cardiopulmonary bypass surgery, pulmonary hypertension, sickle cell disease, myocardial infarction, stroke, surgical resections and reconstructive surgery, reattachment of an appendage or other body part, skin grafting, or trauma.

Embodiment 13. The monoclonal antibody, or antigen-binding fragment thereof, of embodiment 10 or embodiment 11, wherein said autoimmune or inflammatory disease is selected from the group consisting of arthritis, multiple sclerosis, psoriasis, Crohn's disease, inflammatory bowel disease, lupus, Grave's disease and Hashimoto's thyroiditis, and ankylosing spondylitis.

Embodiment 14. The monoclonal antibody, or antigen-binding fragment thereof, of any one of embodiment 1-embodiment 7 for use in treating a susceptible cancer.

Embodiment 15. The monoclonal antibody, or antigen-binding fragment thereof, of embodiment 14, which comprises a light chain variable region (LCVR) and a heavy chain variable region (HCVR), wherein said LCVR and said HCVR comprise, respectively, amino acid sequences selected from the group consisting of:
SEQ ID NO:9 and SEQ ID NO:59;
SEQ ID NO:10 and SEQ ID NO:60;
SEQ ID NO:12 and SEQ ID NO:62;
SEQ ID NO:13 and SEQ ID NO:63;
SEQ ID NO:15 and SEQ ID NO:65;
SEQ ID NO:17 and SEQ ID NO:67;
SEQ ID NO:20 and SEQ ID NO:70;
SEQ ID NO:21 and SEQ ID NO:71;
SEQ ID NO:22 and SEQ ID NO:72;
SEQ ID NO:23 and SEQ ID NO:73;
SEQ ID NO:24 and SEQ ID NO:74; and
SEQ ID NO:26 and SEQ ID NO:76.

Embodiment 16. The monoclonal antibody, or antigen binding fragment thereof, of embodiment 14 or embodiment 15, which promotes phagocytosis and/or killing of cells of said susceptible cancer.

Embodiment 17. The monoclonal antibody, or antigen binding fragment thereof, of any one of embodiment 14-embodiment 16, wherein said susceptible cancer is selected from the group consisting of a leukemia, a lymphoma, ovarian cancer, breast cancer, endometrial cancer, colon cancer, rectal cancer, bladder cancer, lung cancer, bronchial cancer, bone cancer, prostate cancer, pancreatic cancer, liver and bile duct cancer, esophageal cancer, renal cancer, thyroid cancer, head and neck cancer, testicular cancer, glioblastoma, astrocytoma, melanoma, and leiomyosarcoma.

Embodiment 18. The monoclonal antibody, or antigen binding fragment thereof, of embodiment 17, wherein said leukemia is selected from the group consisting of acute lymphocytic (lymphoblastic) leukemia, acute myeloid leukemia, chronic lymphocytic leukemia, multiple myeloma, and chronic myeloid leukemia.

Embodiment 19. Use of said monoclonal antibody, or antigen-binding fragment thereof, of any one of embodiment 1-embodiment 7 to treat ischemia-reperfusion injury, or an autoimmune or inflammatory disease, in a human or companion/pet animal, working animal, sport animal, zoo animal, or other valuable animal kept in captivity.

Embodiment 20. The use of embodiment 19, wherein said monoclonal antibody, or antigen binding fragment thereof, comprises a light chain variable region (LCVR) and a heavy chain variable region (HCVR), wherein said LCVR and said HCVR comprise, respectively, amino acid sequences selected from the group consisting of:
SEQ ID NO:7 and SEQ ID NO:57;
SEQ ID NO:8 and SEQ ID NO:58;
SEQ ID NO:11 and SEQ ID NO:61;
SEQ ID NO:14 and SEQ ID NO:64;
SEQ ID NO:16 and SEQ ID NO:66;
SEQ ID NO:18 and SEQ ID NO:68;
SEQ ID NO:19 and SEQ ID NO:69;
SEQ ID NO:25 and SEQ ID NO:75;
SEQ ID NO:27 and SEQ ID NO:77;
SEQ ID NO:28 and SEQ ID NO:78;
SEQ ID NO:29 and SEQ ID NO:79;
SEQ ID NO:30 and SEQ ID NO:80; and
SEQ ID NO:31 and SEQ ID NO:81.

Embodiment 21. Use of said monoclonal antibody, or antigen-binding fragment thereof, of any one of embodiment 1-embodiment 7 to treat a susceptible cancer.

Embodiment 22. The use of embodiment 21, wherein said monoclonal antibody, or antigen binding fragment thereof, comprises a light chain variable region (LCVR) and a heavy chain variable region (HCVR), wherein said LCVR and said HCVR comprise, respectively, amino acid sequences selected from the group consisting of:
SEQ ID NO:9 and SEQ ID NO:59;
SEQ ID NO:10 and SEQ ID NO:60;
SEQ ID NO:12 and SEQ ID NO:62;
SEQ ID NO:13 and SEQ ID NO:63;
SEQ ID NO:15 and SEQ ID NO:65;
SEQ ID NO:17 and SEQ ID NO:67;
SEQ ID NO:20 and SEQ ID NO:70;
SEQ ID NO:21 and SEQ ID NO:71;
SEQ ID NO:22 and SEQ ID NO:72;
SEQ ID NO:23 and SEQ ID NO:73;
SEQ ID NO:24 and SEQ ID NO:74; and
SEQ ID NO:26 and SEQ ID NO:76.

Embodiment 23. Use of said monoclonal antibody, or antigen-binding fragment thereof, of any one of embodiment 1-embodiment 7 for the manufacture of a medicament to treat ischemia-reperfusion injury, or an autoimmune or inflammatory disease, in a human or companion/pet animal, working animal, sport animal, zoo animal, or other valuable animal kept in captivity.

Embodiment 24. The use of embodiment 23, wherein said monoclonal antibody, or antigen binding fragment thereof, comprises a light chain variable region (LCVR) and a heavy chain variable region (HCVR), wherein said LCVR and said HCVR comprise, respectively, amino acid sequences selected from the group consisting of:
SEQ ID NO:7 and SEQ ID NO:57;
SEQ ID NO:8 and SEQ ID NO:58;
SEQ ID NO:11 and SEQ ID NO:61;
SEQ ID NO:14 and SEQ ID NO:64;
SEQ ID NO:16 and SEQ ID NO:66;
SEQ ID NO:18 and SEQ ID NO:68;
SEQ ID NO:19 and SEQ ID NO:69;
SEQ ID NO:25 and SEQ ID NO:75;
SEQ ID NO:27 and SEQ ID NO:77;
SEQ ID NO:28 and SEQ ID NO:78;
SEQ ID NO:29 and SEQ ID NO:79;
SEQ ID NO:30 and SEQ ID NO:80; and
SEQ ID NO:31 and SEQ ID NO:81.

Embodiment 25. The use of embodiment 23 or embodiment 24, wherein said ischemia-reperfusion injury occurs in organ transplantation, acute kidney injury, cardiopulmonary bypass surgery, pulmonary hypertension, sickle cell disease, myocardial infarction, stroke, surgical resections and reconstructive surgery, reattachment of an appendage or other body part, skin grafting, and trauma.

Embodiment 26. The use of embodiment 23 or embodiment 24, wherein said autoimmune or inflammatory disease is selected from the group consisting of arthritis, multiple sclerosis, psoriasis, Crohn's disease, inflammatory bowel disease, lupus, Grave's disease and Hashimoto's thyroiditis, and ankylosing spondylitis.

Embodiment 27. Use of said monoclonal antibody, or antigen-binding fragment thereof, of any one of embodiment 1-embodiment 7 for the manufacture of a medicament to treat a susceptible cancer.

Embodiment 28. The use of embodiment 27, wherein said monoclonal antibody, or antigen-binding fragment thereof, comprises a light chain variable region (LCVR) and a heavy chain variable region (HCVR), wherein said LCVR and said HCVR comprise, respectively, amino acid sequences selected from the group consisting of:
SEQ ID NO:9 and SEQ ID NO:59;
SEQ ID NO:10 and SEQ ID NO:60;

SEQ ID NO:12 and SEQ ID NO:62;
SEQ ID NO:13 and SEQ ID NO:63;
SEQ ID NO:15 and SEQ ID NO:65;
SEQ ID NO:17 and SEQ ID NO:67;
SEQ ID NO:20 and SEQ ID NO:70;
SEQ ID NO:21 and SEQ ID NO:71;
SEQ ID NO:22 and SEQ ID NO:72;
SEQ ID NO:23 and SEQ ID NO:73;
SEQ ID NO:24 and SEQ ID NO:74; and
SEQ ID NO:26 and SEQ ID NO:76.

Embodiment 29. A method of treating ischemia or ischemia-reperfusion injury in a patient in need thereof, comprising administering to said patient an effective amount of said monoclonal antibody, or antigen-binding fragment thereof, of any one of embodiment 1-embodiment 7, or a monoclonal antibody, or antigen-binding fragment thereof, that competes with said monoclonal antibody or antigen-binding fragment thereof of any one of embodiment 1-embodiment 7 for binding to CD47.

Embodiment 30. The method of embodiment 29, wherein said patient is about to be subjected to, or is experiencing, ischemia or ischemia-reperfusion injury.

Embodiment 31. The method of embodiment 29 or embodiment 30, wherein said patient is a human.

Embodiment 32. The method of embodiment 29 or embodiment 30, wherein said patient is a companion/pet animal, working animal, sport animal, zoo animal, or other valuable animal kept in captivity.

Embodiment 33. The method of any one of embodiment 29-embodiment 32, wherein said ischemia occurs because said patient will undergo, or is undergoing, a surgery selected from the group consisting of integument surgery, soft tissue surgery, composite tissue surgery, cosmetic surgery, surgical resections, reconstructive surgery, skin graft surgery, and limb reattachment surgery.

Embodiment 34. The method of embodiment 33, wherein said skin graft is an autograft.

Embodiment 35. The method of any one of embodiment 29-32, wherein said ischemia occurs because said patient will undergo, or is undergoing, organ transplant surgery.

Embodiment 36. The method of any one of embodiment 29-embodiment 32, wherein said ischemia-reperfusion injury occurs in organ transplantation, acute kidney injury, cardiopulmonary bypass surgery, pulmonary hypertension, sickle cell disease, myocardial infarction, stroke, surgical resection, reconstructive surgery, reattachment of an appendage or other body part, or skin grafting.

Embodiment 37. The method of any one of embodiment 29-embodiment 36, wherein said monoclonal antibody, antigen-binding fragment thereof, or competing monoclonal antibody or antigen binding fragment thereof, is administered before, during, or after said subject undergoes ischemia or surgery, or a combination of any of these time periods.

Embodiment 38. The method of any one of embodiment 29-embodiment 37, further comprising administering to said patient an effective amount of a nitric oxide donor, precursor, or both.

Embodiment 39. The method of embodiment 38, wherein said nitric oxide donor or precursor is selected from the group consisting of NO gas, isosorbide dinitrite, nitrite, nitroprusside, nitroglycerin, 3-Morpholinosydnonimine (SIN-1), S-nitroso-N-acetylpenicillamine (SNAP), Diethylenetriamine/NO (DETACNO), S-nitrosothiols, and arginine.

Embodiment 40. A method of increasing tissue perfusion in a subject in need thereof, comprising administering to said subject an effective amount of a monoclonal antibody, or antigen-binding fragment thereof, of any one of embodiment 1-embodiment 7, or a monoclonal antibody, or antigen-binding fragment thereof, that competes with said monoclonal antibody or antigen-binding fragment thereof of any one of embodiment 1-embodiment 7 for binding to CD47.

Embodiment 41. The method of embodiment 40, wherein said subject has, or is at risk of developing, at least one disease or condition selected from the group consisting of ischemia-reperfusion injury, myocardial infarction, myocardial ischemia, stroke, cerebral ischemia, sickle cell anemia, and pulmonary hypertension.

Embodiment 42. The method of embodiment 40, wherein said subject has, or is at risk of developing, at least one disease or condition selected from the group consisting of hypertension, atherosclerosis, vasculopathy, ischemia secondary to diabetes, and peripheral vascular disease.

Embodiment 43. The method of embodiment 40, wherein the need for increased tissue perfusion arises because said subject has had, is having, or will have, a surgery selected from the group consisting of integument surgery, soft tissue surgery, composite tissue surgery, skin graft surgery, resection of a solid organ, and reattachment or an appendage or other body part.

Embodiment 44. The method of embodiment 43, wherein said skin graft is an autograft.

Embodiment 45. The method of embodiment 40, wherein the need for increased tissue perfusion arises because said subject has had, is having, or will have, organ transplant surgery.

Embodiment 46. The method of any one of embodiment 40-embodiment 45, further comprising administering to said subject an effective amount of a nitric oxide donor, precursor, or both.

Embodiment 47. The method of embodiment 46, wherein said nitric oxide donor or precursor is selected from the group consisting of NO gas, isosorbide dinitrite, nitrite, nitroprusside, nitroglycerin, 3-Morpholinosydnonimine (SIN-1), S-nitroso-N-acetylpenicillamine (SNAP), Diethylenetriamine/NO (DETA/NO), S-nitrosothiols, and arginine.

Embodiment 48. A method of transplanting a donor organ from an organ donor to an organ recipient, comprising any single step, any combination of steps, or all steps selected from the group consisting of steps i)-iii):
i) administering to said organ donor prior to, during, both prior to and during, after, or any combination thereof, donation of said donor organ an effective amount of said monoclonal antibody or antigen-binding fragment thereof of any one of embodiment 1-embodiment 7, and/or a monoclonal antibody, or antigen-binding fragment thereof, that competes with said monoclonal antibody or antigen-binding fragment thereof of any one of embodiment 1-embodiment 7 for binding to CD47;
ii) contacting said donor organ prior to, during, both prior to and during, after, or any combination thereof, transplantation to said organ recipient, and an effective amount of said monoclonal antibody or antigen-binding fragment thereof of any one of embodiment 1-embodiment 7, and/or a monoclonal antibody, or antigen-binding fragment thereof, that competes with said monoclonal antibody or antigen-binding fragment thereof of any one of embodiment 1-embodiment 7 for binding to CD47; and iii) administering to said organ recipient prior to, during, both prior to and during, after, or any combination thereof, transplantation of said donor organ to said organ recipient, an effective amount of said monoclonal antibody or antigen-binding fragment thereof of any one of embodiment 1-embodiment 7, and/or a monoclonal antibody, or antigen-binding fragment thereof, that competes with said monoclonal antibody or antigen-binding fragment thereof of any one of embodiment 1-embodiment 7 for binding to CD47.

Embodiment 49. The method of embodiment 48, wherein said monoclonal antibody or antigen-binding fragment thereof of any one of embodiment 1-embodiment 7, or monoclonal antibody, or antigen-binding fragment thereof, that competes with said monoclonal antibody or antigen-binding fragment thereof of any one of embodiment 1-embodiment 7 for binding to CD47, reduces ischemia reperfusion injury in said donor organ.

Embodiment 50. The method of embodiment 48 or embodiment 49, further comprising administering to said organ donor, said donor organ, said organ recipient, or any combination thereof, an effective amount of a nitric oxide donor, precursor, or both.

Embodiment 51. The method of embodiment 50, wherein said nitric oxide donor or precursor is selected from the group consisting of NO gas, isosorbide dinitrite, nitrite, nitroprusside, nitroglycerin, 3-Morpholinosydnonimine (SIN-1), S-nitroso-N-acetylpenicillamine (SNAP), Diethylenetriamine/NO (DETA/NO), S-nitrosothiols, and arginine.

Embodiment 52. A method of treating an autoimmune or inflammatory disease in a patient in need thereof, comprising administering to said patient an effective amount of said monoclonal antibody, or antigen-binding fragment thereof, of any one of embodiment 1-embodiment 7, or a monoclonal antibody, or antigen-binding fragment thereof, that competes with said monoclonal antibody or antigen-binding fragment thereof of any one of [1]-[7] for binding to CD47.

Embodiment 53. The method of embodiment 52, wherein said autoimmune or inflammatory disease is selected from the group consisting of arthritis, multiple sclerosis, psoriasis, Crohn's disease, inflammatory bowel disease, lupus, Grave's disease and Hashimoto's thyroiditis, and ankylosing spondylitis.

Embodiment 54. The method of embodiment 52 or embodiment 53, wherein said patient is a human.

Embodiment 55. The method of embodiment 52 or embodiment 53, wherein said patient is a companion/pet animal, working animal, sport animal, zoo animal, or other valuable animal kept in captivity.

Embodiment 56. The method of any one of embodiment 52-embodiment 55, further comprising administering to said patient an effective amount of a nitric oxide donor, precursor, or both.

Embodiment 57. The method of embodiment 56, wherein said nitric oxide donor or precursor is selected from the group consisting of NO gas, isosorbide dinitrite, nitrite, nitroprusside, nitroglycerin, 3-Morpholinosydnonimine (SIN-1), S-nitroso-N-acetylpenicillamine (SNAP), Diethylenetriamine/NO (DETA/NO), S-nitrosothiols, and arginine.

Embodiment 58. A method of treating a susceptible cancer in a human or companion/pet animal, working animal, sport animal, zoo animal, or other valuable animal kept in captivity in need thereof, comprising administering thereto an effective amount of a monoclonal antibody or antigen binding fragment thereof of any one of embodiment 1-embodiment 7, or a monoclonal antibody, or antigen-binding fragment thereof, that competes with said monoclonal antibody or antigen-binding fragment thereof of any one of embodiment 1-embodiment 7 for binding to CD47, and which exhibits cytotoxic activity.

Embodiment 59. The method of embodiment 58, wherein said susceptible cancer is selected from the group consisting of a leukemia, a lymphoma, ovarian cancer, breast cancer, endometrial cancer, colon cancer, rectal cancer, bladder cancer, lung cancer, bronchial cancer, bone cancer, prostate cancer, pancreatic cancer, liver and bile duct cancer, esophageal cancer, renal cancer, thyroid cancer, head and neck cancer, testicular cancer, glioblastoma, astrocytoma, melanoma, and leiomyosarcoma.

Embodiment 60. The method of embodiment 59, wherein said leukemia is selected from the group consisting of acute lymphocytic (lymphoblastic) leukemia, acute myeloid leukemia, chronic lymphocytic leukemia, multiple myeloma, and chronic myeloid leukemia.

Embodiment 61. The method of any one of embodiment 58-embodiment 60, wherein said monoclonal antibody or antigen-binding fragment thereof of any one of embodiment 1-embodiment 7, or said monoclonal antibody, or antigen-binding fragment thereof, that competes with said monoclonal antibody or antigen-binding fragment thereof of any one of embodiment 1-embodiment 7 for binding to CD47 and which exhibits cytotoxic activity, increases phagocytosis of cells of said susceptible cancer.

Embodiment 62. The method of embodiment 61, wherein said monoclonal antibody or antigen-binding fragment thereof of any one of embodiment 1-embodiment 7, or said monoclonal antibody, or antigen-binding fragment thereof, that competes with said monoclonal antibody or antigen-binding fragment thereof of any one of embodiment 1-embodiment 7 for binding to CD47 which exhibits cytotoxic activity and increases phagocytosis of cells of said susceptible cancer inhibits CD47 binding to SIRPalpha.

Embodiment 63. The method of any one of embodiment 58- embodiment 62, wherein said monoclonal antibody or antigen-binding fragment thereof of any one of embodiment 1-embodiment 7, or said monoclonal antibody, or antigen-binding fragment thereof, that competes with said monoclonal antibody or antigen-binding fragment thereof of any one of embodiment 1-embodiment 7 for binding to CD47 and which exhibits cytotoxic activity, is directly toxic to cells of said susceptible cancer.

Further scope of the applicability of the present invention will become apparent from the detailed description provided below. However, it should be understood that the detailed description and specific examples, while indicating preferred embodiments of the invention, are given by way of illustration only since various changes and modifications within the spirit and scope of the invention will become apparent to those skilled in the art from this detailed description.

The following detailed description of the invention is provided to aid those skilled in the art in practicing the present invention. Even so, the following detailed description should not be construed to unduly limit the present invention, as modifications and variations in the embodiments herein discussed may be made by those of ordinary skill in the art without departing from the spirit or scope of the present inventive discovery.

DEFINITIONS

A full-length antibody as it exists naturally is an immunoglobulin molecule comprising two heavy (H) chains and two light (L) chains interconnected by disulfide bonds. The amino terminal portion of each chain includes a variable region of about 100-110 or more amino acids primarily responsible for antigen recognition via the complementarity determining regions (CDRs) contained therein. The carboxy-terminal portion of each chain defines a constant region primarily responsible for effector function.

The CDRs are interspersed with regions that are more conserved, termed framework regions ("FR"). Each light chain variable region (LCVR) and heavy chain variable region (HCVR) is composed of 3 CDRs and 4 FRs, arranged from amino-terminus to carboxy-terminus in the following order: FR1, CDR1, FR2, CDR2, FR3, CDR3, FR4. The 3 CDRs of the light chain are referred to as "LCDR1, LCDR2, and LCDR3" and the 3 CDRs of the heavy chain are referred to as "HCDR1, HCDR2, and HCDR3." The CDRs contain most of the residues which form specific interactions with the antigen. The numbering and positioning of CDR amino acid residues within the LCVR and HCVR regions are in accordance with the well-known Kabat numbering convention.

Light chains are classified as kappa or lambda, and are characterized by a particular constant region as known in the art. Heavy chains are classified as gamma, mu, alpha, delta, or epsilon, and define the isotype of an antibody as IgG, IgM, IgA, IgD, or IgE, respectively. IgG antibodies can be further divided into subclasses, e.g., IgG1, IgG2, IgG3, IgG4. Each heavy chain type is characterized by a particular constant region with a sequence well known in the art.

As used herein, the term "monoclonal antibody" (mAb) as applied to the present antibody compounds refers to an antibody that is derived from a single copy or clone including, for example, any eukaryotic, prokaryotic, or phage clone, and not the method by which it is produced. mAbs of the present invention preferably exist in a homogeneous or substantially homogeneous population. Complete mAbs contain two heavy chains and two light chains. "Antigen binding fragments" of such monoclonal antibodies include, for example, Fab fragments, Fab' fragments, F(ab')$_2$ fragments, single chain Fv fragments, and one-armed antibodies comprising a light chain and a heavy chain. Monoclonal antibodies and antigen-binding fragments thereof of the present invention can be produced, for example, by recombinant technologies, phage display technologies, synthetic technologies, e.g., CDR-grafting, or combinations of such technologies, or other technologies known in the art.

"Antibody compounds" refers to mAbs and Fabs, and competing antibodies, disclosed herein. Additional antibody compounds exhibiting similar functional properties according to the present invention can be generated by conventional methods. For example, mice can be immunized with human CD47 or fragments thereof, the resulting antibodies can be recovered and purified, and determination of whether they possess binding and functional properties similar to or the same as the antibody compounds disclosed herein can be assessed by the methods disclosed in Examples 3 and 4, below. Antigen-binding fragments can also be prepared by conventional methods. Methods for producing and purifying antibodies and antigen-binding fragments are well known in the art and can be found, for example, in Harlow and Lane (1988) *Antibodies, A Laboratory Manual*, Cold Spring Harbor Laboratory Press, Cold Spring Harbor, N.Y., chapters 5-8 and 15, ISBN 0-87969-314-2.

The phrase "humanized antibodies" refers to monoclonal antibodies and antigen binding fragments thereof in addition to the antibody compounds disclosed herein that have binding and functional properties according to the invention similar to those disclosed herein, and that have framework regions that are substantially human or fully human surrounding CDRs derived from a non-human antibody. "Framework region" or "framework sequence" refers to any one of framework regions 1 to 4. Humanized antibodies and antigen binding fragments encompassed by the present invention include molecules wherein any one or more of framework regions 1 to 4 is substantially or fully human, i.e., wherein any of the possible combinations of individual substantially or fully human framework regions 1 to 4, is present. For example, this includes molecules in which framework region 1 and framework region 2, framework region 1 and framework region 3, framework region 1, 2, and 3, etc., are substantially or fully human. Substantially human frameworks are those that have at least about 80% sequence identity to a known human germline framework sequence. Preferably, the substantially human frameworks have at least about 85%, at least about 90%, at least about 95%, or at least about 99% sequence identity to a known human germline framework sequence.

Fully human frameworks are those that are identical to a known human germline framework sequence. Human framework germline sequences can be obtained from ImMunoGeneTics (IMGT) via their website or from The Immunoglobulin FactsBook by Marie-Paule Lefranc and Gerard Lefranc, Academic Press, 2001, ISBN 012441351. For example, germline light chain frameworks can be selected from the group consisting of: A11, A17, A18, A19, A20, A27, A30, LI, L1I, L12, L2, L5, L15, L6, L8, O12, O2, and O8, and germline heavy chain framework regions can be selected from the group consisting of: VH2-5, VH2-26, VH2-70, VH3-20, VH3-72, VHI-46, VH3-9, VH3-66, VH3-74, VH4-31, VHI-18, VHI-69, VI-13-7, VH3-11, VH3-15, VH3-21, VH3-23, VH3-30, VH3-48, VH4-39, VH4-59, and VH5-5I.

Humanized antibodies in addition to those disclosed herein exhibiting similar functional properties according to the present invention can be generated using several different methods. In one approach, the parent antibody compound CDRs are grafted into a human framework that has a high sequence identity with the parent antibody compound framework. The sequence identity of the new framework will generally be at least about 80%, at least about 85%, at least about 90%, at least about 95%, or at least about 99% identical to the sequence of the corresponding framework in the parent antibody compound. In the case of frameworks having fewer than 100 amino acid residues, one, two, or three amino acid residues can be changed. This grafting may result in a reduction in binding affinity compared to that of the parent antibody. If this is the case, the framework can be back-mutated to the parent framework at certain positions based on specific criteria disclosed by Queen et al. (1991) *Proc. Natl. Acad. Sci. USA* 88:2869. Additional references describing methods useful in humanizing mouse antibodies include U.S. Pat. Nos. 4,816,397; 5,225,539; and 5,693,761; computer programs ABMOD and ENCAD as described in Levitt (1983) *J. Mol. Biol.* 168:595-620; and the method of Winter and co-workers (Jones et al. (1986) *Nature* 321:522-525; Riechmann et al. (1988) *Nature* 332:323-327; and Verhoeyen et al. (1988) *Science* 239:1534-1536.

The identification of residues to consider for back-mutation can be carried out as follows.

When an amino acid falls under the following category, the framework amino acid of the human germ-line sequence that is being used (the "acceptor framework") is replaced by a framework amino acid from a framework of the parent antibody compound (the "donor framework"): (a) the amino acid in the human framework region of the acceptor framework is unusual for human frameworks at that position, whereas the corresponding amino acid in the donor immunoglobulin is typical for human frameworks at that position; (b) the position of the amino acid is immediately adjacent to one of the CDRs; or (c) any side chain atom of a framework amino acid is within about 5-6 angstroms (center-to-center) of any atom of a CDR amino acid in a three dimensional immunoglobulin model.

When each of the amino acids in the human framework region of the acceptor framework and a corresponding amino acid in the donor framework is generally unusual for human frameworks at that position, such amino acid can be replaced by an amino acid typical for human frameworks at that position. This back-mutation criterion enables one to recover the activity of the parent antibody compound.

Another approach to generating human engineered antibodies exhibiting similar functional properties to the antibody compounds disclosed herein involves randomly mutating amino acids within the grafted CDRs without changing the framework, and screening the resultant molecules for binding affinity and other functional properties that are as good as or better than those of the parent antibody compounds. Single mutations can also be introduced at each amino acid position within each CDR, followed by assessing the effects of such mutations on binding affinity and other functional properties. Single mutations producing improved properties can be combined to assess their effects in combination with one another.

Further, a combination of both of the foregoing approaches is possible. After CDR grafting, one can back-mutate specific framework regions in addition to introducing amino acid changes in the CDRs. This methodology is described in Wu et al. (1999) J. Mol. Biol. 294:151-162.

The method described in Example 1 below can also be employed.

Applying the teachings of the present invention, a person skilled in the art can use common techniques, e.g., site-directed mutagenesis, to substitute amino acids within the presently disclosed CDR and framework sequences and thereby generate further variable region amino acid sequences derived from the present sequences. Up to all naturally occurring amino acids can be introduced at a specific substitution site. The methods disclosed herein can then be used to screen these additional variable region amino acid sequences to identify sequences having the indicated in vivo functions. In this way, further sequences suitable for preparing human engineered antibodies and antigen-binding portions thereof in accordance with the present invention can be identified. Preferably, amino acid substitution within the frameworks is restricted to one, two, or three positions within any one or more of the 4 light chain and/or heavy chain framework regions disclosed herein. Preferably, amino acid substitution within the CDRs is restricted to one, two, or three positions within any one or more of the 3 light chain and/or heavy chain CDRs. Combinations of the various changes within these framework regions and CDRs described above are also possible.

That the functional properties of the antibody compounds generated by introducing the amino acid modifications discussed above conform to those exhibited by the specific molecules disclosed herein can be confirmed by the methods disclosed below in Examples 3 and 4.

The terms "specifically binds", "bind specifically", "specific binding", and the like as applied to the present antibody compounds refer to the ability of a specific binding agent (such as an antibody) to bind to a target molecular species in preference to binding to other molecular species with which the specific binding agent and target molecular species are admixed. A specific binding agent is said specifically to recognize a target molecular species when it can bind specifically to that target.

"Binding affinity" is a term that refers to the strength of binding of one molecule to another at a site on the molecule. If a particular molecule will bind to or specifically associate with another particular molecule, these two molecules are said to exhibit binding affinity for each other. Binding affinity is related to the association constant and dissociation constant for a pair of molecules, but it is not critical to the methods herein that these constants be measured or determined. Rather, affinities as used herein to describe interactions between molecules of the described methods are generally apparent affinities (unless otherwise specified) observed in empirical studies, which can be used to compare the relative strength with which one molecule (e.g., an antibody or other specific binding partner) will bind two other molecules (e.g., two versions or variants of a peptide). The concepts of binding affinity, association constant, and dissociation constant are well known.

The term "epitope" refers to a specific arrangement of amino acids located on a peptide or protein to which an antibody or antibody fragment binds. Epitopes often consist of a chemically active surface grouping of molecules such as amino acids or sugar side chains, and have specific three dimensional structural characteristics as well as specific charge characteristics. Epitopes can be linear, i.e., involving binding to a single sequence of amino acids, or conformational, i.e., involving binding to two or more sequences of amino acids in various regions of the antigen that may not necessarily be contiguous.

Monoclonal antibodies or antigen-binding fragments thereof that "compete" with the molecules disclosed herein are those that bind human CD47 at site(s) that are identical to, or overlapping with, the site(s) at which the present molecules bind. Competing monoclonal antibodies or antigen-binding fragments thereof can be identified, for example, via an antibody competition assay. For example, a sample of purified or partially purified human CD47 extracellular domain can be bound to a solid support. Then, an antibody compound, or antigen binding fragment thereof, of the present invention and a monoclonal antibody or antigen-binding fragment thereof suspected of being able to compete with such invention antibody compound are added. One of the two molecules is labeled. If the labeled compound and the unlabeled compound bind to separate and discrete sites on CD47, the labeled compound will bind to the same level whether or not the suspected competing compound is present. However, if the sites of interaction are identical or overlapping, the unlabeled compound will compete, and the amount of labeled compound bound to the antigen will be lowered. If the unlabeled compound is present in excess, very little, if any, labeled compound will bind. For purposes of the present invention, competing monoclonal antibodies or antigen-binding fragments thereof are those that decrease the binding of the present antibody compounds to CD47 by about 50%, about 60%, about 70%, about 80%, about 85%, about 90%, about 95%, or about 99%. Details of procedures for carrying out such competition assays are well known in the art and can be found, for example, in Harlow and Lane (1988) *Antibodies, A Laboratory Manual*, Cold Spring Harbor Laboratory Press, Cold Spring Harbor, N.Y., pages 567-569, ISBN 0-87969-314-2. Such assays can be made quantitative by using purified antibodies. A standard curve is established by titrating one antibody against itself, i.e., the same antibody is used for both the label and the competitor. The capacity of an unlabeled competing monoclonal antibody or antigen-binding fragment thereof to inhibit the binding of the labeled molecule to the plate is titrated. The results are plotted, and the concentrations necessary to achieve the desired degree of binding inhibition are compared. Whether monoclonal antibodies or antigen-binding fragments thereof that compete with antibody compounds of the present invention in such competition assays possess the same or similar functional properties of the present antibody compounds can be determined via these methods in conjunction with the methods described in Examples 3 and 4, below.

The term "treating" (or "treat" or "treatment") means slowing, interrupting, arresting, controlling, stopping, reducing, or reversing the progression or severity of a sign, symptom, disorder, condition, or disease, but does not necessarily involve a total elimination of all disease-related signs, symptoms, conditions, or disorders. The team "treating" and the like refer to a therapeutic intervention that ameliorates a sign, symptom, etc., of a disease or pathological condition after it has begun to develop.

Acute events and chronic conditions can be treated. In an acute event, an antibody or antigen binding fragment thereof is administered at the onset of a symptom, disorder, condition, disease, or procedure, and is discontinued when the acute event ends, or in the case of organ transplantation to the organ, at the time of organ harvest and/or to the transplant recipient at the time of organ transplantation. In contrast, a chronic symptom, disorder, condition, or disease is treated over a more protracted time frame.

The term "effective amount" refers to the amount or dose of an antibody compound of the present invention which, upon single or multiple dose administration to a patient or organ, provides the desired treatment or prevention. Therapeutically effective amounts of the present antibody compounds can comprise an amount in the range of from about 0.1 mg/kg to about 150 mg/kg, more preferably from about 0.1 mg/kg to about 100 mg/kg, and even more preferably from about 0.1 mg/kg to about 50 mg/kg per single dose administered to a harvested organ or to a patient. A therapeutically effective amount for any individual patient can be determined by the health care provider by monitoring the effect of the antibody compounds on a biomarker, such as serum biomarkers of injury of the treated organ, including but not limited to liver, kidney, lung, intestine, pancreas and heart, changes in pulmonary artery pressures, cell surface CD47 expression in tumor or non-tumor tissues, tumor regression, circulating tumor cells or tumor stem cells, etc. Analysis of the data obtained by these methods permits modification of the treatment regimen during therapy so that optimal amounts of antibody compounds of the present invention, whether employed alone or in combination with one another, or in combination with another therapeutic agent, or both, are administered, and so that the duration of treatment can be determined as well. In this way, the dosing/treatment regimen can be modified over the course of therapy so that the lowest amounts of antibody compounds used alone or in combination that exhibit satisfactory efficacy are administered, and so that administration of such compounds is continued only so long as is necessary to successfully treat the patient.

The antibody compounds of the present invention can be used as medicaments in human and veterinary medicine, administered by a variety of routes. Veterinary applications include the treatment of companion/pet animals, such as cats and dogs; working animals, such as guide or service dogs, and horses; sport animals, such as horses and dogs; zoo animals, such as primates, cats such as lions and tigers, bears, etc.; and other valuable animals kept in captivity.

Most preferably, such compositions are for parenteral administration. Such pharmaceutical compositions can be prepared by methods well known in the art. See, e.g., *Remington: The Science and Practice of Pharmacy*, 21' Edition (2005), Lippincott Williams & Wilkins, Philadelphia, Pa., and comprise one or more antibody compounds disclosed herein, and a pharmaceutically or veterinarily acceptable, e.g., physiologically acceptable, carrier, diluent, or excipient.

It should be noted that in all of the therapeutic methods disclosed and claimed herein, the monoclonal antibodies or antigen binding fragments thereof, and monoclonal antibodies or antigen binding fragments thereof that compete with these monoclonal antibodies or antigen binding fragments thereof of the present invention that bind to CD47, can be used alone, or in any appropriate combinations with one another, to achieve the greatest treatment efficacy.

The term "tumor" refers to all neoplastic cell growth and proliferation, whether malignant or benign, and all pre-cancerous and cancerous cells and tissues. The terms "cancer", "cancerous", and "tumor" are not mutually exclusive as used herein.

The terms "cancer" and "cancerous" refer to or describe the physiological condition in mammals that is typically characterized by aberrant cell growth/proliferation. Examples of cancers include, but are not limited to, carcinomas, lymphomas, blastomas, sarcomas, and leukemias.

The term "susceptible cancer" as used herein refers to a cancer, cells of which express CD47 and that are responsive to treatment with an antibody or antigen binding fragment thereof of the present invention. Exemplary susceptible cancers include, but are not limited to, leukemias, including acute lymphocytic (lymphoblastic) leukemia, acute myeloid leukemia, chronic lymphocytic leukemia, multiple myeloma, chronic myeloid leukemia, lymphomas, ovarian cancer, breast cancer, endometrial cancer, colon cancer, rectal cancer, bladder cancer, lung cancer, bronchial cancer, bone cancer, prostate cancer, pancreatic cancer, liver and bile duct cancer, esophageal cancer, renal cancer, thyroid cancer, head and neck cancer, testicular cancer, glioblastoma, astrocytoma, melanoma, and leiomyosarcoma.

The term "directly toxic" refers to the ability of certain of the humanized antibodies or antigen binding fragments thereof disclosed herein to kill transformed/cancer cells via a cell autonomous mechanism without participation of complement or other cells, including but not limited to, T cells, neutrophils, natural killer cells, macrophages, or dendritic cells.

"Ischemia" refers to a vascular phenomenon in which a decrease in the blood supply to a bodily organ, tissue, or part is caused, for instance, by constriction or obstruction of one or more blood vessels. Ischemia sometimes results from vasoconstriction or thrombosis or embolism. Ischemia can lead to direct ischemic injury, tissue damage due to cell death caused by reduced oxygen supply. Ischemia can occur acutely, as during surgery, or from trauma to tissue incurred in accidents, injuries and war settings, or following harvest of organs intended for subsequent transplantation, for example. It can also occur sub-acutely, as found in atherosclerotic peripheral vascular disease, where progressive narrowing of blood vessels leads to inadequate blood flow to tissues and organs.

When a tissue is subjected to ischemia, a sequence of chemical events is initiated that may ultimately lead to cellular dysfunction and necrosis. If ischemia is ended by the restoration of blood flow, a second series of injurious events ensue, producing additional injury. Thus, whenever there is a transient decrease or interruption of blood flow in a subject, the resultant injury involves two components—the direct injury occurring during the ischemic interval, and the indirect or reperfusion injury that follows.

"Ischemic stroke" can be caused by several different kinds of diseases. The most common problem is narrowing of the arteries in the neck or head. This is most often caused by atherosclerosis, or gradual cholesterol deposition. If the arteries become too narrow, blood cells may collect in them and form blood clots (thrombi). These blood clots can block the artery where they are formed (thrombosis), or can dislodge and become trapped in arteries closer to the brain (embolism). Cerebral stroke can occur when atherosclerotic plaque separates away partially from the vessel wall and occludes the flow of blood through the blood vessel.

"Reperfusion" refers to restoration of blood flow to tissue that is ischemic, due to decrease in blood flow. Reperfusion is a procedure for treating infarction or other ischemia, by enabling viable ischemic tissue to recover, thus limiting further necrosis. However, reperfusion can itself further damage the ischemic tissue, causing reperfusion injury.

In addition to the immediate injury that occurs during deprivation of blood flow, "ischemic/reperfusion injury" involves tissue injury that occurs after blood flow is restored. Current understanding is that much of this injury is caused by chemical products, free radicals, and active biological agents released by the ischemic tissues.

"Nitric oxide donor or precursor" refers to a compound or agent that either delivers NO, or that can be converted to NO through enzymatic or non-enzymatic processes. Examples include, but are not limited to, NO gas, isosorbide dinitrate, nitrite, nitroprusside, nitroglycerin, 3-Morpholinosydnonimine (SIN-1), S-nitroso-N-acetylpenicillamine (SNAP), Diethylenetriamine/NO (DETA/NO), S-nitrosothiols, and arginine.

CD47 and Ischemia-Reperfusion Injury (IRI)

Following periods of tissue ischemia, the initiation of blood flow causes damage referred to as "ischemia-reperfusion injury" or IRI. IRI contributes to poor outcomes in many surgical procedures where IRI occurs due to the necessity to stop blood flow for a period of time, in many forms/causes of trauma in which blood flow is interrupted and later restored by therapeutic intervention and in procedures required for organ transplantation, cardio/pulmonary bypass procedures, reattachment of severed body parts, reconstructive and cosmetic surgeries and other situations involving stopping and restarting blood flow. Ischemia itself causes many physiological changes that, by themselves would eventually lead to cell and tissue necrosis and death. Reperfusion poses its own set of damaging events including generation of reactive oxygen species, thrombosis, inflammation and cytokine mediated damage. The pathways that are limited by the TSP1-CD47 system are precisely those that would be of most benefit in combating the damage of IRI. Thus, blocking the TSP1-CD47 pathway, as with the antibodies disclosed herein, will provide more robust functioning of these endogenous protective pathways.

The humanized anti-CD47 antibodies, antigen binding fragments thereof, and competing antibodies and antigen binding fragments thereof, of the present invention can be used in the methods disclosed in U.S. Pat. No. 8,236,313, the contents of which are herein incorporated by reference in their entirety.

CD47 and Cancer

CD47 has been identified as a novel therapeutic target in hematologic cancers (Majeti et al. (2009) *Cell* 138(2):286-99, as well as in solid tumors such as colon, prostate, breast, and brain cancers (Willingham et al. (2012) *Proc Natl Acad Sci USA* 109(17):6662-7. Many human cancers up-regulate cell surface expression of CD47 and those expressing the highest levels of CD47 are the most aggressive and the most lethal for patients. Increased CD47 expression is thought to protect cancer cells from phagocytic clearance by sending a "don't eat me" signal to macrophages via SIRPalpha, an inhibitory receptor that prevents phagocytosis of CD47-bearing cells (Jaiswal et al. (2009) *Cell* 138(2):271-851; Chao et al. (2010) *Science Translational Medicine* 2(63):63ra94). Thus, the increase of CD47 expression by many cancers provides them with a cloak of "selfness" that slows their phagocytic clearance by macrophages and dendritic cells. Anti-CD47 mAbs (CD47mAbs) that block the CD47/SIRPalpha interaction enhance phagocytosis of cancer cells in vitro and contribute to control of tumor burden in published human to mouse xenograft tumor models. However, there are mechanisms by which CD47 mAbs can attack transformed cells that have not yet been exploited in the war on cancer.

Frazier et al. have shown that a particular anti-human CD47mAb (clone 1F7) has a direct, tumor-toxic effect on human T cell leukemias (Manna and Frazier (2003) *A. J. Immunol.* 170:3544-53) and several breast cancers (Manna and Frazier (2004) *A. Cancer Research* 64(3):1026-36). Other groups have reported such findings in additional types of leukemia (Uno et al. (2007) *Oncol. Rep.* 17(5):1189-94; Mateo et al. (1999) *Nat. Med.* 5:1277-84). MAb 1F7 kills CD47 bearing tumor cells without the action of complement or cell mediated killing by NK cells, T cells or macrophages. Instead, mAb 1F7 acts via a non-apoptotic mechanism that involves a direct CD47-dependent attack on mitochondria, discharging their membrane potential and destroying the ATP-generating capacity of the cell leading to rapid cell death. It is noteworthy that mAb 1F7 does not kill resting leukocytes, which also express CD47, but only those cells that are "activated" by transformation. Thus, normal circulating cells, all of which express CD47, are spared while cancer cells are selectively killed by the tumor-toxic CD47mAb (Manna and Frazier (2003) *A. J. Immunol.* 170:3544-53). This mechanism can be thought of as a proactive, selective and direct attack on tumor cells in contrast to the passive mechanism of promoting phagocytosis by simply blocking CD47/SIRPalpha binding. Importantly, mAb 1F7 also blocks binding of SIRPalpha to CD47 and thus it can act via two mechanisms: (1) direct tumor cytotoxicity, and (2) promoting phagocytosis of the dead and dying tumor cells. A single mAb that can accomplish both functions may be superior to one that only blocks CD47/SIRPalpha binding. In fact, it has been shown that combining a blocking CD47mAb to promote phagocytosis with the cytotoxic anti-CD20 mAb, rituximab, is more effective than either mAb alone at eradicating human non-Hodgkins lymphoma in a xenograft mouse model (Chao et al. (2010) *Cell* 142(5):699-713). However, rituximab kills by lysing cancer cells, leading to a harsh side effect profile (Hansel et al. (2010) *Nat Rev Drug Discov.* 9(4):325-38). In contrast, the tumor-toxic mAb 1F7 does not cause rapid cell lysis, but rather causes display of phosphatidylserine on the cell surface, thus promoting phagocytic clearance by this mechanism as well.

Therapeutic Indications

IRI-Related and Autoimmune/Inflammatory Conditions

Administration of a CD47 mAb or antigen binding fragment thereof disclosed herein can be used to treat a number of diseases and conditions in which IRI is a contributing feature, and to treat various autoimmune and inflammatory diseases. These include: organ transplantation in which a mAb or antigen binding fragment thereof of the present invention is administered to the donor prior to organ harvest, to the harvested donor organ, to the organ preservation solution, to the recipient patient, or to any combination thereof; skin grafting; surgical resections or tissue reconstruction in which such mAb or fragment is administered either locally by injection to the affected tissue or parenterally to the patient; reattachment of body parts; treatment of traumatic injury; pulmonary hypertension; sickle cell disease (crisis); myocardial infarction; stroke; surgically-induced ischemia; acute kidney disease/kidney failure; any other condition in which IRI occurs and contributes to the pathogenesis of disease; and autoimmune/inflammatory diseases, including arthritis, multiple sclerosis, psoriasis, Crohn's disease, inflammatory bowel disease, lupus, Grave's disease and Hashimoto's thyroiditis, and ankylosing spondylitis.

CD47 mAbs and antigen binding fragments thereof of the present invention can also be used to increase tissue perfusion in a subject in need of such treatment. Such subjects can be identified by diagnostic procedures indicating a need for increased tissue perfusion. In addition, the need for increased tissue perfusion may arise because the subject has had, is having, or will have, a surgery selected from integument surgery, soft tissue surgery, composite tissue surgery, skin graft surgery, resection of a solid organ, organ transplant surgery, or reattachment or an appendage or other body part.

Susceptible Cancers

Presently disclosed mAbs effective as cancer therapeutics can be administered to patients, preferably parenterally, with susceptible hematologic cancers and solid tumors including, but not limited to, leukemias, including acute lymphocytic (lymphoblastic) leukemia, acute myeloid leukemia, chronic lymphocytic leukemia, multiple myeloma, chronic myeloid leukemia, lymphomas, ovarian cancer, breast cancer, endometrial cancer, colon cancer, rectal cancer, bladder cancer, lung cancer, bronchial cancer, bone cancer, prostate cancer, pancreatic cancer, liver and bile duct cancer, esophageal cancer, renal cancer, thyroid cancer, head and neck cancer, testicular cancer, glioblastoma, astrocytoma, melanoma, and leiomyosarcoma.

In certain cases, it may be advantageous to administer the mAb directly to the cancer by injection into the tumor. Since CD47 expression is up-regulated on many cancers, it may also be desirable to use one or more of the disclosed mAbs as imaging and diagnostic agents when labeled with radioactive or other tracers known to those skilled in the art of in vivo imaging of cancers/tumors.

The following examples illustrate various aspects of the present invention, but should not be considered as limiting the invention only to these particularly disclosed embodiments.

EXAMPLE 1

Production of CD47 Antibodies

The humanized antibodies disclosed herein comprise frameworks derived from the human genome. The collection covers the diversity found in the human germ line sequences, yielding functionally expressed antibodies in vivo. The complementarity determining regions (CDRs) in the light and heavy chain variable regions of the target chimeric, non-human antibody VxP037-01LC/VxP037-01HC (SEQ ID NO:7/SEQ ID NO:57) are determined following commonly accepted rules disclosed, for example, in "Protein Sequence and Structure Analysis of Antibody Variable Domains", In: *Antibody Engineering Lab Manual*, Eds. S. Duebel and R. Kontermann, Springer-Verlag, Heidelberg (2001)). The CDR fragments are synthesized and combined with pools of frameworks to generate full length variable domains. The humanized variable domains are then combined with a secretion signal and human kappa and human IgG1 constant domains, and cloned into a mammalian expression system (e.g., Opti-CHO System, Lifetechnologies, Carlsbad, Calif.) to generate a library of humanized IgG1 variants. An aliquot of the library is sequenced to ensure high diversity and integrity of the reading frames of the individual clones. Aliquots of the humanized variant library are then re-arrayed as single clones into 96 well plates, mini-prepped (e.g., 96 well Miniprep Kit, Qiagen Hilden, Germany), and transfected into CHO cells (Lipofectamine transfection protocol as recommended by Lifetechnologies, Carlsbad, Calif.). Transfected CHO cells are grown in DMEM medium with 10% FBS (both from Lifetechnologies, Carlsbad, Calif.) at 37° C. under 5% $CO_2$. The humanized variants are expressed as full length IgG1 molecules, and secreted into the medium.

The cell culture supernatant containing the humanized IgG variants is then screened for binding to the target antigen. In parallel, the concentration of each variant is determined in order to calculate specific activity for each clone. The specific activity of each clone is compared to the specific activity of chimeric clone VxP037-01LC/VxP037-01HC (SEQ ID NO:7/SEQ ID NO:57) expressed on the same plate, and normalized. Top hits from each plate are re-arrayed and re-screened for confirmation. The final candidates are selected by specific activity, functional activity, expression level, and sequence diversity, as well as other criteria, as described below.

EXAMPLE 2

CD47 Antibody CDRs

The amino acid sequences of the light chain and heavy chain variable regions, the complete light and heavy chains, and the respective encoding nucleotide sequences of the foregoing, of the present human engineered antibodies are listed below in the section entitled "Amino Acid and Nucleic Acid Sequences."

The light chain and heavy chain CDR amino acid sequences are shown in Tables 1 and 2, respectively.

TABLE 1

Light Chain CDRs

| CDR1 | CDR2 | CDR3 |
|---|---|---|
| RSSQSLVHSNGNTYLH (SEQ ID NO: 1) | KVSYRFS (SEQ ID NO: 2) | SQNTHVPRT (SEQ ID NO: 3) |

TABLE 2

Heavy Chain CDRs

| CDR1 | CDR2 | CDR3 |
|---|---|---|
| GYTFTNYYVF (SEQ ID NO: 4) | DINPVNGDTNFNEKFKN (SEQ ID NO: 5) | GGYTMDY (SEQ ID NO: 6) |

EXAMPLE 3

Binding of Antibodies to CD47 of Different Species

Cross species reactivity of humanized antibodies of the present invention is determined using freshly isolated red blood cells (RBCs), which display CD47 on their surface, from human, mouse, rat, and pig according to the methods disclosed in Kamel et al. (2010) *Blood. Transfus.* 8(4):260-266.

Supernatants containing secreted antibodies are collected from CHO cells transiently transfected with plasmids encoding antibody clones. Transfected CHO cells are grown in F-12 medium containing 10% heat inactivated fetal bovine serum (BioWest; S01520). Antibody concentration in the supernatants is determined utilizing a quantitative ELISA. ELISA plates are coated with a donkey anti-human FC antibody (Sigma; Catalog #12136) at 10 µg/ml overnight at 4° C. (Promega; Catalog # W4031). Plates are washed with PBS, and then blocked with casein blocking solution (ThermoScientific; Catalog #37532) for 60 minutes at room temperature. Plates are again washed with PBS, tissue culture supernatants are added, and the plates are incubated for 60 minutes at room temperature. Plates are then washed three times with PBS and incubated with peroxidase-conjugated goat anti-human IgG (Jackson Immunoresearch Labs; Catalog #109-035-003) for 60 minutes at room temperature. Plates are washed three times with PBS, and the peroxidase substrate 3,3',5,5'-tetramethylbenzidine is added (Sigma; Catalog #T4444). Reactions are terminated by the addition of HCl to 0.7N, and absorbance at 450 nM is determined using a Tecan model Infinite M200 plate reader.

RBCs are incubated for 60 minutes on ice with tissue culture supernatants containing the secreted humanized antibodies at a concentration of 10 ng/ml in a solution of phosphate buffered saline, pH 7.2, 2.5 mM EDTA (PBS+E). Cells are then washed with cold PBS+E, and incubated for an additional hour on ice with FITC labeled donkey anti-human antibody (Jackson Immuno Research Labs, West Grove, Pa.; Catalogue #709-096-149) in PBS+E. Cells are then washed with PBS+E, and antibody binding is analyzed using a BD FACSAria Cell Sorter (Becton Dickinson) or a C6 Accuri Flow Cytometer (Becton Dickinson). Antibody binding is quantitated by comparison of mean fluorescence values relative to that of chimeric antibody >VxP037-01LC (SEQ ID NO:7))/>VxP037-01HC (SEQ ID NO:57). The mean fluorescence value for each antibody is divided by the mean fluorescence value for the chimeric antibody.

The results are shown in Table 3, where "Chimera" represents chimeric antibody >VxP037-01LC (SEQ ID NO:7))/>VxP037-01HC (SEQ ID NO:57), Clone 1 represents >pVxK7b-037-hum01-LC (SEQ ID NO:8)/>pVxK7b-037-hum01-HC (SEQ ID NO:58), Clone 2 represents >pVxK7b-037-hum02-LC (SEQ ID NO:9)/>pVxK7b-037-hum02-HC (SEQ ID NO:59), and so on similarly for remaining clones 3-24.

TABLE 3

Binding of Humanized Antibodies to CD47 on the Surface of Red Blood Cells of Different Mammalian Species

| Clone No. | Human | Mouse | Rat | Pig |
| --- | --- | --- | --- | --- |
| Chimera | 1.0 | 1.0 | 1.0 | 1.0 |
| 1 | 1.1 | 1.7 | 2.7 | 1.3 |
| 2 | 1.0 | 1.2 | 2.6 | 1.2 |
| 3 | 0.7 | 0.9 | 1.7 | 0.9 |
| 4 | 0.6 | 0.6 | 1.0 | 0.6 |
| 5 | 1.0 | 1.0 | 2.2 | 1.2 |
| 6 | 0.9 | 1.2 | 2.1 | 1.1 |
| 7 | 0.5 | 0.4 | 0.8 | 0.9 |
| 8 | 0.7 | 0.7 | 1.2 | 0.8 |
| 9 | 1.2 | 1.4 | 3.7 | 1.6 |
| 10 | 1.1 | 1.2 | 2.9 | 1.5 |
| 11 | 0.8 | 0.7 | 1.2 | 1.2 |
| 12 | 0.8 | 0.6 | 1.3 | 1.4 |
| 13 | 1.2 | 1.3 | 3.1 | 1.4 |
| 14 | 1.1 | 1.5 | 3.2 | 1.4 |
| 15 | 1.0 | 1.3 | 2.4 | 1.2 |
| 16 | 0.9 | 1.0 | 2.1 | 1.1 |
| 17 | 0.8 | 0.9 | 2.1 | 1.3 |
| 18 | 1.0 | 1.3 | 2.2 | 1.2 |
| 19 | 0.7 | 1.0 | 2.6 | 1.3 |
| 20 | 1.3 | 1.5 | 1.9 | 1.7 |
| 21 | 1.2 | 1.2 | 2.8 | 1.4 |
| 22 | 1.1 | 1.2 | 2.8 | 1.4 |
| 23 | 1.2 | 1.4 | 3.3 | 1.7 |
| 24 | 0.8 | 0.7 | 1.2 | 1.1 |

These data demonstrate that all of the humanized CD47 mAb clones disclosed herein bind well to CD47 of a variety of different mammalian species, confirming the useful cross-species reactivity of these antibodies.

EXAMPLE 4

Cell Viability Assay

The purpose of this experiment is to identify antibody clones of the present invention that do, and do not, exhibit cytotoxic activity. For use in cardiovascular indications, including transplantation and other applications related to IRI, the therapeutic mAb should lack cytotoxic activity. In contrast, antibodies useful in the treatment of cancer should exhibit toxicity against transformed/cancer cells. This additional property of selective toxicity to cancer cells is expected to have advantages compared to mAbs that only prevent SIR-Palpha binding to CD47.

The method employed is described in Vistica et al. (1991) *Cancer Res.* 51:2515-2520.

Jurkat JE6.1 cells (ATCC, Manassas, Va.; Catalog # TIB-152) are grown in Iscove's modified Dulbeccco's medium containing 5% (v/v) heat inactivated fetal bovine serum (BioWest; Catalogue # S01520), 100 units/mL, penicillin, 100 µg mL streptomycin (Sigma; Catalogue # P4222) at densities less than $1 \times 10^6$ cells/mL For the cell viability assay, cells are plated in 96 well tissue culture plates at a density of $2 \times 10^4$ cells/ml in Iscoves modified Dulbecco's medium containing 5% (v/v) heat inactivated fetal bovine serum (BioWest; Catalog # S01520), 100 units/mL penicillin, 100 µg/mL streptomycin (Sigma; #P4222) along with humanized antibodies as disclosed herein at a final concentration of 10 ng/ml, prepared as described above in Example 3. Cells are incubated for 72 hours at 37° C. in an atmosphere of 5% (v/v) $CO_2$. Cell density is then quantitated using WST1 reagent (Roche Applied Science, Indianapolis, Ind.; Catalog #05015944001) according to the manufacturer's instructions. The effect of the antibodies on cell growth is quantitated by comparison to growth of cells containing no added antibody (PBS; average percent killing=0).

The results are shown in table 4. The values in the table represent the mean of 3 separate experiments. "Chimera" and clone numbers are as described above in Example 3. 1F7 is the anti-human CD47mAb, discussed above, that has a direct, tumor-toxic effect on human T cell leukemias (Manna and Frazier (2003) *A. J. Immunol.* 170:3544-53) and several breast cancers (Manna and Frazier (2004) *A. Cancer Research* 64(3):1026-36).

TABLE 4

Cytotoxicity of Humanized CD47mAbs on Transformed Human T Cells, Jurkat JE6.1

| Clone No. | Average % Killing | % of 1F7 | Cytotoxic |
|---|---|---|---|
| Chimera | 4.3 | 19 | |
| 1 | −3.3 | −14 | |
| 2 | 9.8 | 43 | Yes |
| 3 | 8.6 | 38 | Yes |
| 4 | 6.8 | 30 | |
| 5 | 11.8 | 52 | Yes |
| 6 | 14 | 61 | Yes |
| 7 | 1.8 | 8 | |
| 8 | 10.6 | 46 | Yes |
| 9 | 1 | 4 | |
| 10 | 7.4 | 32 | Yes |
| 11 | −7.2 | −32 | |
| 12 | −6.9 | −30 | |
| 13 | 17.8 | 78 | Yes |
| 14 | 16.5 | 72 | Yes |
| 15 | 8.1 | 36 | Yes |
| 16 | 8.7 | 38 | Yes |
| 17 | 12.4 | 54 | Yes |
| 18 | 5.4 | 23 | |
| 19 | 9.6 | 42 | Yes |
| 20 | 3.1 | 14 | |
| 21 | 4.5 | 20 | |
| 22 | −0.7 | −3 | |
| 23 | 4.8 | 21 | |
| 24 | −13.1 | −57 | |
| 1F7 | 22.9 | 100 | Yes |

These data demonstrate that the majority of the present humanized antibody clones are not significantly cytotoxic toward Jurkat T cells. However, certain of the clones have significant cytotoxicity, similar to previously identified mouse anti-human CD47mAb 1F7 (Manna and Frazier, *J. Immunol.* (2003) 170(7):3544-53.

The following clones, indicated in Table 2 with a "Yes", are considered to be cytotoxic: 2, 3, 5, 6, 8, 10, 13, 14, 15, 16, 17, and 19.

The following clones are considered to be non-toxic: 1, 4, 7, 9, 11, 12, 18, 20, 21, 22, 23, and 24.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

```
Amino Acid and Nucleic Acid Sequences
Light Chain Variable Region Amino Acid Sequences
>VxP037-01LC: Underlined amino acid sequences represent CDRs
                                                    (SEQ ID NO: 7)
DVVMTQTPLSLSVSLGDQASISCRSSQSLVHSNGNTYLHWYLQKPGQSPKLLIYKVSYRF

SGVPDRFSGSGSGTDFTLKISRVEAEDLGVYFCSQNTHVPRTFGQG

>pVxK7b-037-hum01-LC
                                                    (SEQ ID NO: 8)
DIVMTQTPLSLPVTPGEPASISCRSSQSLVHSNGNTYLHWYQQKPGKAPKLLIYKVSYRF

SGVPDRFSGSGSGTDFTLKISRVEAEDVGVYYCSQNTHVPRTFGQG

>pVxK7b-037-hum02-LC
                                                    (SEQ ID NO: 9)
DVVMTQSPLSLPVTLGQPASISCRSSQSLVHSNGNTYLHWYQQKPGQAPRLLIYKVSYRF

SGVPSRFSGSGSGTEFTLTISSLQPDDFATYYCSQNTHVPRTFGQG

>pVxK7b-037-hum03-LC
                                                    (SEQ ID NO: 10)
DVVMTQSPLSLPVTLGQPASISCRSSQSLVHSNGNTYLHWYQQKPGKAPKLLIYKVSYRF

SGVPDRFSGSGSGTDFTLKISRVEAEDVGVYYCSQNTHVPRTFGQG

>pVxK7b-037-hum04-LC
                                                    (SEQ ID NO: 11)
DIQMTQSPSSLSASVGDRVTITCRSSQSLVHSNGNTYLHWYLQKPGQSPQLLIYKVSYRF

SGIPARFSGSGSGTEFTLTISSLQSEDFAVYYCSQNTHVPRTFGQG

>pVxK7b-037-hum05-LC
                                                    (SEQ ID NO: 12)
DIVMTQTPLSLPVTPGEPASISCRSSQSLVHSNGNTYLHWYLQKPGQSPQLLIYKVSYRF

SGVPDRFSGSGSGTDFTLKISRVEAEDVGVYYCSQNTHVPRTFGQG

>pVxK7b-037-hum06-LC
                                                    (SEQ ID NO: 13)
DIQMTQSPSSLSASVGDRVTITCRSSQSLVHSNGNTYLHWYLQKPGQSPQLLIYKVSYRF

SGIPARFSGSGSGTEFTLTISSLQSEDFAVYYCSQNTHVPRTFGQG
```

-continued

>pVxK7b-037-hum07-LC
(SEQ ID NO: 14)
DIVMTQTPLSLPVTPGEPASISCRSSQSLVHSNGNTYLHWYLQKPGQSPQLLIYKVSYRF
SGVPDRFSGSGSGTDFTLKISRVEAEDVGVYYCSQNTHVPRTFGQG >pVxK7b-037-hum08-LC
(SEQ ID NO: 15)
DIVMTQTPLSLPVTPGEPASISCRSSQSLVHSNGNTYLHWYQQKPGKAPKLLIYKVSYRF
SGVPDRFSGSGSGTDFTLKISRVEAEDVGVYYCSQNTHVPRTFGQG >pVxK7b-037-hum09-LC
(SEQ ID NO: 16)
DVVMTQSPLSLPVTLGQPASISCRSSQSLVHSNGNTYLHWYQQKPGKAPKLLIYKVSYRF
SGVPDRFSGSGSGTDFTLKISRVEAEDVGVYYCSQNTHVPRTFGQG >pVxK7b-037-hum10-LC
(SEQ ID NO: 17)
DIVMTQTPLSLPVTPGEPASISCRSSQSLVHSNGNTYLHWYLQKPGQSPQLLIYKVSYRF
SGVPDRFSGSGSGTDFTLKISRVEAEDVGVYYCSQNTHVPRTFGQG >pVxK7b-037-hum11-LC
(SEQ ID NO: 18)
EIVLTQSPATLSVSPGERATLSCRSSQSLVHSNGNTYLHWYQQKPGQAPRLLIYKVSYRF
SGVPSRFSGSGSGTDFTFTISSLEAEDAATYYCSQNTHVPRTFGQG >pVxK7b-037-hum12-LC
(SEQ ID NO: 19)
DIVMTQTPLSLPVTPGEPASISCRSSQSLVHSNGNTYLHWYQQKPGKAPKLLIYKVSYRF
SGVPDRFSGSGSGTDFTLKISRVEAEDVGVYYCSQNTHVPRTFGQG >pVxK7b-037-hum13-LC
(SEQ ID NO: 20)
DIVMTQTPLSLPVTPGEPASISCRSSQSLVHSNGNTYLHWYQQKPGKAPKLLIYKVSYRF
SGVPDRFSGSGSGTDFTLKISRVEAEDVGVYYCSQNTHVPRTFGQG >pVxK7b-037-hum14-LC
(SEQ ID NO: 21)
DVVMTQSPLSLPVTLGQPASISCRSSQSLVHSNGNTYLHWYQQKPGKAPKLLIYKVSYRF
SGVPDRFSGSGSGTDFTLKISRVEAEDVGVYYCSQNTHVPRTFGQG >pVxK7b-037-hum15-LC
(SEQ ID NO: 22)
AIQLTQSPSSLSASVGDRVTITCRSSQSLVHSNGNTYLHWYQQKPGQAPRLLIYKVSYRF
SGVPSRFSGSGSGTEFTLTISSLQPDDFATYYCSQNTHVPRTFGQG >pVxK7b-037-hum16-LC
(SEQ ID NO: 23)
AIQLTQSPSSLSASVGDRVTITCRSSQSLVHSNGNTYLHWYQQKPGQAPRLLIYKVSYRF
SGVPDRFSGSGSGTDFTLKISRVEAEDVGVYYCSQNTHVPRTFGQG >pVxK7b-037-hum17-LC
(SEQ ID NO: 24)
AIQLTQSPSSLSASVGDRVTITCRSSQSLVHSNGNTYLHWYQQKPGQAPRLLIYKVSYRF
SGVPDRFSGSGSGTDFTLKISRVEAEDVGVYYCSQNTHVPRTFGQG >pVxK7b-037-hum18-LC
(SEQ ID NO: 25)
EIVLTQSPATLSVSPGERATLSCRSSQSLVHSNGNTYLHWYQQKPGQAPRLLIYKVSYRF
SGVPSRFSGSGSGTDFTFTISSLEAEDAATYYCSQNTHVPRTFGQG >pVxK7b-037-hum19-LC
(SEQ ID NO: 26)
DVVMTQSPLSLPVTLGQPASISCRSSQSLVHSNGNTYLHWYQQKPGKAPKLLIYKVSYRF
SGVPDRFSGSGSGTDFTLKISRVEAEDVGVYYCSQNTHVPRTFGQG -continued >pVxK7b-037-hum20-LC
(SEQ ID NO: 27)
DIVMTQTPLSLPVTPGEPASISCRSSQSLVHSNGNTYLHWYLQKPGQSPQLLIYKVSYRF

SGVPDRFSGSGSGTDFTLKISRVEAEDVGVYYCSQNTHVPRTFGQG

>pVxK7b-037-hum21-LC
(SEQ ID NO: 28)
AIQLTQSPSSLSASVGDRVTITCRSSQSLVHSNGNTYLHWYQQKPGQAPRLLIYKVSYRF

SGVPDRFSGSGSGTDFTLKISRVEAEDVGVYYCSQNTHVPRTFGQG

>pVxK7b-037-hum22-LC
(SEQ ID NO: 29)
EIVLTQSPATLSVSPGERATLSCRSSQSLVHSNGNTYLHWYQQKPGQAPRLLIYKVSYRF

SGVPSRFSGSGSGTDFTFTISSLEAEDAATYYCSQNTHVPRTFGQG

>pVxK7b-037-hum23-LC
(SEQ ID NO: 30)
DIVMTQTPLSLPVTPGEPASISCRSSQSLVHSNGNTYLHWYQQKPGKAPKLLIYKVSYRF

SGVPDRFSGSGSGTDFTLKISRVEAEDVGVYYCSQNTHVPRTFGQG

>pVxK7b-037-hum24-LC
(SEQ ID NO: 31)
AIQLTQSPSSLSASVGDRVTITCRSSQSLVHSNGNTYLHWYQQKPGQAPRLLIYKVSYRF

SGVPSRFSGSGSGTEFTLTISSLQPDDFATYYCSQNTHVPRTFGQG

Light Chain Variable Region Nucleic Acid Sequences
>VxP037-01LC
(SEQ ID NO: 32)
GATGTTGTTATGACCCAAACTCCACTCTCCCTGTCTGTCAGTCTTGGAGATCAAGCCTCC

ATCTCTTGCAGATCTAGTCAGAGCCTTGTACACAGTAATGGAAACACCTATTTACATTGG

TACCTGCAGAAGCCAGGCCAGTCTCCAAAGCTCCTGATCTACAAAGTTTCCTACCGATTT

TCTGGGGTCCCAGACAGGTTCAGTGGCAGTGGATCAGGGACAGATTTCACACTCAAGATC

AGCAGAGTGGAGGCTGAGGATCTGGGAGTTTATTTCTGCTCTCAAAATACACATGTTCCT

CGGACGTTCGGCCAAGGAG

>pVxK7b-037-hum01-LC
(SEQ ID NO: 33)
GATATTGTGATGACCCAGACTCCACTCTCCCTGCCCGTCACCCCTGGAGAGCCGGCCTCC

ATCTCCTGCAGATCTAGTCAGAGCCTTGTACACAGTAATGGAAACACCTATTTACATTGG

TATCAGCAGAAACCAGGGAAAGCTCCTAAGCTCCTGATCTATAAAGTTTCCTACCGATTT

TCTGGGGTCCCAGACAGGTTCAGTGGCAGTGGGTCAGGCACTGATTTCACACTGAAAATC

AGCAGGGTGGAGGCTGAGGATGTTGGAGTTTATTACTGTTCTCAAAATACACATGTTCCT

CGGACGTTCGGCCAAGGG

>pVxK7b-037-hum02-LC
(SEQ ID NO: 34)
GATGTTGTGATGACTCAGTCTCCACTCTCCCTGCCCGTCACCCTTGGACAGCCGGCCTCC

ATCTCCTGCAGATCTAGTCAGAGCCTTGTACACAGTAATGGAAACACCTATTTACATTGG

TACCAGCAGAAACCTGGCCAGGCTCCCAGGCTCCTCATCTATAAAGTTTCCTACCGATTT

TCTGGGGTCCCATCAAGGTTCAGCGGCAGTGGATCTGGGACAGAATTCACTCTCACCATC

AGCAGCCTGCAGCCTGATGATTTTGCAACTTATTACTGTTCTCAAAATACACATGTTCCT

CGGACGTTCGGCCAAGGG

>pVxK7b-037-hum03-LC
(SEQ ID NO: 35)
GATGTTGTGATGACTCAGTCTCCACTCTCCCTGCCCGTCACCCTTGGACAGCCGGCCTCC

ATCTCCTGCAGATCTAGTCAGAGCCTTGTACACAGTAATGGAAACACCTATTTACATTGG

TATCAGCAGAAACCAGGGAAAGCTCCTAAGCTCCTGATCTATAAAGTTTCCTACCGATTT

```
TCTGGGGTCCCAGACAGGTTCAGTGGCAGTGGGTCAGGCACTGATTTCACACTGAAAATC

AGCAGGGTGGAGGCTGAGGATGTTGGAGTTTATTACTGTTCTCAAAATACACATGTTCCT

CGGACGTTCGGCCAAGGG

>pVxK7b-037-hum04-LC
                                                      (SEQ ID NO: 36)
GACATCCAGATGACCCAGTCTCCATCCTCCCTGTCTGCATCTGTAGGAGACAGAGTCACC

ATCACTTGCAGATCTAGTCAGAGCCTTGTACACAGTAATGGAAACACCTATTTACATTGG

TACCTGCAGAAGCCAGGGCAGTCTCCACAGCTCCTGATCTATAAAGTTTCCTACCGATTT

TCTGGGATCCCAGCCAGGTTCAGTGGCAGTGGGTCTGGGACAGAGTTCACTCTCACCATC

AGCAGCCTGCAGTCTGAAGATTTTGCAGTTTATTACTGTTCTCAAAATACACATGTTCCT

CGGACGTTCGGCCAAGGG

>pVxK7b-037-hum05-LC
                                                      (SEQ ID NO: 37)
GATATTGTGATGACCCAGACTCCACTCTCCCTGCCCGTCACCCCTGGAGAGCCGGCCTCC

ATCTCCTGCAGATCTAGTCAGAGCCTTGTACACAGTAATGGAAACACCTATTTACATTGG

TACCTGCAGAAGCCAGGGCAGTCTCCACAGCTCCTGATCTATAAAGTTTCCTACCGATTT

TCTGGGGTCCCAGACAGGTTCAGTGGCAGTGGGTCAGGCACTGATTTCACACTGAAAATC

AGCAGGGTGGAGGCTGAGGATGTTGGAGTTTATTACTGTTCTCAAAATACACATGTTCCT

CGGACGTTCGGCCAAGGG

>pVxK7b-037-hum06-LC
                                                      (SEQ ID NO: 38)
GACATCCAGATGACCCAGTCTCCATCCTCCCTGTCTGCATCTGTAGGAGACAGAGTCACC

ATCACTTGCAGATCTAGTCAGAGCCTTGTACACAGTAATGGAAACACCTATTTACATTGG

TACCTGCAGAAGCCAGGGCAGTCTCCACAGCTCCTGATCTATAAAGTTTCCTACCGATTT

TCTGGGATCCCAGCCAGGTTCAGTGGCAGTGGGTCTGGGACAGAGTTCACTCTCACCATC

AGCAGCCTGCAGTCTGAAGATTTTGCAGTTTATTACTGTTCTCAAAATACACATGTTCCT

CGGACGTTCGGCCAAGGG

>pVxK7b-037-hum07-LC
                                                      (SEQ ID NO: 39)
GATATTGTGATGACCCAGACTCCACTCTCCCTGCCCGTCACCCCTGGAGAGCCGGCCTCC

ATCTCCTGCAGATCTAGTCAGAGCCTTGTACACAGTAATGGAAACACCTATTTACATTGG

TACCTGCAGAAGCCAGGGCAGTCTCCACAGCTCCTGATCTATAAAGTTTCCTACCGATTT

TCTGGGGTCCCAGACAGGTTCAGTGGCAGTGGGTCAGGCACTGATTTCACACTGAAAATC

AGCAGGGTGGAGGCTGAGGATGTTGGAGTTTATTACTGTTCTCAAAATACACATGTTCCT

CGGACGTTCGGCCAAGGG

>pVxK7b-037-hum08-LC
                                                      (SEQ ID NO: 40)
GATATTGTGATGACCCAGACTCCACTCTCCCTGCCCGTCACCCCTGGAGAGCCGGCCTCC

ATCTCCTGCAGATCTAGTCAGAGCCTTGTACACAGTAATGGAAACACCTATTTACATTGG

TATCAGCAGAAACCAGGGAAAGCTCCTAAGCTCCTGATCTATAAAGTTTCCTACCGATTT

TCTGGGGTCCCAGACAGGTTCAGTGGCAGTGGGTCAGGCACTGATTTCACACTGAAAATC

AGCAGGGTGGAGGCTGAGGATGTTGGAGTTTATTACTGTTCTCAAAATACACATGTTCCT

CGGACGTTCGGCCAAGGG
```

>pVxK7b-037-hum09-LC (SEQ ID NO: 41)
GATGTTGTGATGACTCAGTCTCCACTCTCCCTGCCCGTCACCCTTGGACAGCCGGCCTCC
ATCTCCTGCAGATCTAGTCAGAGCCTTGTACACAGTAATGGAAACACCTATTTACATTGG
TATCAGCAGAAACCAGGGAAAGCTCCTAAGCTCCTGATCTATAAAGTTTCCTACCGATTT
TCTGGGGTCCCAGACAGGTTCAGTGGCAGTGGGTCAGGCACTGATTTCACACTGAAAATC
AGCAGGGTGGAGGCTGAGGATGTTGGAGTTTATTACTGTTCTCAAAATACACATGTTCCT
CGGACGTTCGGCCAAGGG >pVxK7b-037-hum10-LC (SEQ ID NO: 42)
GATATTGTGATGACCCAGACTCCACTCTCCCTGCCCGTCACCCCTGGAGAGCCGGCCTCC
ATCTCCTGCAGATCTAGTCAGAGCCTTGTACACAGTAATGGAAACACCTATTTACATTGG
TACCTGCAGAAGCCAGGGCAGTCTCCACAGCTCCTGATCTATAAAGTTTCCTACCGATTT
TCTGGGGTCCCAGACAGGTTCAGTGGCAGTGGGTCAGGCACTGATTTCACACTGAAAATC
AGCAGGGTGGAGGCTGAGGATGTTGGAGTTTATTACTGTTCTCAAAATACACATGTTCCT
CGGACGTTCGGCCAAGGG >pVxK7b-037-hum11-LC (SEQ ID NO: 43)
GAAATTGTGTTGACACAGTCTCCAGCCACCCTGTCTGTGTCTCCAGGGGAAAGAGCCACC
CTCTCCTGCAGATCTAGTCAGAGCCTTGTACACAGTAATGGAAACACCTATTTACATTGG
TACCAGCAGAAACCTGGCCAGGCTCCCAGGCTCCTCATCTATAAAGTTTCCTACCGATTT
TCTGGGGTCCCCTCGAGGTTCAGTGGCAGTGGATCTGGGACAGATTTCACCTTTACCATC
AGTAGCCTGGAAGCTGAAGATGCTGCAACATATTACTGTTCTCAAAATACACATGTTCCT
CGGACGTTCGGCCAAGGG >pVxK7b-037-hum12-LC (SEQ ID NO: 44)
GATATTGTGATGACCCAGACTCCACTCTCCCTGCCCGTCACCCCTGGAGAGCCGGCCTCC
ATCTCCTGCAGATCTAGTCAGAGCCTTGTACACAGTAATGGAAACACCTATTTACATTGG
TATCAGCAGAAACCAGGGAAAGCTCCTAAGCTCCTGATCTATAAAGTTTCCTACCGATTT
TCTGGGGTCCCAGACAGGTTCAGTGGCAGTGGGTCAGGCACTGATTTCACACTGAAAATC
AGCAGGGTGGAGGCTGAGGATGTTGGAGTTTATTACTGTTCTCAAAATACACATGTTCCT
CGGACGTTCGGCCAAGGG >pVxK7b-037-hum13-LC (SEQ ID NO: 45)
GATATTGTGATGACCCAGACTCCACTCTCCCTGCCCGTCACCCCTGGAGAGCCGGCCTCC
ATCTCCTGCAGATCTAGTCAGAGCCTTGTACACAGTAATGGAAACACCTATTTACATTGG
TATCAGCAGAAACCAGGGAAAGCTCCTAAGCTCCTGATCTATAAAGTTTCCTACCGATTT
TCTGGGGTCCCAGACAGGTTCAGTGGCAGTGGGTCAGGCACTGATTTCACACTGAAAATC
AGCAGGGTGGAGGCTGAGGATGTTGGAGTTTATTACTGTTCTCAAAATACACATGTTCCT
CGGACGTTCGGCCAAGGG >pVxK7b-037-hum14-LC (SEQ ID NO: 46)
GATGTTGTGATGACTCAGTCTCCACTCTCCCTGCCCGTCACCCTTGGACAGCCGGCCTCC
ATCTCCTGCAGATCTAGTCAGAGCCTTGTACACAGTAATGGAAACACCTATTTACATTGG
TATCAGCAGAAACCAGGGAAAGCTCCTAAGCTCCTGATCTATAAAGTTTCCTACCGATTT
TCTGGGGTCCCAGACAGGTTCAGTGGCAGTGGGTCAGGCACTGATTTCACACTGAAAATC -continued

AGCAGGGTGGAGGCTGAGGATGTTGGAGTTTATTACTGTTCTCAAAATACACATGTTCCT

CGGACGTTCGGCCAAGGG

>pVxK7b-037-hum15-LC
(SEQ ID NO: 47)
GCCATCCAGTTGACCCAGTCTCCATCCTCCCTGTCTGCATCTGTAGGAGACAGAGTCACC

ATCACTTGCAGATCTAGTCAGAGCCTTGTACACAGTAATGGAAACACCTATTTACATTGG

TACCAGCAGAAACCTGGCCAGGCTCCCAGGCTCCTCATCTATAAAGTTTCCTACCGATTT

TCTGGGGTCCCATCAAGGTTCAGCGGCAGTGGATCTGGGACAGAATTCACTCTCACCATC

AGCAGCCTGCAGCCTGATGATTTTGCAACTTATTACTGTTCTCAAAATACACATGTTCCT

CGGACGTTCGGCCAAGGG

>pVxK7b-037-hum16-LC
(SEQ ID NO: 48)
GCCATCCAGTTGACCCAGTCTCCATCCTCCCTGTCTGCATCTGTAGGAGACAGAGTCACC

ATCACTTGCAGATCTAGTCAGAGCCTTGTACACAGTAATGGAAACACCTATTTACATTGG

TACCAGCAGAAACCTGGCCAGGCTCCCAGGCTCCTCATCTATAAAGTTTCCTACCGATTT

TCTGGGGTCCCAGACAGGTTCAGTGGCAGTGGGTCAGGCACTGATTTCACACTGAAAATC

AGCAGGGTGGAGGCTGAGGATGTTGGAGTTTATTACTGTTCTCAAAATACACATGTTCCT

CGGACGTTCGGCCAAGGG

>pVxK7b-037-hum17-LC
(SEQ ID NO: 49)
GCCATCCAGTTGACCCAGTCTCCATCCTCCCTGTCTGCATCTGTAGGAGACAGAGTCACC

ATCACTTGCAGATCTAGTCAGAGCCTTGTACACAGTAATGGAAACACCTATTTACATTGG

TACCAGCAGAAACCTGGCCAGGCTCCCAGGCTCCTCATCTATAAAGTTTCCTACCGATTT

TCTGGGGTCCCAGACAGGTTCAGTGGCAGTGGGTCAGGCACTGATTTCACACTGAAAATC

AGCAGGGTGGAGGCTGAGGATGTTGGAGTTTATTACTGTTCTCAAAATACACATGTTCCT

CGGACGTTCGGCCAAGGG

>pVxK7b-037-hum18-LC
(SEQ ID NO: 50)
GAAATTGTGTTGACACAGTCTCCAGCCACCCTGTCTGTGTCTCCAGGGGAAAGAGCCACC

CTCTCCTGCAGATCTAGTCAGAGCCTTGTACACAGTAATGGAAACACCTATTTACATTGG

TACCAGCAGAAACCTGGCCAGGCTCCCAGGCTCCTCATCTATAAAGTTTCCTACCGATTT

TCTGGGGTCCCCTCGAGGTTCAGTGGCAGTGGATCTGGGACAGATTTCACCTTTACCATC

AGTAGCCTGGAAGCTGAAGATGCTGCAACATATTACTGTTCTCAAAATACACATGTTCCT

CGGACGTTCGGCCAAGGG

>pVxK7b-037-hum19-LC
(SEQ ID NO: 51)
GATGTTGTGATGACTCAGTCTCCACTCTCCCTGCCCGTCACCCTTGGACAGCCGGCCTCC

ATCTCCTGCAGATCTAGTCAGAGCCTTGTACACAGTAATGGAAACACCTATTTACATTGG

TATCAGCAGAAACCAGGGAAAGCTCCTAAGCTCCTGATCTATAAAGTTTCCTACCGATTT

TCTGGGGTCCCAGACAGGTTCAGTGGCAGTGGGTCAGGCACTGATTTCACACTGAAAATC

AGCAGGGTGGAGGCTGAGGATGTTGGAGTTTATTACTGTTCTCAAAATACACATGTTCCT

CGGACGTTCGGCCAAGGG

>pVxK7b-037-hum20-LC
(SEQ ID NO: 52)
GATATTGTGATGACCCAGACTCCACTCTCCCTGCCCGTCACCCCTGGAGAGCCGGCCTCC

ATCTCCTGCAGATCTAGTCAGAGCCTTGTACACAGTAATGGAAACACCTATTTACATTGG

TACCTGCAGAAGCCAGGGCAGTCTCCACAGCTCCTGATCTATAAAGTTTCCTACCGATTT

-continued

TCTGGGGTCCCAGACAGGTTCAGTGGCAGTGGGTCAGGCACTGATTTCACACTGAAAATC

AGCAGGGTGGAGGCTGAGGATGTTGGAGTTTATTACTGTTCTCAAAATACACATGTTCCT

CGGACGTTCGGCCAAGGG

```
>pVxK7b-037-hum21-LC
                                                 (SEQ ID NO: 53)
```
GCCATCCAGTTGACCCAGTCTCCATCCTCCCTGTCTGCATCTGTAGGAGACAGAGTCACC

ATCACTTGCAGATCTAGTCAGAGCCTTGTACACAGTAATGGAAACACCTATTTACATTGG

TACCAGCAGAAACCTGGCCAGGCTCCCAGGCTCCTCATCTATAAAGTTTCCTACCGATTT

TCTGGGGTCCCAGACAGGTTCAGTGGCAGTGGGTCAGGCACTGATTTCACACTGAAAATC

AGCAGGGTGGAGGCTGAGGATGTTGGAGTTTATTACTGTTCTCAAAATACACATGTTCCT

CGGACGTTCGGCCAAGGG

```
>pVxK7b-037-hum22-LC
                                                 (SEQ ID NO: 54)
```
GAAATTGTGTTGACACAGTCTCCAGCCACCCTGTCTGTGTCTCCAGGGGAAAGAGCCACC

CTCTCCTGCAGATCTAGTCAGAGCCTTGTACACAGTAATGGAAACACCTATTTACATTGG

TACCAGCAGAAACCTGGCCAGGCTCCCAGGCTCCTCATCTATAAAGTTTCCTACCGATTT

TCTGGGGTCCCCTCGAGGTTCAGTGGCAGTGGATCTGGGACAGATTTCACCTTTACCATC

AGTAGCCTGGAAGCTGAAGATGCTGCAACATATTACTGTTCTCAAAATACACATGTTCCT

CGGACGTTCGGCCAAGGG

```
>pVxK7b-037-hum23-LC
                                                 (SEQ ID NO: 55)
```
GATATTGTGATGACCCAGACTCCACTCTCCCTGCCCGTCACCCCTGGAGAGCCGGCCTCC

ATCTCCTGCAGATCTAGTCAGAGCCTTGTACACAGTAATGGAAACACCTATTTACATTGG

TATCAGCAGAAACCAGGGAAAGCTCCTAAGCTCCTGATCTATAAAGTTTCCTACCGATTT

TCTGGGGTCCCAGACAGGTTCAGTGGCAGTGGGTCAGGCACTGATTTCACACTGAAAATC

AGCAGGGTGGAGGCTGAGGATGTTGGAGTTTATTACTGTTCTCAAAATACACATGTTCCT

CGGACGTTCGGCCAAGGG

```
>pVxK7b-037-hum24-LC
                                                 (SEQ ID NO: 56)
```
GCCATCCAGTTGACCCAGTCTCCATCCTCCCTGTCTGCATCTGTAGGAGACAGAGTCACC

ATCACTTGCAGATCTAGTCAGAGCCTTGTACACAGTAATGGAAACACCTATTTACATTGG

TACCAGCAGAAACCTGGCCAGGCTCCCAGGCTCCTCATCTATAAAGTTTCCTACCGATTT

TCTGGGGTCCCATCAAGGTTCAGCGGCAGTGGATCTGGGACAGAATTCACTCTCACCATC

AGCAGCCTGCAGCCTGATGATTTTGCAACTTATTACTGTTCTCAAAATACACATGTTCCT

CGGACGTTCGGCCAAGGG

```
Heavy Chain Variable Region Amino Acid Sequences
>VxP037-01HC
                                                 (SEQ ID NO: 57)
```
EVQLQQFGAELVKPGASMKLSCKASGYTFTNYYVFWVKQRPGQGLEWIGDINPVNGDTNF

NEKFKNKATLTVDKSSTTTYLQLSSLTSEDSAVYYCTRGGYTMDYWGQG

```
>pVxK7b-037-hum01-HC
                                                 (SEQ ID NO: 58)
```
QVQLQESGPGLVKPSQTLSLTCTVSGYTFTNYYVFWVRQARGQRLEWIGDINPVNGDTNF

NEKFKNRVTISADKSISTAYLQWSSLKASDTAMYYCARGGYTMDYWGQG

```
>pVxK7b-037-hum02-HC
                                                 (SEQ ID NO: 59)
```
QVQLQESGPGLVKPSQTLSLTCTVSGYTFTNYYVFWVRQARGQRLEWIGDINPVNGDTNF

NEKFKNRVTISADKSISTAYLQWSSLKASDTAMYYCARGGYTMDYWGQG

-continued

>pVxK7b-037-hum03-HC
(SEQ ID NO: 60)
EVQLVQSGAEVKKPGESLRISCKGSGYTFTNYYVFWVRQARGQRLEWIGDINPVNGDTNF

NEKFKNRVTITADKSTSTAYMELSSLRSEDTAVYYCARGGYTMDYWGQG

>pVxK7b-037-hum04-HC
(SEQ ID NO: 61)
QVQLQESGPGLVKPSQTLSLTCTVSGYTFTNYYVFWVRQAPGKGLEWVSDINPVNGDTNF

NEKFKNRVTISVDTSKNQFSLKLSSVTAADTAVYYCARGGYTMDYWGQG

>pVxK7b-037-hum05-HC
(SEQ ID NO: 62)
QVQLQESGPGINKPSQTLSLTCTVSGYTFTNYYVFWVRQAPGKGLEWVSDINPVNGDTNF

NEKFKNRVTISVDTSKNQFSLKLSSVTAADTAVYYCARGGYTMDYWGQG

>pVxK7b-037-hum06-HC
(SEQ ID NO: 63)
QVQLQESGPGLVKPSQTLSLTCTVSGYTFTNYYVFWVRQARGQRLEWIGDINPVNGDTNF

NEKFKNRLTISKDTSKNQVVLTMTNMDPVDTATYYCARGGYTMDYWGQG

>pVxK7b-037-hum07-HC
(SEQ ID NO: 64)
QVQLQESGPGLVKPGATVKISCKVSGYTFTNYYVFWVRQARGQRLEWIGDINPVNGDTNF

NEKFKNRVTITADKSTSTAYMELSSLRSEDTAVYYCARGGYTMDYWGQG

>pVxK7b-037-hum08-HC
(SEQ ID NO: 65)
QITLKESGPTLVKPTQTLTLTCTFSGYTFTNYYVFWIRQSPSRGLEWLGDINPVNGDTNF

NEKFKNRFTISRDNAKNSLYLQMNSLRAEDTAVYYCARGGYTMDYWGQG

>pVxK7b-037-hum09-HC
(SEQ ID NO: 66)
QVQLQESGPGLVKPSQTLSLTCTVSGYTFTNYYVFWVRQARGQRLEWIGDINPVNGDTNF

NEKFKNRLTISKDTSKNQVVLTMTNMDPVDTATYYCARGGYTMDYWGQG

>pVxK7b-037-hum10-HC
(SEQ ID NO: 67)
QVQLQESGPGLVKPSQTLSLTCTVSGYTFTNYYVFWVRQARGQRLEWIGDINPVNGDTNF

NEKFKNRLTISKDTSKNQVVLTMINMDPVDTATYYCARGGYTMDYWGQG

>pVxK7b-037-hum11-HC
(SEQ ID NO: 68)
QVQLQESGPGINKPGATVKISCKVSGYTFTNYYVFWVRQARGQRLEWIGDINPVNGDTNF

NEKFKNRVTITADKSTSTAYMELSSLRSEDTAVYYCARGGYTMDYWGQG

>pVxK7b-037-hum12-HC
(SEQ ID NO: 69)
QVQLQESGPGLVKPGATVKISCKVSGYTFTNYYVFWVRQARGQRLEWIGDINPVNGDTNF

NEKFKNRVTITADKSTSTAYMELSSLRSEDTAVYYCARGGYTMDYWGQG

>pVxK7b-037-hum13-HC
(SEQ ID NO: 70)
EVQLVQSGAEVKKPGESLRISCKGSGYTFTNYYVFWIRQSPSRGLEWLGDINPVNGDTNF

NEKFKNRVTITADKSTSTAYMELSSLRSEDTAVYYCARGGYTMDYWGQG

>pVxK7b-037-hum14-HC
(SEQ ID NO: 71)
QVQLQESGPGLVKPSQTLSLTCTVSGYTFTNYYVFWVRQARGQRLEWIGDINPVNGDTNF

NEKFKNRVTISADKSISTAYLQWSSLKASDTAMYYCARGGYTMDYWGQG

>pVxK7b-037-hum15-HC
(SEQ ID NO: 72)
QVQLQESGPGLVKPSQTLSLTCTVSGYTFTNYYVFWVRQARGQRLEWIGDINPVNGDTNF

NEKFKNRLTISKDTSKNQVVLTMTNMDPVDTATYYCARGGYTMDYWGQG

>pVxK7b-037-hum16-HC (SEQ ID NO: 73)
QVQLQESGPGLVKPSQTLSLTCTVSGYTFTNYYVFWVRQARGQRLEWIGDINPVNGDTNF

NEKFKNRVTISADKSISTAYLQWSSLKASDTAMYYCARGGYTMDYWGQG

>pVxK7b-037-hum17-HC (SEQ ID NO: 74)
EVQLVQSGAEVKKPGATVKISCKVSGYTFTNYYVFWIRQPPGKGLEWIGDINPVNGDTNF

NEKFKNRVTITADKSTSTAYMELSSLRSEDTAVYYCARGGYTMDYWGQG

>pVxK7b-037-hum18-HC (SEQ ID NO: 75)
EVQLVQSGAEVKKPGESLRISCKGSGYTFTNYYVFWIRQSPSRGLEWLGDINPVNGDTNF

NEKFKNRVTITADKSTSTAYMELSSLRSEDTAVYYCARGGYTMDYWGQG

>pVxK7b-037-hum19-HC (SEQ ID NO: 76)
EVQLVQSGAEVKKPGESLRISCKGSGYTFTNYYVFWIRQSPSRGLEWLGDINPVNGDTNF

NEKFKNRVTITADKSTSTAYMELSSLRSEDTAVYYCARGGYTMDYWGQG

>pVxK7b-037-hum20-HC (SEQ ID NO: 77)
QITLKESGPTLVKPTQTLTLTCTFSGYTFTNYYVFWVRQAPGQGLEWMGDINPVNGDTNF

NEKFKNRVTITADKSTSTAYMELSSLRSEDTAVYYCARGGYTMDYWGQG

>pVxK7b-037-hum21-HC (SEQ ID NO: 78)
QVQLQESGPGLVKPSQTLSLTCTVSGYTFTNYYVFWVRQARGQRLEWIGDINPVNGDTNF

NEKFKNRLTISKDTSKNQVVLTMTNMDPVDTATYYCARGGYTMDYWGQG

>pVxK7b-037-hum22-HC (SEQ ID NO: 79)
QVQLQESGPGLVKPSQTLSLICTVSGYTFTNYYVFWVRQARGQRLEWIGDINPVNGDTNF

NEKFKNRLTISKDTSKNQVVLTMTNMDPVDTATYYCARGGYTMDYWGQG

>pVxK7b-037-hum23-HC (SEQ ID NO: 80)
QVQLQESGPGLVKPSQTLSLTCTVSGYTFTNYYVFWVRQARGQRLEWIGDINPVNGDTNF

NEKFKNRLTISKDTSKNQVVLTMTNMDPVDTATYYCARGGYTMDYWGQG

>pVxK7b-037-hum24-HC (SEQ ID NO: 81)
QVQLQESGPGLVKPGATVKISCKVSGYTFTNYYVFWVRQARGQRLEWIGDINPVNGDTNF

NEKFKNRVTITADKSTSTAYMELSSLRSEDTAVYYCARGGYTMDYWGQG

Heavy Chain Variable Region Nucleic Acid Sequences
>VxP037-01HC (SEQ ID NO: 82)
GAGGTCCAGCTGCAGCAGTTTGGGGCTGAACTGGTGAAGCCTGGGGCTTCAATGAAGTTG

TCCTGCAAGGCTTCTGGCTACACCTTCACCAACTACTATGTATTCTGGGTGAAACAGAGG

CCTGGACAAGGCCTTGAGTGGATTGGAGACATTAATCCTGTCAATGGTGATACTAACTTC

AATGAGAAATTCAAGAACAAGGCCACACTGACTGTAGACAAGTCCTCCACCACAACATAC

TTGCAACTCAGCAGCCTGACATCTGAGGACTCTGCGGTCTATTACTGTACAAGAGGGGGT

TATACTATGGACTACTGGGGTCAAGGA

>pVxK7b-037-hum01-HC (SEQ ID NO: 83)
CAGGTGCAGCTGCAGGAGTCGGGCCCAGGACTGGTGAAGCCTTCACAGACCCTGTCCCTC

ACCTGCACTGTCTCTGGCTACACCTTCACCAACTACTATGTATTCTGGGTGCGACAGGCT

CGTGGACAACGCCTTGAGTGGATAGGTGACATTAATCCTGTCAATGGTGATACTAACTTC

AATGAGAAATTCAAGAACAGAGTCACCATCTCAGCCGACAAGTCCATCAGCACCGCCTAC

-continued

CTGCAGTGGAGCAGCCTGAAGGCCTCGGACACCGCCATGTATTACTGTGCGAGAGGGGGT

TATACTATGGACTACTGGGGCCAGGGA

>pVxK7b-037-hum02-HC
(SEQ ID NO: 84)
CAGGTGCAGCTGCAGGAGTCGGGCCCAGGACTGGTGAAGCCTTCACAGACCCTGTCCCTC

ACCTGCACTGTCTCTGGCTACACCTTCACCAACTACTATGTATTCTGGGTGCGACAGGCT

CGTGGACAACGCCTTGAGTGGATAGGTGACATTAATCCTGTCAATGGTGATACTAACTTC

AATGAGAAATTCAAGAACAGAGTCACCATCTCAGCCGACAAGTCCATCAGCACCGCCTAC

CTGCAGTGGAGCAGCCTGAAGGCCTCGGACACCGCCATGTATTACTGTGCGAGAGGGGGT

TATACTATGGACTACTGGGGCCAGGGA

>pVxK7b-037-hum03-HC
(SEQ ID NO: 85)
GAAGTGCAGCTGGTGCAGTCTGGAGCAGAGGTGAAAAAGCCCGGGGAGTCTCTGAGGATC

TCCTGTAAGGGTTCTGGCTACACCTTCACCAACTACTATGTATTCTGGGTGCGACAGGCT

CGTGGACAACGCCTTGAGTGGATAGGTGACATTAATCCTGTCAATGGTGATACTAACTTC

AATGAGAAATTCAAGAACAGAGTCACGATTACCGCGGACAAATCCACGAGCACAGCCTAC

ATGGAGCTGAGCAGCCTGAGATCTGAGGACACGGCCGTGTATTACTGTGCGAGAGGGGGT

TATACTATGGACTACTGGGGCCAGGGA

>pVxK7b-037-hum04-HC
(SEQ ID NO: 86)
CAGGTGCAGCTGCAGGAGTCGGGCCCAGGACTGGTGAAGCCTTCACAGACCCTGTCCCTC

ACCTGCACTGTCTCTGGCTACACCTTCACCAACTACTATGTATTCTGGGTCCGCCAGGCT

CCAGGGAAGGGGCTGGAGTGGGTCAGTGACATTAATCCTGTCAATGGTGATACTAACTTC

AATGAGAAATTCAAGAACAGAGTCACCATATCAGTAGACACGTCCAAGAACCAGTTCTCC

CTGAAGCTGAGCTCTGTGACCGCCGCGGACACGGCTGTGTATTACTGTGCGAGAGGGGGT

TATACTATGGACTACTGGGGCCAGGGA

>pVxK7b-037-hum05-HC
(SEQ ID NO: 87)
CAGGTGCAGCTGCAGGAGTCGGGCCCAGGACTGGTGAAGCCTTCACAGACCCTGTCCCTC

ACCTGCACTGTCTCTGGCTACACCTTCACCAACTACTATGTATTCTGGGTCCGCCAGGCT

CCAGGGAAGGGGCTGGAGTGGGTCAGTGACATTAATCCTGTCAATGGTGATACTAACTTC

AATGAGAAATTCAAGAACAGAGTCACCATATCAGTAGACACGTCCAAGAACCAGTTCTCC

CTGAAGCTGAGCTCTGTGACCGCCGCGGACACGGCTGTGTATTACTGTGCGAGAGGGGGT

TATACTATGGACTACTGGGGCCAGGGA

>pVxK7b-037-hum06-HC
(SEQ ID NO: 88)
CAGGTGCAGCTGCAGGAGTCGGGCCCAGGACTGGTGAAGCCTTCACAGACCCTGTCCCTC

ACCTGCACTGTCTCTGGCTACACCTTCACCAACTACTATGTATTCTGGGTGCGACAGGCT

CGTGGACAACGCCTTGAGTGGATAGGTGACATTAATCCTGTCAATGGTGATACTAACTTC

AATGAGAAATTCAAGAACAGACTCACCATCTCCAAGGACACCTCCAAAAACCAGGTGGTC

CTTACAATGACCAACATGGACCCTGTGGACACAGCCACGTATTACTGTGCAAGAGGGGGT

TATACTATGGACTACTGGGGCCAGGGA

>pVxK7b-037-hum07-HC
(SEQ ID NO: 89)
CAGGTGCAGCTGCAGGAGTCGGGCCCAGGACTGGTGAAGCCTGGGGCTACAGTGAAAATC

TCCTGCAAGGTTTCTGGCTACACCTTCACCAACTACTATGTATTCTGGGTGCGACAGGCT

-continued

CGTGGACAACGCCTTGAGTGGATAGGTGACATTAATCCTGTCAATGGTGATACTAACTTC

AATGAGAAATTCAAGAACAGAGTCACGATTACCGCGGACAAATCCACGAGCACAGCCTAC

ATGGAGCTGAGCAGCCTGAGATCTGAGGACACGGCCGTGTATTACTGTGCGAGAGGGGGT

TATACTATGGACTACTGGGGCCAGGGA

>pVxK7b-037-hum08-HC
(SEQ ID NO: 90)
CAGATCACCTTGAAGGAGTCTGGTCCTACGCTGGTGAAACCCACACAGACCCTCACGCTG

ACCTGCACCTTCTCTGGCTACACCTTCACCAACTACTATGTATTCTGGATCAGGCAGTCC

CCATCGAGAGGCCTTGAGTGGCTGGGTGACATTAATCCTGTCAATGGTGATACTAACTTC

AATGAGAAATTCAAGAACAGATTCACCATCTCCAGAGACAACGCCAAGAACTCACTGTAT

CTGCAAATGAACAGCCTGAGAGCCGAGGACACGGCTGTGTATTACTGTGCGAGAGGGGGT

TATACTATGGACTACTGGGGCCAGGGA

>pVxK7b-037-hum09-HC
(SEQ ID NO: 91)
CAGGTGCAGCTGCAGGAGTCGGGCCCAGGACTGGTGAAGCCTTCACAGACCCTGTCCCTC

ACCTGCACTGTCTCTGGCTACACCTTCACCAACTACTATGTATTCTGGGTGCGACAGGCT

CGTGGACAACGCCTTGAGTGGATAGGTGACATTAATCCTGTCAATGGTGATACTAACTTC

AATGAGAAATTCAAGAACAGACTCACCATCTCCAAGGACACCTCCAAAAACCAGGTGGTC

CTTACAATGACCAACATGGACCCTGTGGACACAGCCACGTATTACTGTGCAAGAGGGGGT

TATACTATGGACTACTGGGGCCAGGGA

>pVxK7b-037-hum10-HC
(SEQ ID NO: 92)
CAGGTGCAGCTGCAGGAGTCGGGCCCAGGACTGGTGAAGCCTTCACAGACCCTGTCCCTC

ACCTGCACTGTCTCTGGCTACACCTTCACCAACTACTATGTATTCTGGGTGCGACAGGCT

CGTGGACAACGCCTTGAGTGGATAGGTGACATTAATCCTGTCAATGGTGATACTAACTTC

AATGAGAAATTCAAGAACAGACTCACCATCTCCAAGGACACCTCCAAAAACCAGGTGGTC

CTTACAATGACCAACATGGACCCTGTGGACACAGCCACGTATTACTGTGCAAGAGGGGGT

TATACTATGGACTACTGGGGCCAGGGA

>pVxK7b-037-hum11-HC
(SEQ ID NO: 93)
CAGGTGCAGCTGCAGGAGTCGGGCCCAGGACTGGTGAAGCCTGGGGCTACAGTGAAAATC

TCCTGCAAGGTTTCTGGCTACACCTTCACCAACTACTATGTATTCTGGGTGCGACAGGCT

CGTGGACAACGCCTTGAGTGGATAGGTGACATTAATCCTGTCAATGGTGATACTAACTTC

AATGAGAAATTCAAGAACAGAGTCACGATTACCGCGGACAAATCCACGAGCACAGCCTAC

ATGGAGCTGAGCAGCCTGAGATCTGAGGACACGGCCGTGTATTACTGTGCGAGAGGGGGT

TATACTATGGACTACTGGGGCCAGGGA

>pVxK7b-037-hum12-HC
(SEQ ID NO: 94)
CAGGTGCAGCTGCAGGAGTCGGGCCCAGGACTGGTGAAGCCTGGGGCTACAGTGAAAATC

TCCTGCAAGGTTTCTGGCTACACCTTCACCAACTACTATGTATTCTGGGTGCGACAGGCT

CGTGGACAACGCCTTGAGTGGATAGGTGACATTAATCCTGTCAATGGTGATACTAACTTC

AATGAGAAATTCAAGAACAGAGTCACGATTACCGCGGACAAATCCACGAGCACAGCCTAC

ATGGAGCTGAGCAGCCTGAGATCTGAGGACACGGCCGTGTATTACTGTGCGAGAGGGGGT

TATACTATGGACTACTGGGGCCAGGGA

>pVxK7b-037-hum13-HC (SEQ ID NO: 95)
GAAGTGCAGCTGGTGCAGTCTGGAGCAGAGGTGAAAAAGCCCGGGGAGTCTCTGAGGATC

TCCTGTAAGGGTTCTGGCTACACCTTCACCAACTACTATGTATTCTGGATCAGGCAGTCC

CCATCGAGAGGCCTTGAGTGGCTGGGTGACATTAATCCTGTCAATGGTGATACTAACTTC

AATGAGAAATTCAAGAACAGAGTCACGATTACCGCGGACAAATCCACGAGCACAGCCTAC

ATGGAGCTGAGCAGCCTGAGATCTGAGGACACGGCCGTGTATTACTGTGCGAGAGGGGGT

TATACTATGGACTACTGGGGCCAGGGA

>pVxK7b-037-hum14-HC (SEQ ID NO: 96)
CAGGTGCAGCTGCAGGAGTCGGGCCCAGGACTGGTGAAGCCTTCACAGACCCTGTCCCTC

ACCTGCACTGTCTCTGGCTACACCTTCACCAACTACTATGTATTCTGGGTGCGACAGGCT

CGTGGACAACGCCTTGAGTGGATAGGTGACATTAATCCTGTCAATGGTGATACTAACTTC

AATGAGAAATTCAAGAACAGAGTCACCATCTCAGCCGACAAGTCCATCAGCACCGCCTAC

CTGCAGTGGAGCAGCCTGAAGGCCTCGGACACCGCCATGTATTACTGTGCGAGAGGGGGT

TATACTATGGACTACTGGGGCCAGGGA

>pVxK7b-037-hum15-HC (SEQ ID NO: 97)
CAGGTGCAGCTGCAGGAGTCGGGCCCAGGACTGGTGAAGCCTTCACAGACCCTGTCCCTC

ACCTGCACTGTCTCTGGCTACACCTTCACCAACTACTATGTATTCTGGGTGCGACAGGCT

CGTGGACAACGCCTTGAGTGGATAGGTGACATTAATCCTGTCAATGGTGATACTAACTTC

AATGAGAAATTCAAGAACAGACTCACCATCTCCAAGGACACCTCCAAAAACCAGGTGGTC

CTTACAATGACCAACATGGACCCTGTGGACACAGCCACGTATTACTGTGCAAGAGGGGGT

TATACTATGGACTACTGGGGCCAGGGA

>pVxK7b-037-hum16-HC (SEQ ID NO: 98)
CAGGTGCAGCTGCAGGAGTCGGGCCCAGGACTGGTGAAGCCTTCACAGACCCTGTCCCTC

ACCTGCACTGTCTCTGGCTACACCTTCACCAACTACTATGTATTCTGGGTGCGACAGGCT

CGTGGACAACGCCTTGAGTGGATAGGTGACATTAATCCTGTCAATGGTGATACTAACTTC

AATGAGAAATTCAAGAACAGAGTCACCATCTCAGCCGACAAGTCCATCAGCACCGCCTAC

CTGCAGTGGAGCAGCCTGAAGGCCTCGGACACCGCCATGTATTACTGTGCGAGAGGGGGT

TATACTATGGACTACTGGGGCCAGGGA

>pVxK7b-037-hum17-HC (SEQ ID NO: 99)
GAGGTCCAGCTGGTACAGTCTGGGGCTGAGGTGAAGAAGCCTGGGGCTACAGTGAAAATC

TCCTGCAAGGTTTCTGGCTACACCTTCACCAACTACTATGTATTCTGGATCCGCCAGCCC

CCAGGGAAGGGGCTGGAGTGGATTGGTGACATTAATCCTGTCAATGGTGATACTAACTTC

AATGAGAAATTCAAGAACAGAGTCACGATTACCGCGGACAAATCCACGAGCACAGCCTAC

ATGGAGCTGAGCAGCCTGAGATCTGAGGACACGGCCGTGTATTACTGTGCGAGAGGGGGT

TATACTATGGACTACTGGGGCCAGGGA

>pVxK7b-037-hum18-HC (SEQ ID NO: 100)
GAAGTGCAGCTGGTGCAGTCTGGAGCAGAGGTGAAAAAGCCCGGGGAGTCTCTGAGGATC

TCCTGTAAGGGTTCTGGCTACACCTTCACCAACTACTATGTATTCTGGATCAGGCAGTCC

CCATCGAGAGGCCTTGAGTGGCTGGGTGACATTAATCCTGTCAATGGTGATACTAACTTC

AATGAGAAATTCAAGAACAGAGTCACGATTACCGCGGACAAATCCACGAGCACAGCCTAC

-continued

ATGGAGCTGAGCAGCCTGAGATCTGAGGACACGGCCGTGTATTACTGTGCGAGAGGGGT

TATACTATGGACTACTGGGGCCAGGGA

>pVxK7b-037-hum19-HC
(SEQ ID NO: 101)
GAAGTGCAGCTGGTGCAGTCTGGAGCAGAGGTGAAAAAGCCCGGGGAGTCTCTGAGGATC

TCCTGTAAGGGTTCTGGCTACACCTTCACCAACTACTATGTATTCTGGATCAGGCAGTCC

CCATCGAGAGGCCTTGAGTGGCTGGGTGACATTAATCCTGTCAATGGTGATACTAACTTC

AATGAGAAATTCAAGAACAGAGTCACGATTACCGCGGACAAATCCACGAGCACAGCCTAC

ATGGAGCTGAGCAGCCTGAGATCTGAGGACACGGCCGTGTATTACTGTGCGAGAGGGGT

TATACTATGGACTACTGGGGCCAGGGA

>pVxK7b-037-hum20-HC
(SEQ ID NO: 102)
CAGATCACCTTGAAGGAGTCTGGTCCTACGCTGGTGAAACCCACACAGACCCTCACGCTG

ACCTGCACCTTCTCTGGCTACACCTTCACCAACTACTATGTATTCTGGGTGCGACAGGCC

CCTGGACAAGGGCTTGAGTGGATGGGTGACATTAATCCTGTCAATGGTGATACTAACTTC

AATGAGAAATTCAAGAACAGAGTCACGATTACCGCGGACAAATCCACGAGCACAGCCTAC

ATGGAGCTGAGCAGCCTGAGATCTGAGGACACGGCCGTGTATTACTGTGCGAGAGGGGT

TATACTATGGACTACTGGGGCCAGGGA

>pVxK7b-037-hum21-HC
(SEQ ID NO: 103)
CAGGTGCAGCTGCAGGAGTCGGGCCCAGGACTGGTGAAGCCTTCACAGACCCTGTCCCTC

ACCTGCACTGTCTCTGGCTACACCTTCACCAACTACTATGTATTCTGGGTGCGACAGGCT

CGTGGACAACGCCTTGAGTGGATAGGTGACATTAATCCTGTCAATGGTGATACTAACTTC

AATGAGAAATTCAAGAACAGACTCACCATCTCCAAGGACACCTCCAAAAACCAGGTGGTC

CTTACAATGACCAACATGGACCCTGTGGACACAGCCACGTATTACTGTGCAAGAGGGGGT

TATACTATGGACTACTGGGGCCAGGGA

>pVxK7b-037-hum22-HC
(SEQ ID NO: 104)
CAGGTGCAGCTGCAGGAGTCGGGCCCAGGACTGGTGAAGCCTTCACAGACCCTGTCCCTC

ACCTGCACTGTCTCTGGCTACACCTTCACCAACTACTATGTATTCTGGGTGCGACAGGCT

CGTGGACAACGCCTTGAGTGGATAGGTGACATTAATCCTGTCAATGGTGATACTAACTTC

AATGAGAAATTCAAGAACAGACTCACCATCTCCAAGGACACCTCCAAAAACCAGGTGGTC

CTTACAATGACCAACATGGACCCTGTGGACACAGCCACGTATTACTGTGCAAGAGGGGGT

TATACTATGGACTACTGGGGCCAGGGA

>pVxK7b-037-hum23-HC
(SEQ ID NO: 105)
CAGGTGCAGCTGCAGGAGTCGGGCCCAGGACTGGTGAAGCCTTCACAGACCCTGTCCCTC

ACCTGCACTGTCTCTGGCTACACCTTCACCAACTACTATGTATTCTGGGTGCGACAGGCT

CGTGGACAACGCCTTGAGTGGATAGGTGACATTAATCCTGTCAATGGTGATACTAACTTC

AATGAGAAATTCAAGAACAGACTCACCATCTCCAAGGACACCTCCAAAAACCAGGTGGTC

CTTACAATGACCAACATGGACCCTGTGGACACAGCCACGTATTACTGTGCAAGAGGGGGT

TATACTATGGACTACTGGGGCCAGGGA

>pVxK7b-037-hum24-HC
(SEQ ID NO: 106)
CAGGTGCAGCTGCAGGAGTCGGGCCCAGGACTGGTGAAGCCTGGGGCTACAGTGAAAATC

TCCTGCAAGGTTTCTGGCTACACCTTCACCAACTACTATGTATTCTGGGTGCGACAGGCT

CGTGGACAACGCCTTGAGTGGATAGGTGACATTAATCCTGTCAATGGTGATACTAACTTC

AATGAGAAATTCAAGAACAGAGTCACGATTACCGCGGACAAATCCACGAGCACAGCCTAC

ATGGAGCTGAGCAGCCTGAGATCTGAGGACACGGCCGTGTATTACTGTGCGAGAGGGGGT

TATACTATGGACTACTGGGGCCAGGGA

Complete Light Chain Amino Acid Sequences

>VxP037-01-LC-Pro represents the full length light chain variable domain+constant domain amino acid sequence. The underlined amino acid sequence=framework 4+the constant domain. All the humanized light chain sequences contain the same constant domain as VxP037-01-LC-Pro. However, this is not shown in the remaining humanized light chain amino acid sequences.

>VxP037-01-LC-Pro
(SEQ ID NO: 107)
DVVMTQTPLSLSVSLGDQASISCRSSQSLVHSNGNTYLHWYLQKPGQSPKLLIYKVSYR

FSGVPDRFSGSGSGTDFTLKISRVEAEDLGVYFCSQNTHVPRTFGQG<u>TKVEIKRTVAAPS</u>

<u>VFIFPPSDEQLKSGTASVVCLLNNFYPREAKVQWKVDNALQSGNSQESVTEQDSKDSTY</u>

<u>SLSSTLTLSKADYEKHKVYACEVTHQGLSSPVTKSFNRGEC</u>

Complete Light Chain Nucleic Acid Sequences

The underlined nucleic acid sequence encodes the underlined protein sequence in >VxP037-01-LC-Pro, above.

>Vx-P037-01-LC-DNA
(SEQ ID NO: 108)
GATGTTGTTATGACCCAAACTCCACTCTCCCTGTCTGTCAGTCTTGGAGA

TCAAGCCTCCATCTCTTGCAGATCTAGTCAGAGCCTTGTACACAGTAATG

GAAACACCTATTTACATTGGTACCTGCAGAAGCCAGGCCAGTCTCCAAAG

CTCCTGATCTACAAAGTTTCCTACCGATTTTCTGGGGTCCCAGACAGGTT

CAGTGGCAGTGGATCAGGGACAGATTTCACACTCAAGATCAGCAGAGTGG

AGGCTGAGGATCTGGGAGTTTATTTCTGCTCTCAAAATACACATGTTCCT

CGGACGTTCGGCCAAGGG<u>ACCAAGGTGGAAATCAAACGTACGGTGGCTGC</u>

<u>ACCATCTGTCTTCATCTTCCCGCCATCTGATGAGCAGTTGAAATCTGGAA</u>

<u>CTGCCTCTGTTGTGTGCCTGCTGAATAACTTCTATCCCAGAGAGGCCAAA</u>

<u>GTACAGTGGAAGGTGGATAACGCCCTCCAATCGGGTAACTCCCAGGAGAG</u>

<u>TGTCACAGAGCAGGACAGCAAGGACAGCACCTACAGCCTCAGCAGCACCC</u>

<u>TGACGCTGAGCAAAGCAGACTACGAGAAACACAAAGTCTACGCCTGCGAA</u>

<u>GTCACCCATCAGGGCCTGAGCTCGCCCGTCACAAAGAGCTTCAACAGGGG</u>

<u>AGAGTGTTGA</u>

Complete Heavy Chain Amino Acid Sequences

>VxP037-01-HC-Pro represents the full length heavy chain variable domain+constant domain amino acid sequence. The underlined amino acid sequence=framework 4+the constant domain. All the humanized heavy chain sequences contain the same constant domain as >VxP037-01-HC-Pro. However, this is not shown in the remaining humanized heavy chain amino acid sequences.

>VxP037-01-HC-Pro
(SEQ ID NO: 109)
EVQLQQFGAELVKPGASMKLSCKASGYTFTNYYVFWVKQRPGQGLEWIGDINPVNGDT

NFNEKFKNKATLTVDKSSTTTYLQLSSLTSEDSAVYYCTRGGYTMDYWGQG<u>TLVTVSS</u>

<u>ASTKGPSVFPLAPSSKSTSGGTAALGCLVKDYFPEPVTVSWNSGALTSGVHTFPAVLQSS</u>

<u>GLYSLSSVVTVPSSSLGTQTYICNVNHKPSNTKVDKKVEPKSCDKTHTCPPCPAPELLGG</u>

<u>PSVFLFPPKPKDTLMISRTPEVTCVVVDVSHEDPEVKFNWYVDGVEVHNAKTKPREEQY</u>

<u>NSTYRVVSVLTVLHQDWLNGKEYKCKVSNKALPAPIEKTISKAKGQPREPQVYTLPPSR</u>

<u>DELTKNQVSLTCLVKGFYPSDIAVEWESNGQPENNYKTTPPVLDSDGSFFLYSKLTVDK</u>

<u>SRWQQGNVFSCSVMHEALHNHYTQKSLSLSPGK</u>

Complete Heavy Chain Nucleic Acid Sequences
The underlined nucleic acid sequence encodes the underlined protein sequence in >VxP037-01-HC-Pro, above.

>VxP037-01-HC-DNA                                           (SEQ ID NO: 110)
GAGGTCCAGCTGCAGCAGTTTGGGGCTGAACTGGTGAAGCCTGGGGCTTCAATGAAGTTGTC

CTGCAAGGCTTCTGGCTACACCTTCACCAACTACTATGTATTCTGGGTGAAACAGAGGCCTG

GACAAGGCCTTGAGTGGATTGGAGACATTAATCCTGTCAATGGTGATACTAACTTCAATGAG

AAATTCAAGAACAAGGCCACACTGACTGTAGACAAGTCCTCCACCACAACATACTTGCAACT

CAGCAGCCTGACATCTGAGGACTCTGCGGTCTATTACTGTACAAGAGGGGGTTATACTATGG

ACTACTGGGGCCAGGGA<u>ACGCTGGTCACCGTCAGCTCAGCCTCCACCAAGGGCCCATCGGTC</u>

<u>TTCCCCCTGGCACCCTCCTCCAAGAGCACCTCTGGGGGCACAGCGGCCCTGGGCTGCCTGGT</u>

<u>CAAGGACTACTTCCCCGAACCGGTGACGGTGTCGTGGAACTCAGGCGCCCTGACCAGCGGC</u>

<u>GTGCACACCTTCCCGGCTGTCCTACAGTCCTCAGGACTCTACTCCCTCAGCAGCGTGGTGAC</u>

<u>CGTGCCCTCCAGCAGCTTGGGCACCCAGACCTACATCTGCAACGTGAATCACAAGCCCAGCA</u>

<u>ACACCAAGGTGGACAAGAAAGTTGAGCCCAAATCTTGTGACAAAACTCACACATGCCCACC</u>

<u>GTGCCCAGCACCTGAACTCCTGGGGGGACCGTCAGTCTTCCTCTTCCCCCCAAAACCCAAGG</u>

<u>ACACCCTCATGATCTCCCGGACCCCTGAGGTCACATGCGTGGTGGTGGACGTGAGCCACGAA</u>

<u>GACCCTGAGGTCAAGTTCAACTGGTACGTGGACGGCGTGGAGGTGCATAATGCCAAGACAA</u>

<u>AGCCGCGGGAGGAGCAGTACAACAGCACGTACCGTGTGGTCAGCGTCCTCACCGTCCTGCA</u>

<u>CCAGGACTGGCTGAATGGCAAGGAGTACAAGTGCAAGGTCAGCAACAAAGCCCTCCCAGCC</u>

<u>CCCATCGAGAAAACCATCTCCAAAGCCAAAGGGCAGCCCCGAGAACCACAGGTGTACACCC</u>

<u>TGCCCCCATCCCGGGATGAGCTGACCAAGAACCAGGTCAGCCTGACCTGCCTGGTCAAAGG</u>

<u>CTTCTATCCCAGCGACATCGCCGTGGAGTGGGAGAGCAATGGGCAGCCGGAGAACAACTAC</u>

<u>AAGACCACGCCTCCCGTGCTGGACTCCGACGGCTCCTTCTTCCTCTACAGCAAGCTCACCGT</u>

<u>GGACAAGAGCAGGTGGCAGCAGGGGAACGTCTTCTCATGCTCCGTGATGCATGAGGCTCTG</u>

<u>CACAACCACTACACGCAGAAGAGCCTCTCCCTGTCTCCGGGTAAATGA</u>

---

What is claimed is:

1. A monoclonal antibody, or antigen-binding fragment thereof, that specifically binds CD47, wherein the monoclonal antibody, or antigen-binding fragment thereof, comprises three light chain complementarity determining regions (LCDRs 1-3) and three heavy chain complementarity determining regions (HCDRs 1-3), wherein:
   LCDR 1 comprises the amino acid sequence RSSQSLVHSNGNTYLH (SEQ ID NO:1);
   LCDR 2 comprises the amino acid sequence KVSYRFS (SEQ ID NO:2); and
   LCDR 3 comprises the amino acid sequence SQNTHVPRT (SEQ ID NO:3);
   HCDR 1 comprises the amino acid sequence GYTFTNYYVF (SEQ ID NO:4);
   HCDR 2 comprises the amino acid sequence DINPVNGDTNFNEKFKN (SEQ ID NO:5); and
   HCDR 3 comprises the amino acid sequence GGYTMDY (SEQ ID NO:6).

2. The monoclonal antibody, or antigen-binding fragment thereof, of claim 1, which is chimeric or humanized.

3. The monoclonal antibody, or antigen-binding fragment thereof, of claim 1, which specifically binds human, rat, mouse, and pig CD47.

4. The monoclonal antibody, or antigen-binding fragment thereof, of claim 1, which comprises a light chain variable region (LCVR) and a heavy chain variable region (HCVR), wherein said LCVR and said HCVR comprise, respectively, amino acid sequences selected from the group consisting of:

SEQ ID NO:7 and SEQ ID NO:57;
SEQ ID NO:8 and SEQ ID NO:58;
SEQ ID NO:9 and SEQ ID NO:59;
SEQ ID NO:10 and SEQ ID NO:60;
SEQ ID NO:11 and SEQ ID NO:61;
SEQ ID NO:12 and SEQ ID NO:62;
SEQ ID NO:13 and SEQ ID NO:63;
SEQ ID NO:14 and SEQ ID NO:64;
SEQ ID NO:15 and SEQ ID NO:65;
SEQ ID NO:16 and SEQ ID NO:66;
SEQ ID NO:17 and SEQ ID NO:67;
SEQ ID NO:18 and SEQ ID NO:68;
SEQ ID NO:19 and SEQ ID NO:69;
SEQ ID NO:20 and SEQ ID NO:70;
SEQ ID NO:21 and SEQ ID NO:71;
SEQ ID NO:22 and SEQ ID NO:72;
SEQ ID NO:23 and SEQ ID NO:73;
SEQ ID NO:24 and SEQ ID NO:74;
SEQ ID NO:25 and SEQ ID NO:75;
SEQ ID NO:26 and SEQ ID NO:76;
SEQ ID NO:27 and SEQ ID NO:77;
SEQ ID NO:28 and SEQ ID NO:78;
SEQ ID NO:29 and SEQ ID NO:79;
SEQ ID NO:30 and SEQ ID NO:80; and
SEQ ID NO:31 and SEQ ID NO:81.

5. A pharmaceutical composition, comprising said monoclonal antibody, or antigen-binding fragment thereof, of claim 1, and a pharmaceutically or physiologically acceptable carrier, diluent, or excipient.

* * * * *